US009427461B2

(12) United States Patent
Nakamura et al.

(10) Patent No.: US 9,427,461 B2
(45) Date of Patent: Aug. 30, 2016

(54) TOPK PEPTIDES AND VACCINES INCLUDING THE SAME

(71) Applicant: ONCOTHERAPY SCIENCE, INC., Kanagawa (JP)

(72) Inventors: Yusuke Nakamura, Tokyo (JP); Takuya Tsunoda, Kanagawa (JP); Ryuji Osawa, Kanagawa (JP); Sachiko Yoshimura, Kanagawa (JP); Tomohisa Watanabe, Kanagawa (JP); Gaku Nakayama, Kanagawa (JP)

(73) Assignee: OncoTherapy Science, Inc., Kanagawa (JP)

( * ) Notice: Subject to any disclaimer, the term of this patent is extended or adjusted under 35 U.S.C. 154(b) by 33 days.

(21) Appl. No.: 14/353,261

(22) PCT Filed: Oct. 25, 2012

(86) PCT No.: PCT/JP2012/006853
§ 371 (c)(1),
(2) Date: Apr. 21, 2014

(87) PCT Pub. No.: WO2013/061594
PCT Pub. Date: May 2, 2013

(65) Prior Publication Data
US 2014/0255437 A1    Sep. 11, 2014

Related U.S. Application Data

(60) Provisional application No. 61/552,817, filed on Oct. 28, 2011.

(51) Int. Cl.
| | | |
|---|---|---|
| A61K 39/00 | (2006.01) | |
| C07K 16/18 | (2006.01) | |
| C07K 7/06 | (2006.01) | |
| G01N 33/574 | (2006.01) | |
| C07K 14/47 | (2006.01) | |
| G01N 33/50 | (2006.01) | |
| C12N 9/12 | (2006.01) | |
| A61K 38/00 | (2006.01) | |

(52) U.S. Cl.
CPC ............ *A61K 39/0005* (2013.01); *C07K 7/06* (2013.01); *C07K 14/4748* (2013.01); *C07K 16/18* (2013.01); *C12N 9/1205* (2013.01); *G01N 33/505* (2013.01); *G01N 33/574* (2013.01); *A61K 38/00* (2013.01); *A61K 39/0011* (2013.01)

(58) Field of Classification Search
None
See application file for complete search history.

(56) References Cited

U.S. PATENT DOCUMENTS

| | | | |
|---|---|---|---|
| 6,759,046 B1 * | 7/2004 | Gaudernack ....... | C07K 14/4748 |
| | | | 424/184.1 |
| 7,531,300 B2 | 5/2009 | Nakamura et al. | |
| 7,998,695 B2 | 8/2011 | Nakamura et al. | |
| 2005/0064402 A1 * | 3/2005 | Goldsworthy et al. ........... 435/6 | |
| 2006/0194199 A1 | 8/2006 | Nakamura et al. | |
| 2007/0269432 A1 | 11/2007 | Nakamura et al. | |
| 2009/0175844 A1 | 7/2009 | Nakamura et al. | |
| 2009/0286856 A1 | 11/2009 | Nakamura et al. | |
| 2009/0317392 A1 | 12/2009 | Nakamura et al. | |
| 2011/0135647 A1 | 6/2011 | Nakamura et al. | |
| 2011/0229504 A1 | 9/2011 | Fritsche et al. | |
| 2011/0313018 A1 | 12/2011 | Nakamura et al. | |
| 2012/0010090 A1 | 1/2012 | Nakamura et al. | |
| 2012/0014996 A1 | 1/2012 | Nakamura et al. | |
| 2013/0011933 A1 | 1/2013 | Nakamura et al. | |

FOREIGN PATENT DOCUMENTS

| | | |
|---|---|---|
| EP | 1972639 A2 | 9/2008 |
| JP | 2004-510442 A | 4/2004 |
| JP | 2007-506424 A | 3/2007 |
| WO | 02/29104 A2 | 4/2002 |
| WO | 2004/031410 A2 | 4/2004 |
| WO | 2005/028676 A2 | 3/2005 |
| WO | 2006/085684 A2 | 8/2006 |
| WO | 2007/013665 A2 | 2/2007 |
| WO | 2008/018642 A2 | 2/2008 |
| WO | 2010/023854 A1 | 3/2010 |
| WO | 2010/100878 A1 | 9/2010 |
| WO | 2011/113819 A2 | 9/2011 |

OTHER PUBLICATIONS

Geneseq Accession No. GSP:AZM95538, "HLA A*024 binding human PBK peptide SEQ ID No. 50" (2011).
Geneseq Accession No. GSP:ATM92965, "Human carcinoma-related signaling peptide, PBK, SEQ ID 177" (2008).
Geneseq Accession No. GSP:ARA28704, "Inhibitory polypeptide, SEQ ID No. 98" (2008).
Gaudet et al., "Characterization of PDZ-binding kinase, a mitotic kinase", Proc Natl Acad Sci USA, vol. 97(10), pp. 5167-5172 (2000).

(Continued)

*Primary Examiner* — Sheela J Huff
(74) *Attorney, Agent, or Firm* — Kilpatrick Townsend & Stockton LLP

(57) ABSTRACT

The present invention provides isolated epitope peptides derived from TOPK and immunogenic fragments thereof have an ability to induce cytotoxic T lymphocytes (CTLs) and thus are suitable for use in cancer immunotherapy, more particularly as cancer vaccines. The peptides of the present invention encompass both of peptides including a TOPK-derived amino acid sequence and modified versions thereof, in which one, two, or several amino acids are substituted, deleted, inserted and/or added, provided such modified versions have CTL inducibility. Further provided are polynucleotides encoding any of the aforementioned peptides as well as pharmaceutical compositions that include any of the aforementioned peptides or polynucleotides. The peptides, polynucleotides, and pharmaceutical compositions of this invention find particular utility in either or both of the treatment and prevention of a number of cancers.

1 Claim, 8 Drawing Sheets

(56) References Cited

OTHER PUBLICATIONS

Abe et al., "Cloning and Expression of a Novel MAPPK-like Protein Kinase, Lymphokine-activated Killer T-cell-originated Protein Kinase, Specifically Expressed in the Testis and Activated Lumphoid Cells", *J. Biol Chem.*, vol. 275, No. 28, pp. 21525-21531 (2000).
Adams, et al., "Prediction of binding to MHC class I molecules", *J. Immunol Methods*, vol. 185, No. 2, pp. 181-190 (1995).
Alvarez et al., "Analysis of the HLA class I associated peptide repertoire in a hepatocellular carcinoma cell line reveals tumor-specific peptides as putative targets for immunotherapy", *Proteomics Clin Appl.* vol. 1, No. 3, pp. 286-298 (2007).
Ayllon et al., PBK/TOPK promotes tumour cell proliferation through p38 MAPK activity and regulation of the DNA damage response, *Oncogene*, vol. 26, No. 24, pp. 3451-3461 (2007).
Azuma et al., "Identification of novel human cancer/testis antigens", *Int. J. Hematol. Suppl.*, vol. 73, No. 1, pp. 148 (2001).
Belli, et al., "Vaccination of Metastatic Melanoma Patients with Autologous Tumor-Derived Heat Shock Protein gp96-Peptide complexes: Clinical and Immunologic Findings", *J Clin Oncol.*, vol. 20, No. 20, pp. 4169-4180 (2002).
Boon T., "Tumor Antigens Recognized by Cytolytic T Lymphocytes: Present Perspectives for Specific Immunotherapy," *Int J Cancer*, vol. 54, No. 2, pp. 177-180 (1993).
Boon T., et al., "Human Tumor Antigens Recognized by T Lymphocytes," *J Exp Med.*, vol. 183(3), pp. 725-729 (1996).
Butterfield, et al., "Generation of Human T-cell Response to an HLA-A2.1-restricted Peptide Epitope Derived from α—Fetoprotein," *Cancer Res.*, vol. 59, No. 13, pp. 3134-3142 (1999).
Coulie, et al., "Cytolytic T-cell Responses of cancer patients vaccinated with a MAGE antigen", *Immunol Rev.*, vol. 188, pp. 33-42 (2002).
Dionne, et al., "Functional characterization of CTL against gp100 altered peptide ligands", *Cancer Immunol Immunother.* vol. 52, No. 4, pp. 199-206 (2003).
Dionne, et al., "Her-2/neu altered peptide ligand-induced CTL responses: implications for peptides with increased HLA affinity and T-cell-receptor interaction", *Cancer Immunol Immunother.* vol. 53, No. 4, pp. 307-314 (2004).
Falk, et al., "Allele-specific motifs revealed by sequencing of self-peptides eluted from MHC molecules", *Nature*, vol. 351, No. 6324, pp. 290-296 (1991).
Fujie, et al., "A Mage-1-Encoded HLA-A24-Binding Synthetic Peptide Induces Specific Anti-tumor Cytotoxic T Lymphocytes", *Int. J. Cancer.*, vol. 80, No. 2, pp. 169-172 (1999).
Harris, "Structure and Function of the p53 Tumor Suppressor Gene: Clues for Rational Cancer Cancer Therapeutic Strategies," *J Natl Cancer Inst.*, vol. 88, No. 20, pp. 1442-1455 (1996).
He et al., "PBK/TOPK in the differential diagnosis of cholangiocarcinoma from hepatocellular carcinoma and its involvement in prognosis of human cholangiocarcinoma", *Hum Pathol.*, vol. 41, No. 3, pp. 415-424 (2010).

Hoffmann, et al., "The Ability of Variant Peptides to Reserve the Nonresponsiveness of T Lymphocytes to the Wild-Type Sequence $p53_{264-272}$ Epitope," *J Immunol*, vol. 168, No. 3, pp. 1338-1347 (2002).
Kikuchi, et al., "Identification of a Sart-1-Derived Peptide Capable of Inducing HLA-A24-Restricted and Tumor-Specific T Lymphocytes", *Int. J Cancer*, vol. 81, No. 3, pp. 459-466 (1999).
Kondo, et al., "Prominent Roles of Secondary Anchor Residues in Peptide Binding to HLA-A24 Human Class I Molecules", *J. Immunol.* vol. 155, No. 9, pp. 4307-4312 (1995).
Kubo, et al., "Definition of Specific Petptide Motifs for Four Major HLA-A Alleles", *J Immunol*, vol. 152, No. 8, pp. 3913-3924 (1994).
Li et al., Identification and Characterization of HLA-class-I-restricted T-cell epitopes in the putative tumor-associated antigens P21-activated serin kinase 2 (PAK2) and cyclin-dependent kinase inhibitor 1A (CDKN1A), *Ann Hematol.*, vol. 85, No. 9, pp. 583-590 (2006).
Minoo et al., "Characterization of rectal, proximal and distal colon cancers based on clinicopathological, molecular and protein profiles", *Int J Oncol.*, vol. 37, No. 3, pp. 707-718 (2010).
Oiso, et al., "A Newly Identified Mage-3-Derived Epitope Recognized by HLA-A24-Restricted Cytotoxic T Lymphocytes", *Int. J Cancer*, vol. 81, No. 3, pp. 387-394 (1999).
Park et al., "PDZ-Binding Kinase/T-LAK Cell-Originated Protein Kinase, a Putative Cancer/Testis Antigen with an Oncogenic Activity in Breast Cancer", *Cancer Res*, vol. 66, No. 18, pp. 9186-9195 (2006).
Parker, et al., "Scheme for Ranking Potential HLA-A2 Binding Peptides Based on Independent Binding of Individual Peptide Side-Chains", *J Immunol.*, vol. 152, No. 1, pp. 163-175 (1994).
Rammensee, et al., "MHC ligands and peptide motifs: first listing," *Immunogenetics*, vol. 41(4), pp. 178-228 (1995).
Rosenberg, et al., "Cancer immunotherapy: moving beyond current vaccines", *Nat. Med.* vol. 10, No. 9, pp. 909-915 (2004).
Schueler-Furman, et al., "Structure-based prediction of binding peptides to MHC class I molecules: Application to a broad range of MHC alleles", *Protein Sci.*, vol. 9, No. 9, pp. 1838-1846 (2000).
Tanaka, et al., "Induction of Antitumor Cytotoxic T Lymphocytes with a MAGE-3-encoded Synthetic Peptide Presented by Human Leukocytes Antigen-A24", *Cancer Res.*, vol. 57, No. 20, pp. 4465-4468 (1997).
Van Der Burg, et al., "Immunogenicity of Peptides Bound to MHC Class I Molecules Depends on the MHC-Peptide Complex Stability,"*J. Immunol.*, vol. 156, No. 9, pp. 3308-3314 (1996).
Vissers, et al., "The Renal Cell Carcinoma-associated Antigen G250 Encodes a Human Leukocyte Antigen (HLA)-A2.1-restricted Epitope Recognized by Cytotoxic T Lymphocytes", *Cancer Res.*, vol. 59, No. 21, pp. 5554-5559 (1999).
Zaremba, et al., "Identification of an Enhancer Agonist Cytotoxic T Lymphocytes Peptide from Human Carcinoembryonic Antigen", *Cancer Res.*, vol. 57, No. 20, pp. 4570-4577 (1997).
Zykova et al., "Lymphokine-Activated Killer T-Cell-Originated Protein Kinase Phosphorylation of H2AX Prevents Arsenite-Induced Apoptosis in RPMI7951 Melanoma Cell", *Clin Cancer Res*, vol. 12, No. 23, pp. 6884-6893 (2006).
U.S. Appl. No. 14/162,487, filed Jan 23, 2014, 211 pages.
International Search Report and Written Opinion issued on Nov. 20, 2012 for International Patent Application No. PCT/JP2012/006853.

\* cited by examiner

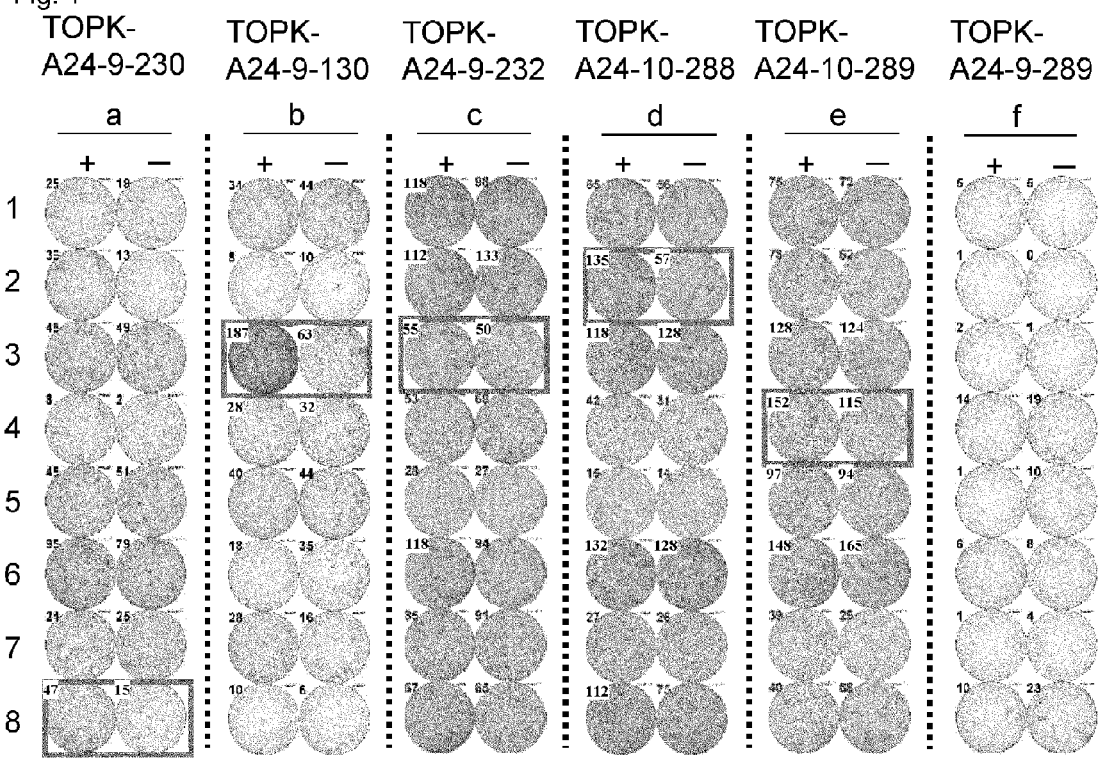

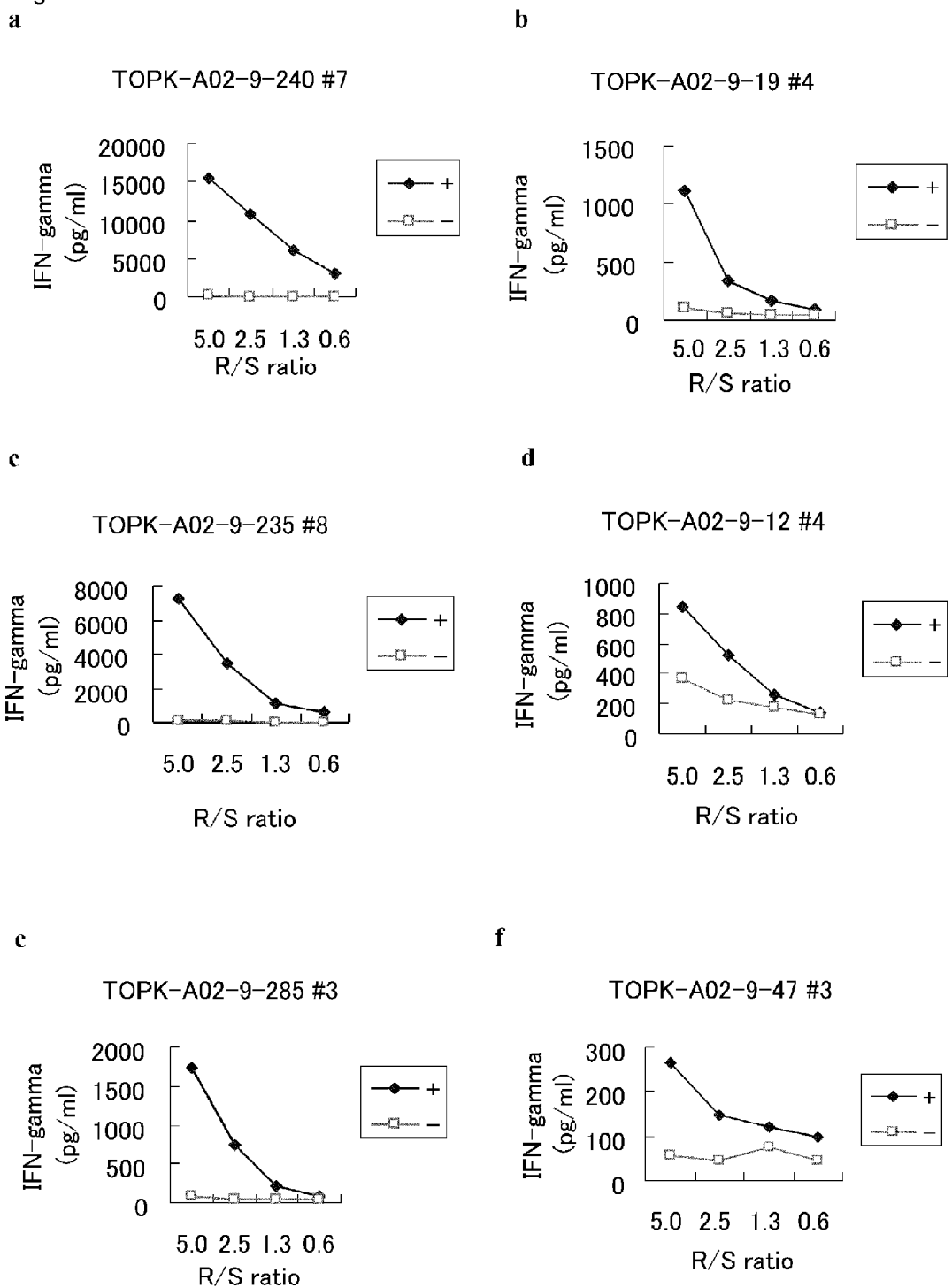

Fig. 5-2
g
TOPK-A02-10-236 #5
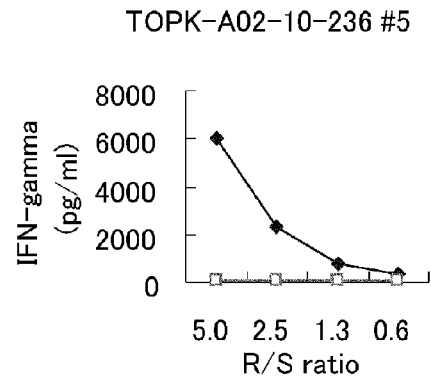
h
TOPK-A02-10-231 #3
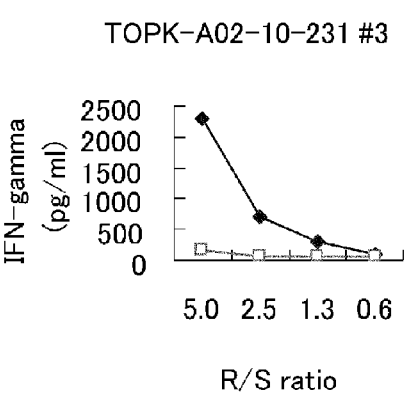
i
TOPK-A02-10-47 #8
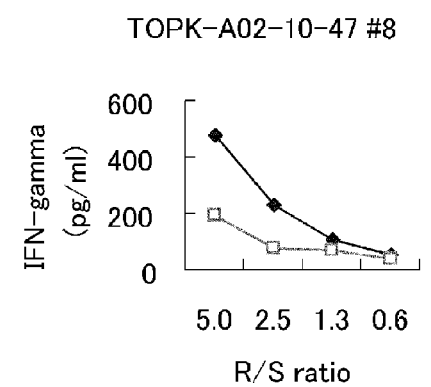
j
TOPK-A02-10-239 #1
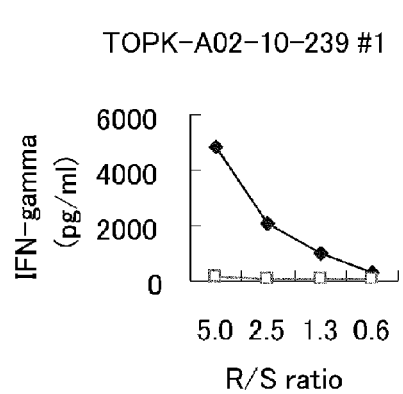
k
TOPK-A02-10-88 #4
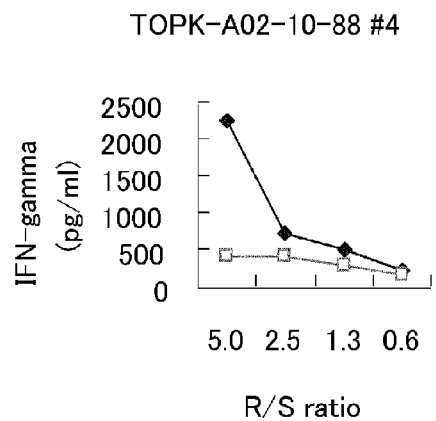

a b

SEQUENCE LISTING

```
<160> NUMBER OF SEQ ID NOS: 90

<210> SEQ ID NO 1
<211> LENGTH: 9
<212> TYPE: PRT
<213> ORGANISM: Artificial Sequence
<220> FEATURE:
<223> OTHER INFORMATION: a peptide derived from TOPK

<400> SEQUENCE: 1

Ser Tyr Gln Lys Val Ile Glu Leu Phe
1               5

<210> SEQ ID NO 2
<211> LENGTH: 9
<212> TYPE: PRT
<213> ORGANISM: Artificial Sequence
<220> FEATURE:
<223> OTHER INFORMATION: a peptide derived from TOPK

<400> SEQUENCE: 2

Ile Phe Ala Phe Gly Leu Thr Leu Trp
1               5

<210> SEQ ID NO 3
<211> LENGTH: 9
<212> TYPE: PRT
<213> ORGANISM: Artificial Sequence
<220> FEATURE:
<223> OTHER INFORMATION: a peptide derived from TOPK

<400> SEQUENCE: 3

Arg Tyr Lys Ala Ser Gln Asp Pro Phe
1               5

<210> SEQ ID NO 4
<211> LENGTH: 9
<212> TYPE: PRT
<213> ORGANISM: Artificial Sequence
<220> FEATURE:
<223> OTHER INFORMATION: a peptide derived from TOPK

<400> SEQUENCE: 4

Leu Trp Glu Met Met Thr Leu Ser Ile
1               5

<210> SEQ ID NO 5
<211> LENGTH: 9
<212> TYPE: PRT
<213> ORGANISM: Artificial Sequence
<220> FEATURE:
<223> OTHER INFORMATION: a peptide derived from TOPK
```

```
<400> SEQUENCE: 5

Lys Tyr Leu His Gln Glu Lys Lys Leu
1               5

<210> SEQ ID NO 6
<211> LENGTH: 9
<212> TYPE: PRT
<213> ORGANISM: Artificial Sequence
<220> FEATURE:
<223> OTHER INFORMATION: a peptide derived from TOPK

<400> SEQUENCE: 6

Ala Phe Gly Leu Thr Leu Trp Glu Met
1               5

<210> SEQ ID NO 7
<211> LENGTH: 9
<212> TYPE: PRT
<213> ORGANISM: Artificial Sequence
<220> FEATURE:
<223> OTHER INFORMATION: a peptide derived from TOPK

<400> SEQUENCE: 7

Val Ile Lys Gly Asp Phe Glu Thr Ile
1               5

<210> SEQ ID NO 8
<211> LENGTH: 9
<212> TYPE: PRT
<213> ORGANISM: Artificial Sequence
<220> FEATURE:
<223> OTHER INFORMATION: a peptide derived from TOPK

<400> SEQUENCE: 8

His Tyr Arg Ser Val Tyr Gln Lys Arg
1               5

<210> SEQ ID NO 9
<211> LENGTH: 9
<212> TYPE: PRT
<213> ORGANISM: Artificial Sequence
<220> FEATURE:
<223> OTHER INFORMATION: a peptide derived from TOPK

<400> SEQUENCE: 9

Leu Thr Leu Trp Glu Met Met Thr Leu
1               5

<210> SEQ ID NO 10
<211> LENGTH: 9
<212> TYPE: PRT
<213> ORGANISM: Artificial Sequence
<220> FEATURE:
<223> OTHER INFORMATION: a peptide derived from TOPK

<400> SEQUENCE: 10

Ser Val Leu Cys Ser Thr Pro Thr Ile
1               5

<210> SEQ ID NO 11
<211> LENGTH: 9
<212> TYPE: PRT
<213> ORGANISM: Artificial Sequence
<220> FEATURE:
<223> OTHER INFORMATION: a peptide derived from TOPK

<400> SEQUENCE: 11
```

```
Cys Tyr Ile Gly Thr Glu Pro Trp Lys
1               5

<210> SEQ ID NO 12
<211> LENGTH: 9
<212> TYPE: PRT
<213> ORGANISM: Artificial Sequence
<220> FEATURE:
<223> OTHER INFORMATION: a peptide derived from TOPK

<400> SEQUENCE: 12

Val Tyr Gln Lys Arg Leu Met Asp Glu
1               5

<210> SEQ ID NO 13
<211> LENGTH: 9
<212> TYPE: PRT
<213> ORGANISM: Artificial Sequence
<220> FEATURE:
<223> OTHER INFORMATION: a peptide derived from TOPK

<400> SEQUENCE: 13

Ala Tyr Tyr Ala Ala Leu Gly Thr Arg
1               5

<210> SEQ ID NO 14
<211> LENGTH: 9
<212> TYPE: PRT
<213> ORGANISM: Artificial Sequence
<220> FEATURE:
<223> OTHER INFORMATION: a peptide derived from TOPK

<400> SEQUENCE: 14

His Ser Pro Trp Ala Val Lys Lys Ile
1               5

<210> SEQ ID NO 15
<211> LENGTH: 9
<212> TYPE: PRT
<213> ORGANISM: Artificial Sequence
<220> FEATURE:
<223> OTHER INFORMATION: a peptide derived from TOPK

<400> SEQUENCE: 15

Arg Leu Met Asp Glu Ala Lys Ile Leu
1               5

<210> SEQ ID NO 16
<211> LENGTH: 9
<212> TYPE: PRT
<213> ORGANISM: Artificial Sequence
<220> FEATURE:
<223> OTHER INFORMATION: a peptide derived from TOPK

<400> SEQUENCE: 16

Arg Pro Pro Ile Asn Met Glu Glu Leu
1               5

<210> SEQ ID NO 17
<211> LENGTH: 9
<212> TYPE: PRT
<213> ORGANISM: Artificial Sequence
<220> FEATURE:
<223> OTHER INFORMATION: a peptide derived from TOPK

<400> SEQUENCE: 17
```

```
Lys Ile Cys Asp Val Gly Val Ser Leu
1               5

<210> SEQ ID NO 18
<211> LENGTH: 9
<212> TYPE: PRT
<213> ORGANISM: Artificial Sequence
<220> FEATURE:
<223> OTHER INFORMATION: a peptide derived from TOPK

<400> SEQUENCE: 18

Lys Ala Asp Ile Phe Ala Phe Gly Leu
1               5

<210> SEQ ID NO 19
<211> LENGTH: 9
<212> TYPE: PRT
<213> ORGANISM: Artificial Sequence
<220> FEATURE:
<223> OTHER INFORMATION: a peptide derived from TOPK

<400> SEQUENCE: 19

Leu Ser Glu Lys Lys Lys Ser Val Leu
1               5

<210> SEQ ID NO 20
<211> LENGTH: 9
<212> TYPE: PRT
<213> ORGANISM: Artificial Sequence
<220> FEATURE:
<223> OTHER INFORMATION: a peptide derived from TOPK

<400> SEQUENCE: 20

Val Ala Leu Asn Met Ala Arg Gly Leu
1               5

<210> SEQ ID NO 21
<211> LENGTH: 9
<212> TYPE: PRT
<213> ORGANISM: Artificial Sequence
<220> FEATURE:
<223> OTHER INFORMATION: a peptide derived from TOPK

<400> SEQUENCE: 21

Ala Ala Ile Ile Leu Lys Val Ala Leu
1               5

<210> SEQ ID NO 22
<211> LENGTH: 9
<212> TYPE: PRT
<213> ORGANISM: Artificial Sequence
<220> FEATURE:
<223> OTHER INFORMATION: a peptide derived from TOPK

<400> SEQUENCE: 22

Phe Thr Glu Ala Asn Asp Gly Ser Leu
1               5

<210> SEQ ID NO 23
<211> LENGTH: 9
<212> TYPE: PRT
<213> ORGANISM: Artificial Sequence
<220> FEATURE:
<223> OTHER INFORMATION: a peptide derived from TOPK

<400> SEQUENCE: 23

Glu Ala Asn Asp Gly Ser Leu Cys Leu
```

```
<210> SEQ ID NO 24
<211> LENGTH: 9
<212> TYPE: PRT
<213> ORGANISM: Artificial Sequence
<220> FEATURE:
<223> OTHER INFORMATION: a peptide derived from TOPK

<400> SEQUENCE: 24

Gly Gly Glu Lys Ser Leu Asn Asp Leu
1               5

<210> SEQ ID NO 25
<211> LENGTH: 10
<212> TYPE: PRT
<213> ORGANISM: Artificial Sequence
<220> FEATURE:
<223> OTHER INFORMATION: a peptide derived from TOPK

<400> SEQUENCE: 25

Ala Ser Pro Phe Met Gln Lys Leu Gly Phe
1               5                   10

<210> SEQ ID NO 26
<211> LENGTH: 10
<212> TYPE: PRT
<213> ORGANISM: Artificial Sequence
<220> FEATURE:
<223> OTHER INFORMATION: a peptide derived from TOPK

<400> SEQUENCE: 26

Lys Tyr Leu His Gln Glu Lys Lys Leu Leu
1               5                   10

<210> SEQ ID NO 27
<211> LENGTH: 10
<212> TYPE: PRT
<213> ORGANISM: Artificial Sequence
<220> FEATURE:
<223> OTHER INFORMATION: a peptide derived from TOPK

<400> SEQUENCE: 27

Glu Ser Tyr Gln Lys Val Ile Glu Leu Phe
1               5                   10

<210> SEQ ID NO 28
<211> LENGTH: 10
<212> TYPE: PRT
<213> ORGANISM: Artificial Sequence
<220> FEATURE:
<223> OTHER INFORMATION: a peptide derived from TOPK

<400> SEQUENCE: 28

Ser Tyr Gln Lys Val Ile Glu Leu Phe Ser
1               5                   10

<210> SEQ ID NO 29
<211> LENGTH: 10
<212> TYPE: PRT
<213> ORGANISM: Artificial Sequence
<220> FEATURE:
<223> OTHER INFORMATION: a peptide derived from TOPK

<400> SEQUENCE: 29

Arg Tyr Lys Ala Ser Gln Asp Pro Phe Pro
1               5                   10
```

<210> SEQ ID NO 30
<211> LENGTH: 10
<212> TYPE: PRT
<213> ORGANISM: Artificial Sequence
<220> FEATURE:
<223> OTHER INFORMATION: a peptide derived from TOPK

<400> SEQUENCE: 30

Tyr Leu Met Lys Arg Ser Pro Arg Gly Leu
1               5                   10

<210> SEQ ID NO 31
<211> LENGTH: 10
<212> TYPE: PRT
<213> ORGANISM: Artificial Sequence
<220> FEATURE:
<223> OTHER INFORMATION: a peptide derived from TOPK

<400> SEQUENCE: 31

His Tyr Arg Ser Val Tyr Gln Lys Arg Leu
1               5                   10

<210> SEQ ID NO 32
<211> LENGTH: 10
<212> TYPE: PRT
<213> ORGANISM: Artificial Sequence
<220> FEATURE:
<223> OTHER INFORMATION: a peptide derived from TOPK

<400> SEQUENCE: 32

Ala Phe Thr Glu Ala Asn Asp Gly Ser Leu
1               5                   10

<210> SEQ ID NO 33
<211> LENGTH: 10
<212> TYPE: PRT
<213> ORGANISM: Artificial Sequence
<220> FEATURE:
<223> OTHER INFORMATION: a peptide derived from TOPK

<400> SEQUENCE: 33

Gly Phe Gly Thr Gly Val Asn Val Tyr Leu
1               5                   10

<210> SEQ ID NO 34
<211> LENGTH: 10
<212> TYPE: PRT
<213> ORGANISM: Artificial Sequence
<220> FEATURE:
<223> OTHER INFORMATION: a peptide derived from TOPK

<400> SEQUENCE: 34

Ile Ser Asn Phe Lys Thr Pro Ser Lys Leu
1               5                   10

<210> SEQ ID NO 35
<211> LENGTH: 10
<212> TYPE: PRT
<213> ORGANISM: Artificial Sequence
<220> FEATURE:
<223> OTHER INFORMATION: a peptide derived from TOPK

<400> SEQUENCE: 35

Val Tyr Gln Lys Arg Leu Met Asp Glu Ala
1               5                   10

<210> SEQ ID NO 36
<211> LENGTH: 10
<212> TYPE: PRT
<213> ORGANISM: Artificial Sequence
<220> FEATURE:
<223> OTHER INFORMATION: a peptide derived from TOPK

<400> SEQUENCE: 36

Met Thr Leu Ser Ile Pro His Ile Asn Leu
1               5                   10

<210> SEQ ID NO 37
<211> LENGTH: 10
<212> TYPE: PRT
<213> ORGANISM: Artificial Sequence
<220> FEATURE:
<223> OTHER INFORMATION: a peptide derived from TOPK

<400> SEQUENCE: 37

Lys Leu Ser Glu Lys Lys Lys Ser Val Leu
1               5                   10

<210> SEQ ID NO 38
<211> LENGTH: 10
<212> TYPE: PRT
<213> ORGANISM: Artificial Sequence
<220> FEATURE:
<223> OTHER INFORMATION: a peptide derived from TOPK

<400> SEQUENCE: 38

Leu Asn Met Ala Arg Gly Leu Lys Tyr Leu
1               5                   10

<210> SEQ ID NO 39
<211> LENGTH: 10
<212> TYPE: PRT
<213> ORGANISM: Artificial Sequence
<220> FEATURE:
<223> OTHER INFORMATION: a peptide derived from TOPK

<400> SEQUENCE: 39

Lys Val Ala Leu Asn Met Ala Arg Gly Leu
1               5                   10

<210> SEQ ID NO 40
<211> LENGTH: 10
<212> TYPE: PRT
<213> ORGANISM: Artificial Sequence
<220> FEATURE:
<223> OTHER INFORMATION: a peptide derived from TOPK

<400> SEQUENCE: 40

Ala Met Glu Tyr Gly Gly Glu Lys Ser Leu
1               5                   10

<210> SEQ ID NO 41
<211> LENGTH: 9
<212> TYPE: PRT
<213> ORGANISM: Artificial Sequence
<220> FEATURE:
<223> OTHER INFORMATION: a peptide derived from TOPK

<400> SEQUENCE: 41

Gly Leu Ser His Ser Pro Trp Ala Val
1               5

-continued

```
<210> SEQ ID NO 42
<211> LENGTH: 9
<212> TYPE: PRT
<213> ORGANISM: Artificial Sequence
<220> FEATURE:
<223> OTHER INFORMATION: a peptide derived from TOPK

<400> SEQUENCE: 42

Met Met Thr Leu Ser Ile Pro His Ile
1               5

<210> SEQ ID NO 43
<211> LENGTH: 9
<212> TYPE: PRT
<213> ORGANISM: Artificial Sequence
<220> FEATURE:
<223> OTHER INFORMATION: a peptide derived from TOPK

<400> SEQUENCE: 43

Phe Met Gln Lys Leu Gly Phe Gly Thr
1               5

<210> SEQ ID NO 44
<211> LENGTH: 9
<212> TYPE: PRT
<213> ORGANISM: Artificial Sequence
<220> FEATURE:
<223> OTHER INFORMATION: a peptide derived from TOPK

<400> SEQUENCE: 44

Thr Leu Trp Glu Met Met Thr Leu Ser
1               5

<210> SEQ ID NO 45
<211> LENGTH: 9
<212> TYPE: PRT
<213> ORGANISM: Artificial Sequence
<220> FEATURE:
<223> OTHER INFORMATION: a peptide derived from TOPK

<400> SEQUENCE: 45

Ser Val Leu Cys Ser Thr Pro Thr Ile
1               5

<210> SEQ ID NO 46
<211> LENGTH: 9
<212> TYPE: PRT
<213> ORGANISM: Artificial Sequence
<220> FEATURE:
<223> OTHER INFORMATION: a peptide derived from TOPK

<400> SEQUENCE: 46

Ser Gln Asp Pro Phe Pro Ala Ala Ile
1               5

<210> SEQ ID NO 47
<211> LENGTH: 9
<212> TYPE: PRT
<213> ORGANISM: Artificial Sequence
<220> FEATURE:
<223> OTHER INFORMATION: a peptide derived from TOPK

<400> SEQUENCE: 47

Lys Ile Cys Asp Val Gly Val Ser Leu
1               5

<210> SEQ ID NO 48
```

```
<211> LENGTH: 9
<212> TYPE: PRT
<213> ORGANISM: Artificial Sequence
<220> FEATURE:
<223> OTHER INFORMATION: a peptide derived from TOPK

<400> SEQUENCE: 48

Arg Leu Met Asp Glu Ala Lys Ile Leu
1               5

<210> SEQ ID NO 49
<211> LENGTH: 9
<212> TYPE: PRT
<213> ORGANISM: Artificial Sequence
<220> FEATURE:
<223> OTHER INFORMATION: a peptide derived from TOPK

<400> SEQUENCE: 49

Asn Met Ala Arg Gly Leu Lys Tyr Leu
1               5

<210> SEQ ID NO 50
<211> LENGTH: 9
<212> TYPE: PRT
<213> ORGANISM: Artificial Sequence
<220> FEATURE:
<223> OTHER INFORMATION: a peptide derived from TOPK

<400> SEQUENCE: 50

Leu Thr Leu Trp Glu Met Met Thr Leu
1               5

<210> SEQ ID NO 51
<211> LENGTH: 9
<212> TYPE: PRT
<213> ORGANISM: Artificial Sequence
<220> FEATURE:
<223> OTHER INFORMATION: a peptide derived from TOPK

<400> SEQUENCE: 51

Lys Leu Ser Glu Lys Lys Lys Ser Val
1               5

<210> SEQ ID NO 52
<211> LENGTH: 9
<212> TYPE: PRT
<213> ORGANISM: Artificial Sequence
<220> FEATURE:
<223> OTHER INFORMATION: a peptide derived from TOPK

<400> SEQUENCE: 52

Lys Ala Asp Ile Phe Ala Phe Gly Leu
1               5

<210> SEQ ID NO 53
<211> LENGTH: 9
<212> TYPE: PRT
<213> ORGANISM: Artificial Sequence
<220> FEATURE:
<223> OTHER INFORMATION: a peptide derived from TOPK

<400> SEQUENCE: 53

Glu Leu Asp Glu Ser Tyr Gln Lys Val
1               5

<210> SEQ ID NO 54
<211> LENGTH: 9
```

```
<212> TYPE: PRT
<213> ORGANISM: Artificial Sequence
<220> FEATURE:
<223> OTHER INFORMATION: a peptide derived from TOPK

<400> SEQUENCE: 54

Tyr Leu Met Lys Arg Ser Pro Arg Gly
1               5

<210> SEQ ID NO 55
<211> LENGTH: 9
<212> TYPE: PRT
<213> ORGANISM: Artificial Sequence
<220> FEATURE:
<223> OTHER INFORMATION: a peptide derived from TOPK

<400> SEQUENCE: 55

Ser Ala Ala His Ile Val Glu Ala Leu
1               5

<210> SEQ ID NO 56
<211> LENGTH: 9
<212> TYPE: PRT
<213> ORGANISM: Artificial Sequence
<220> FEATURE:
<223> OTHER INFORMATION: a peptide derived from TOPK

<400> SEQUENCE: 56

Lys Ala Ser Gln Asp Pro Phe Pro Ala
1               5

<210> SEQ ID NO 57
<211> LENGTH: 9
<212> TYPE: PRT
<213> ORGANISM: Artificial Sequence
<220> FEATURE:
<223> OTHER INFORMATION: a peptide derived from TOPK

<400> SEQUENCE: 57

Thr Leu Ser Ile Pro His Ile Asn Leu
1               5

<210> SEQ ID NO 58
<211> LENGTH: 9
<212> TYPE: PRT
<213> ORGANISM: Artificial Sequence
<220> FEATURE:
<223> OTHER INFORMATION: a peptide derived from TOPK

<400> SEQUENCE: 58

Tyr Leu His Gln Glu Lys Lys Leu Leu
1               5

<210> SEQ ID NO 59
<211> LENGTH: 9
<212> TYPE: PRT
<213> ORGANISM: Artificial Sequence
<220> FEATURE:
<223> OTHER INFORMATION: a peptide derived from TOPK

<400> SEQUENCE: 59

Phe Pro Ala Ala Ile Ile Leu Lys Val
1               5

<210> SEQ ID NO 60
<211> LENGTH: 9
<212> TYPE: PRT
```

<213> ORGANISM: Artificial Sequence
<220> FEATURE:
<223> OTHER INFORMATION: a peptide derived from TOPK

<400> SEQUENCE: 60

Ile Ile Leu Lys Val Ala Leu Asn Met
1               5

<210> SEQ ID NO 61
<211> LENGTH: 10
<212> TYPE: PRT
<213> ORGANISM: Artificial Sequence
<220> FEATURE:
<223> OTHER INFORMATION: a peptide derived from TOPK

<400> SEQUENCE: 61

Ser Leu Pro Leu Asp Glu Asn Met Thr Val
1               5                   10

<210> SEQ ID NO 62
<211> LENGTH: 10
<212> TYPE: PRT
<213> ORGANISM: Artificial Sequence
<220> FEATURE:
<223> OTHER INFORMATION: a peptide derived from TOPK

<400> SEQUENCE: 62

Thr Leu Trp Glu Met Met Thr Leu Ser Ile
1               5                   10

<210> SEQ ID NO 63
<211> LENGTH: 10
<212> TYPE: PRT
<213> ORGANISM: Artificial Sequence
<220> FEATURE:
<223> OTHER INFORMATION: a peptide derived from TOPK

<400> SEQUENCE: 63

Phe Ala Phe Gly Leu Thr Leu Trp Glu Met
1               5                   10

<210> SEQ ID NO 64
<211> LENGTH: 10
<212> TYPE: PRT
<213> ORGANISM: Artificial Sequence
<220> FEATURE:
<223> OTHER INFORMATION: a peptide derived from TOPK

<400> SEQUENCE: 64

Tyr Leu Met Lys Arg Ser Pro Arg Gly Leu
1               5                   10

<210> SEQ ID NO 65
<211> LENGTH: 10
<212> TYPE: PRT
<213> ORGANISM: Artificial Sequence
<220> FEATURE:
<223> OTHER INFORMATION: a peptide derived from TOPK

<400> SEQUENCE: 65

Gly Leu Thr Leu Trp Glu Met Met Thr Leu
1               5                   10

<210> SEQ ID NO 66
<211> LENGTH: 10
<212> TYPE: PRT
<213> ORGANISM: Artificial Sequence

```
<220> FEATURE:
<223> OTHER INFORMATION: a peptide derived from TOPK

<400> SEQUENCE: 66

Glu Met Met Thr Leu Ser Ile Pro His Ile
1               5                   10

<210> SEQ ID NO 67
<211> LENGTH: 10
<212> TYPE: PRT
<213> ORGANISM: Artificial Sequence
<220> FEATURE:
<223> OTHER INFORMATION: a peptide derived from TOPK

<400> SEQUENCE: 67

Tyr Gln Lys Val Ile Glu Leu Phe Ser Val
1               5                   10

<210> SEQ ID NO 68
<211> LENGTH: 10
<212> TYPE: PRT
<213> ORGANISM: Artificial Sequence
<220> FEATURE:
<223> OTHER INFORMATION: a peptide derived from TOPK

<400> SEQUENCE: 68

Lys Leu Gly Phe Gly Thr Gly Val Asn Val
1               5                   10

<210> SEQ ID NO 69
<211> LENGTH: 10
<212> TYPE: PRT
<213> ORGANISM: Artificial Sequence
<220> FEATURE:
<223> OTHER INFORMATION: a peptide derived from TOPK

<400> SEQUENCE: 69

Val Leu Cys Ser Thr Pro Thr Ile Asn Ile
1               5                   10

<210> SEQ ID NO 70
<211> LENGTH: 10
<212> TYPE: PRT
<213> ORGANISM: Artificial Sequence
<220> FEATURE:
<223> OTHER INFORMATION: a peptide derived from TOPK

<400> SEQUENCE: 70

Met Thr Leu Ser Ile Pro His Ile Asn Leu
1               5                   10

<210> SEQ ID NO 71
<211> LENGTH: 10
<212> TYPE: PRT
<213> ORGANISM: Artificial Sequence
<220> FEATURE:
<223> OTHER INFORMATION: a peptide derived from TOPK

<400> SEQUENCE: 71

Tyr Ala Ala Leu Gly Thr Arg Pro Pro Ile
1               5                   10

<210> SEQ ID NO 72
<211> LENGTH: 10
<212> TYPE: PRT
<213> ORGANISM: Artificial Sequence
<220> FEATURE:
```

```
<223> OTHER INFORMATION: a peptide derived from TOPK

<400> SEQUENCE: 72

Ile Leu Lys Ser Leu His His Pro Asn Ile
1               5                   10

<210> SEQ ID NO 73
<211> LENGTH: 10
<212> TYPE: PRT
<213> ORGANISM: Artificial Sequence
<220> FEATURE:
<223> OTHER INFORMATION: a peptide derived from TOPK

<400> SEQUENCE: 73

Arg Leu Met Asp Glu Ala Lys Ile Leu Lys
1               5                   10

<210> SEQ ID NO 74
<211> LENGTH: 10
<212> TYPE: PRT
<213> ORGANISM: Artificial Sequence
<220> FEATURE:
<223> OTHER INFORMATION: a peptide derived from TOPK

<400> SEQUENCE: 74

His Ile Val Glu Ala Leu Glu Thr Asp Val
1               5                   10

<210> SEQ ID NO 75
<211> LENGTH: 10
<212> TYPE: PRT
<213> ORGANISM: Artificial Sequence
<220> FEATURE:
<223> OTHER INFORMATION: a peptide derived from TOPK

<400> SEQUENCE: 75

Arg Gly Leu Ser His Ser Pro Trp Ala Val
1               5                   10

<210> SEQ ID NO 76
<211> LENGTH: 10
<212> TYPE: PRT
<213> ORGANISM: Artificial Sequence
<220> FEATURE:
<223> OTHER INFORMATION: a peptide derived from TOPK

<400> SEQUENCE: 76

Ile Ile Leu Lys Val Ala Leu Asn Met Ala
1               5                   10

<210> SEQ ID NO 77
<211> LENGTH: 10
<212> TYPE: PRT
<213> ORGANISM: Artificial Sequence
<220> FEATURE:
<223> OTHER INFORMATION: a peptide derived from TOPK

<400> SEQUENCE: 77

Met Gln Lys Leu Gly Phe Gly Thr Gly Val
1               5                   10

<210> SEQ ID NO 78
<211> LENGTH: 10
<212> TYPE: PRT
<213> ORGANISM: Artificial Sequence
<220> FEATURE:
<223> OTHER INFORMATION: a peptide derived from TOPK
```

```
<400> SEQUENCE: 78

Ser Leu Cys Leu Ala Met Glu Tyr Gly Gly
1               5                   10

<210> SEQ ID NO 79
<211> LENGTH: 10
<212> TYPE: PRT
<213> ORGANISM: Artificial Sequence
<220> FEATURE:
<223> OTHER INFORMATION: a peptide derived from TOPK

<400> SEQUENCE: 79

Val Ile Thr Asp Lys Ala Asp Ile Phe Ala
1               5                   10

<210> SEQ ID NO 80
<211> LENGTH: 10
<212> TYPE: PRT
<213> ORGANISM: Artificial Sequence
<220> FEATURE:
<223> OTHER INFORMATION: a peptide derived from TOPK

<400> SEQUENCE: 80

Ala Leu Gly Thr Arg Pro Pro Ile Asn Met
1               5                   10

<210> SEQ ID NO 81
<211> LENGTH: 10
<212> TYPE: PRT
<213> ORGANISM: Artificial Sequence
<220> FEATURE:
<223> OTHER INFORMATION: a peptide derived from TOPK

<400> SEQUENCE: 81

Val Val Ile Lys Gly Asp Phe Glu Thr Ile
1               5                   10

<210> SEQ ID NO 82
<211> LENGTH: 10
<212> TYPE: PRT
<213> ORGANISM: Artificial Sequence
<220> FEATURE:
<223> OTHER INFORMATION: a peptide derived from TOPK

<400> SEQUENCE: 82

Ala Ile Ile Leu Lys Val Ala Leu Asn Met
1               5                   10

<210> SEQ ID NO 83
<211> LENGTH: 10
<212> TYPE: PRT
<213> ORGANISM: Artificial Sequence
<220> FEATURE:
<223> OTHER INFORMATION: a peptide derived from TOPK

<400> SEQUENCE: 83

Lys Val Ile Glu Leu Phe Ser Val Cys Thr
1               5                   10

<210> SEQ ID NO 84
<211> LENGTH: 10
<212> TYPE: PRT
<213> ORGANISM: Artificial Sequence
<220> FEATURE:
<223> OTHER INFORMATION: a peptide derived from TOPK
```

<400> SEQUENCE: 84

Glu Thr Ile Lys Ile Cys Asp Val Gly Val
1               5                   10

<210> SEQ ID NO 85
<211> LENGTH: 1899
<212> TYPE: DNA
<213> ORGANISM: Homo sapiens
<220> FEATURE:
<221> NAME/KEY: CDS
<222> LOCATION: (202)..(1170)

<400> SEQUENCE: 85

```
agcgcgcgac tttttgaaag ccaggagggt tcgaattgca acggcagctg ccgggcgtat      60
gtgttggtgc tagaggcagc tgcagggtct cgctgggggc cgctcgggac caattttgaa     120
gaggtacttg gccacgactt attttcacct ccgacctttc cttccaggcg gtgagactct     180
ggactgagag tggctttcac a atg gaa ggg atc agt aat ttc aag aca cca       231
                         Met Glu Gly Ile Ser Asn Phe Lys Thr Pro
                          1               5                  10 agc aaa tta tca gaa aaa aag aaa tct gta tta tgt tca act cca act       279
Ser Lys Leu Ser Glu Lys Lys Lys Ser Val Leu Cys Ser Thr Pro Thr
             15                  20                  25 ata aat atc ccg gcc tct ccg ttt atg cag aag ctt ggc ttt ggt act       327
Ile Asn Ile Pro Ala Ser Pro Phe Met Gln Lys Leu Gly Phe Gly Thr
         30                  35                  40 ggg gta aat gtg tac cta atg aaa aga tct cca aga ggt ttg tct cat       375
Gly Val Asn Val Tyr Leu Met Lys Arg Ser Pro Arg Gly Leu Ser His
     45                  50                  55 tct cct tgg gct gta aaa aag att aat cct ata tgt aat gat cat tat       423
Ser Pro Trp Ala Val Lys Lys Ile Asn Pro Ile Cys Asn Asp His Tyr
 60                  65                  70 cga agt gtg tat caa aag aga cta atg gat gaa gct aag att ttg aaa       471
Arg Ser Val Tyr Gln Lys Arg Leu Met Asp Glu Ala Lys Ile Leu Lys
75                  80                  85                  90 agc ctt cat cat cca aac att gtt ggt tat cgt gct ttt act gaa gcc       519
Ser Leu His His Pro Asn Ile Val Gly Tyr Arg Ala Phe Thr Glu Ala
                 95                 100                 105 aat gat ggc agt ctg tgt ctt gct atg gaa tat gga ggt gaa aag tct       567
Asn Asp Gly Ser Leu Cys Leu Ala Met Glu Tyr Gly Gly Glu Lys Ser
            110                 115                 120 cta aat gac tta ata gaa gaa cga tat aaa gcc agc caa gat cct ttt       615
Leu Asn Asp Leu Ile Glu Glu Arg Tyr Lys Ala Ser Gln Asp Pro Phe
        125                 130                 135 cca gca gcc ata att tta aaa gtt gct ttg aat atg gca aga ggg tta       663
Pro Ala Ala Ile Ile Leu Lys Val Ala Leu Asn Met Ala Arg Gly Leu
    140                 145                 150 aag tat ctg cac caa gaa aag aaa ctg ctt cat gga gac ata aag tct       711
Lys Tyr Leu His Gln Glu Lys Lys Leu Leu His Gly Asp Ile Lys Ser
155                 160                 165                 170 tca aat gtt gta att aaa ggc gat ttt gaa aca att aaa tct tgt gat       759
Ser Asn Val Val Ile Lys Gly Asp Phe Glu Thr Ile Lys Ile Cys Asp
                175                 180                 185 gta gga gtc tct cta cca ctg gat gaa aat atg act gtg act gac cct       807
Val Gly Val Ser Leu Pro Leu Asp Glu Asn Met Thr Val Thr Asp Pro
            190                 195                 200 gag gct tgt tac att ggc aca gag cca tgg aaa ccc aaa gaa gct gtg       855
Glu Ala Cys Tyr Ile Gly Thr Glu Pro Trp Lys Pro Lys Glu Ala Val
        205                 210                 215 gag gag aat ggt gtt att act gac aag gca gac ata ttt gcc ttt ggc       903
```

```
                    Glu Glu Asn Gly Val Ile Thr Asp Lys Ala Asp Ile Phe Ala Phe Gly
                        220                 225                 230 ctt act ttg tgg gaa atg atg act tta tcg att cca cac att aat ctt      951
Leu Thr Leu Trp Glu Met Met Thr Leu Ser Ile Pro His Ile Asn Leu
235                 240                 245                 250 tca aat gat gat gat gat gaa gat aaa act ttt gat gaa agt gat ttt      999
Ser Asn Asp Asp Asp Asp Glu Asp Lys Thr Phe Asp Glu Ser Asp Phe
                        255                 260                 265 gat gat gaa gca tac tat gca gcg ttg gga act agg cca cct att aat     1047
Asp Asp Glu Ala Tyr Tyr Ala Ala Leu Gly Thr Arg Pro Pro Ile Asn
                270                 275                 280 atg gaa gaa ctg gat gaa tca tac cag aaa gta att gaa ctc ttc tct     1095
Met Glu Glu Leu Asp Glu Ser Tyr Gln Lys Val Ile Glu Leu Phe Ser
            285                 290                 295 gta tgc act aat gaa gac cct aaa gat cgt cct tct gct gca cac att     1143
Val Cys Thr Asn Glu Asp Pro Lys Asp Arg Pro Ser Ala Ala His Ile
        300                 305                 310 gtt gaa gct ctg gaa aca gat gtc tag tgatcatctc agctgaagtg           1190
Val Glu Ala Leu Glu Thr Asp Val
315                 320 tggcttgcgt aaataactgt ttattccaaa atatttacat agttactatc agtagttatt   1250
agactctaaa attggcatat ttgaggacca tagtttcttg ttaacatatg gataactatt   1310
tctaatatga aatatgctta tattggctat aagcacttgg aattgtactg ggttttctgt   1370
aaagttttag aaactagcta cataagtact ttgatactgc tcatgctgac ttaaaacact   1430
agcagtaaaa cgctgtaaac tgtaacatta aattgaatga ccattacttt tattaatgat   1490
ctttcttaaa tattctatat tttaatggat ctactgacat tagcactttg tacagtacaa   1550
aataaagtct acatttgttt aaaacactga acctttgct gatgtgttta tcaaatgata    1610
actggaagct gaggagaata tgcctcaaaa agagtagctc cttggatact tcagactctg   1670
gttacagatt gtcttgatct cttggatctc ctcagatctt tggttttgc tttaatttat    1730 taaatgtatt ttccatactg agtttaaaat ttattaattt gtaccttaag catttcccag   1790
ctgtgtaaaa acaataaaac tcaaatagga tgataaagaa taaaggacac tttgggtacc   1850
agaaaaaaaa aaaaaaaaa aaaaaaaaa aaaaaaaaa                            1899

<210> SEQ ID NO 86
<211> LENGTH: 322
<212> TYPE: PRT
<213> ORGANISM: Homo sapiens

<400> SEQUENCE: 86

Met Glu Gly Ile Ser Asn Phe Lys Thr Pro Ser Lys Leu Ser Glu Lys
1               5                   10                  15

Lys Lys Ser Val Leu Cys Ser Thr Pro Thr Ile Asn Ile Pro Ala Ser
            20                  25                  30

Pro Phe Met Gln Lys Leu Gly Phe Gly Thr Gly Val Asn Val Tyr Leu
        35                  40                  45

Met Lys Arg Ser Pro Arg Gly Leu Ser His Ser Pro Trp Ala Val Lys
    50                  55                  60

Lys Ile Asn Pro Ile Cys Asn Asp His Tyr Arg Ser Val Tyr Gln Lys
65                  70                  75                  80

Arg Leu Met Asp Glu Ala Lys Ile Leu Lys Ser Leu His His Pro Asn
                85                  90                  95

Ile Val Gly Tyr Arg Ala Phe Thr Glu Ala Asn Asp Gly Ser Leu Cys
            100                 105                 110
```

```
Leu Ala Met Glu Tyr Gly Gly Glu Lys Ser Leu Asn Asp Leu Ile Glu
        115                 120                 125

Glu Arg Tyr Lys Ala Ser Gln Asp Pro Phe Pro Ala Ile Ile Leu
    130                 135                 140

Lys Val Ala Leu Asn Met Ala Arg Gly Leu Lys Tyr Leu His Gln Glu
145                 150                 155                 160

Lys Lys Leu Leu His Gly Asp Ile Lys Ser Ser Asn Val Val Ile Lys
                165                 170                 175

Gly Asp Phe Glu Thr Ile Lys Ile Cys Asp Val Gly Val Ser Leu Pro
                180                 185                 190

Leu Asp Glu Asn Met Thr Val Thr Asp Pro Glu Ala Cys Tyr Ile Gly
            195                 200                 205

Thr Glu Pro Trp Lys Pro Lys Glu Ala Val Glu Glu Asn Gly Val Ile
    210                 215                 220

Thr Asp Lys Ala Asp Ile Phe Ala Phe Gly Leu Thr Leu Trp Glu Met
225                 230                 235                 240

Met Thr Leu Ser Ile Pro His Ile Asn Leu Ser Asn Asp Asp Asp Asp
                245                 250                 255

Glu Asp Lys Thr Phe Asp Glu Ser Asp Phe Asp Glu Ala Tyr Tyr
            260                 265                 270

Ala Ala Leu Gly Thr Arg Pro Pro Ile Asn Met Glu Glu Leu Asp Glu
        275                 280                 285

Ser Tyr Gln Lys Val Ile Glu Leu Phe Ser Val Cys Thr Asn Glu Asp
    290                 295                 300

Pro Lys Asp Arg Pro Ser Ala Ala His Ile Val Glu Ala Leu Glu Thr
305                 310                 315                 320

Asp Val

<210> SEQ ID NO 87
<211> LENGTH: 22
<212> TYPE: DNA
<213> ORGANISM: Artificial Sequence
<220> FEATURE:
<223> OTHER INFORMATION: a PCR primer for the TCR analysis

<400> SEQUENCE: 87
gtctaccagg cattcgcttc at                                         22

<210> SEQ ID NO 88
<211> LENGTH: 24
<212> TYPE: DNA
<213> ORGANISM: Artificial Sequence
<220> FEATURE:
<223> OTHER INFORMATION: a PCR primer for the TCR analysis

<400> SEQUENCE: 88
tcagctggac cacagccgca gcgt                                       24

<210> SEQ ID NO 89
<211> LENGTH: 21
<212> TYPE: DNA
<213> ORGANISM: Artificial Sequence
<220> FEATURE:
<223> OTHER INFORMATION: a PCR primer for the TCR analysis

<400> SEQUENCE: 89
tcagaaatcc tttctcttga c                                          21
```

```
<210> SEQ ID NO 90
<211> LENGTH: 24
<212> TYPE: DNA
<213> ORGANISM: Artificial Sequence
<220> FEATURE:
<223> OTHER INFORMATION: a PCR primer for the TCR analysis

<400> SEQUENCE: 90
ctagcctctg gaatcctttc tctt                                              24
```

TOPK PEPTIDES AND VACCINES INCLUDING THE SAME

PRIORITY

The present application is a U.S. National Phase of PCT/JP2012/006853, filed Oct. 25, 2012, which claims the benefit of U.S. Provisional Applications No. 61/552,817, filed on Oct. 28, 2011, the entire contents of which are incorporated by reference herein in their entirety.

TECHNICAL FIELD

The present invention relates to the field of biological science, more specifically to the field of cancer therapy. In particular, the present invention relates to novel peptides that are effective as cancer vaccines, and drugs for either or both of treating and preventing tumors.

REFERENCE TO SEQUENCE LISTING

This application includes a Sequence Listing as a text file named "87331-0272100US-903761-SEQLIST.txt" created Mar. 13, 2014, and containing 27,292 bytes. The material contained in this text file is incorporated by reference in its entirety for all purposes.

BACKGROUND ART

CD8 positive cytotoxic T lymphocytes (CTLs) have been shown to recognize epitope peptides derived from tumor-associated antigens (TAAs) on the major histocompatibility complex (MHC) class I molecule, and then kill the tumor cells. Since the discovery of the melanoma antigen (MAGE) family as the first example of TAAs, many other TAAs have been discovered through immunological approaches (NPL 1, 2), and some of the TAAs are now in the process of clinical development as immunotherapeutic targets.

Favorable TAAs are indispensable for the proliferation and survival of cancer cells. The use of such TAAs as targets for immunotherapy may minimize the well-described risk of immune escape of cancer cells attributable to deletion, mutation, and/or down-regulation of TAAs as a consequence of therapeutically driven immune selection. Accordingly, the identification of new TAAs capable of inducing potent and specific anti-tumor immune responses warrants further development. Thus, clinical application of peptide vaccination strategies in various types of cancer is ongoing (NPL 3-10). To date, there have been several reports of clinical trials using these TAAs-derived peptides. Unfortunately, so far, these cancer vaccine trials have yielded only a low objective response rate (NPL 11-13). Accordingly, there remains a need in the art for new TAAs suitable for use as immunotherapeutic targets.

TOPK (T-LAK cell-originated protein kinase) is a serine/threonine kinase that is member of the MAPK kinase (MAPKK) 3/6-related MAPKK family. This kinase phosphorylates p38 MAPK and participate in the regulation of cell cycle check point (NPL 14, 15). Gene expression analysis of TOPK using clinical samples indicated that TOPK is overexpressed in some malignant cancer, such as breast cancer, cholangio-carcinoma, hepatocellular carcinoma, leukemia, colorectal cancer and melanoma (NPL 16-19). Recent studies indicating that kinase activity plays an important role in breast carcinogenesis has renewed research interest in cancer-linked kinases such as TOPK. To that end, Northern blot analysis has revealed that TOPK transcript is highly expressed in breast cancer cells but is hardly detectable in normal human tissues except testis. In addition, knockdown of endogenous TOPK expression by siRNA in breast cancer cell lines has been shown to attenuate the cytokinesis and lead to apoptosis of the cancer cells (NPL 20).

CITATION LIST

Non Patent Literature

[NPL 1] Boon T, Int J Cancer 1993 May 8, 54(2): 177-80
[NPL 2] Boon T & van der Bruggen P, J Exp Med 1996 Mar. 1, 183(3): 725-9
[NPL 3] Harris C C, J Natl Cancer Inst 1996 Oct. 16, 88(20): 1442-55
[NPL 4] Butterfield L H et al., Cancer Res 1999 Jul. 1, 59(13): 3134-42
[NPL 5] Vissers J L et al., Cancer Res 1999 Nov. 1, 59(21): 5554-9
[NPL 6] van der Burg S H et al., J Immunol 1996 May 1, 156(9): 3308-14
[NPL 7] Tanaka F et al., Cancer Res 1997 Oct. 15, 57(20): 4465-8
[NPL 8] Fujie T et al., Int J Cancer 1999 Jan. 18, 80(2): 169-72
[NPL 9] Kikuchi M et al., Int J Cancer 1999 May 5, 81(3): 459-66
[NPL 10] Oiso M et al., Int J Cancer 1999 May 5, 81(3): 387-94
[NPL 11] Belli F et al., J Clin Oncol 2002 Oct. 15, 20(20): 4169-80
[NPL 12] Coulie P G et al., Immunol Rev 2002 October, 188: 33-42
[NPL 13] Rosenberg S A et al., Nat Med 2004 September, 10(9): 909-15
[NPL 14] Abe Y et. al., J Bio Chem. 2000 Jul. 14: 21525-21531
[NPL 15] Ayllon V and O'connor R., Oncogene. 2007 May 24; 26(24):3451-61
[NPL 16] He F et al., Hum Pathol. 2010 March; 41(3):415-24
[NPL 17] Li G et al., Ann Hematol. 2006 September; 85(9):583-90
[NPL 18] Minoo P et al., Int J. Oncol. 2010 September; 37(3):707-18
[NPL 19] Zykova T A et al., Clin Cancer Res. 2006 Dec. 1; 12(23):6884-93
[NPL 20] Park J H et al., Cancer Res. 2006 Sep. 15; 66(18):9186-95

SUMMARY OF INVENTION

The present invention is based, at least in part, on the discovery of novel peptides that may serve as suitable targets of immunotherapy. Because TAAs are generally perceived by the immune system as "self" and therefore often have no innate immunogenicity, the discovery of appropriate targets is of extreme importance. Through the present invention, TOPK (SEQ ID NO: 86 encoded by the gene of GenBank Accession No. NM_018492 (SEQ ID NO: 85)) is demonstrated to be specifically over-expressed in cancer cells, in particular acute myeloid leukemia (AML), bladder cancer, breast cancer, cervical cancer, cholangiocellular carcinoma, colorectal cancer, diffuse-type gastric cancer, non-small cell lung cancer (NSCLC), lymphoma, osteosarcoma, prostate cancer, renal carcinoma, small cell lung cancer (SCLC) and soft tissue tumor, but not limited thereto. Thus, the present invention focuses on TOPK as an appropriate candidate target of cancer/tumor immunotherapy.

To that end, the present invention is directed, at least in part, to the identification of specific epitope peptides among the gene products of TOPK that possess the ability to induce cytotoxic T lymphocytes (CTLs) specific to TOPK. As discussed in greater detail below, peripheral blood mononuclear cells (PBMCs) obtained from a healthy donor were stimulated using HLA (human leukocyte antigen)-A*2402 or HLA-A*0201 binding candidate peptides derived from TOPK. CTL lines were then established with specific cytotoxicity against the HLA-A24 or HLA-A2 positive target cells pulsed with each of candidate peptides. The results herein demonstrate that these peptides are HLA-A24 or HLA-A2 restricted epitope peptides that can induce potent and specific immune responses against cells expressing TOPK. These results further indicate that TOPK is strongly immunogenic and that the epitopes thereof are effective targets for tumor immunotherapy.

Accordingly, it is an object of the present invention is to provide isolated peptides that have an ability to bind an HLA antigen and include the TOPK sequence (SEQ ID NO: 86) or an immunogenically active fragment thereof. These peptides are expected to have CTL inducibility and, thus, can be used to induce a CTL in vitro, ex vivo or in vivo or to be administered directly to a subject so as to induce in vivo immune responses against cancers, examples of which include, but are not limited to, AML, bladder cancer, breast cancer, cervical cancer, cholangiocellular carcinoma, colorectal cancer, diffuse-type gastric cancer, NSCLC, lymphoma, osteosarcoma, prostate cancer, renal carcinoma, SCLC and soft tissue tumor.

Preferred peptides are nonapeptides and decapeptides, and more preferably nonapeptides and decapeptides having an amino acid sequence selected from among SEQ ID NOs: 2 to 40 and 42 to 84. Of these, the peptides having an amino sequence selected from among SEQ ID NOs: 2, 3, 6, 27, 28, 42, 45, 47, 50, 51, 53, 54, 62, 63, 64, 66, 71, 72 and 76 are most preferred.

The present invention also contemplates modified peptides having an amino acid sequence selected from among SEQ ID NOs: 2 to 40 and 42 to 84 in which one, two or more amino acids are substituted, deleted, inserted and/or added, provided the resulting modified peptides retain the requisite CTL inducibility of the original unmodified peptide.

The present invention further encompasses isolated polynucleotides encoding any one of peptides of the present invention. These polynucleotides can be used to induce or prepare antigen-presenting cells (APCs) having CTL inducibility. Like the above-described peptides of the present invention, such APCs can be administered to a subject for inducing immune responses against cancers.

When administered to a subject, the peptides of the present invention are preferably presented on the surface of APCs so as to induce CTLs targeting the respective peptides. Therefore, one object of the present invention is to provide agents or compositions for inducing a CTL, such compositions or agents including one or more peptides of the present invention, or one or more polynucleotides encoding such peptides. Such agents or compositions can be used for the treatment and/or prophylaxis of a primary cancer, a metastasis or post-operative recurrence thereof. Examples of targeted cancers contemplated by the present invention include, but are not limited to, AML, bladder cancer, breast cancer, cervical cancer, cholangiocellular carcinoma, colorectal cancer, diffuse-type gastric cancer, NSCLC, lymphoma, osteosarcoma, prostate cancer, renal carcinoma, SCLC and soft tissue tumor.

The present invention further contemplates pharmaceutical compositions or agents that include one or more peptides or one or more polynucleotides of the present invention formulated for the treatment and/or prophylaxis of a primary cancer, metastasis or postoperative recurrence cancer as noted above. Instead of or in addition to the present peptides or polynucleotides, the present pharmaceutical agents or compositions may include as active ingredients APCs and/or exosomes that present any of the peptides of the present invention.

The peptides or polynucleotides of the present invention may be used to induce APCs that present on the surface a complex of an HLA antigen and a peptide of the present invention, for example, by contacting APCs derived from a subject with the peptide of the present invention or introducing a polynucleotide encoding the peptide of the present invention into APCs. Such APCs have high CTL inducibility against target peptides and are useful for cancer immunotherapy. Accordingly, the present invention encompasses the methods for inducing APCs with CTL inducibility as well as the APCs obtained by the methods.

It is a further object of the present invention to provide methods for inducing CTLs, such methods including the step of co-culturing CD8-positive T cells with APCs presenting on its surface a complex of an HLA antigen and the peptide of the present invention, the step of co-culturing CD8-positive T cells with exosomes presenting on its surface a complex of an HLA antigen and the peptide of the present invention, or the step of introducing a polynucleotide/polynucleotides coding for T cell receptor (TCR) subunit polypeptides wherein the TCR formed by the subunit polypeptides can bind to a peptide of the present invention. CTLs obtained by such methods find use in the treatment and/or prevention of cancers, more particularly AML, bladder cancer, breast cancer, cervical cancer, cholangiocellular carcinoma, colorectal cancer, diffuse-type gastric cancer, NSCLC, lymphoma, osteosarcoma, prostate cancer, renal carcinoma, SCLC and soft tissue tumor. Accordingly, the present invention encompasses the methods for inducing CTLs as well as the CTLs obtained by the methods. Yet another object of the present invention is to provide isolated APCs that present on the surface a complex of an HLA antigen and a peptide of the present invention. The present invention further provides isolated CTLs that target peptides of the present invention. These APCs and CTLs may be used for cancer immunotherapy.

It is yet another object of the present invention to provide methods for inducing an immune response against a cancer in a subject in need thereof, such methods including the step of administering to the subject a composition that includes at least one component selected from among a peptide of the present invention, a polynucleotide encoding such a peptide, exosomes or APCs presenting such peptides, and CTLs that can recognize cells presenting such peptides on their surface.

The applicability of the present invention extends to any of a number of diseases relating to or arising from TOPK overexpression, such as cancers expressing TOPK, examples of which include, but are not limited to, AML, bladder cancer, breast cancer, cervical cancer, cholangiocellular carcinoma, colorectal cancer, diffuse-type gastric cancer, NSCLC, lymphoma, osteosarcoma, prostate cancer, renal carcinoma, SCLC and soft tissue tumor.

Objects and features of the invention will become more fully apparent when the following detailed description is read in conjunction with the accompanying figures and examples. It is to be understood that both the foregoing summary of the present invention and the following detailed description are of exemplified embodiments, and not restrictive of the present invention or other alternate embodiments of the present invention.

In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

BRIEF DESCRIPTION OF DRAWINGS

Various aspects and applications of the present invention will become apparent to the skilled artisan upon consideration of the brief description of the figures and the detailed description of the present invention and its preferred embodiments that follow.

FIG. 2 is composed of a series of photographs, (a)-(o), depicting the results of interferon (IFN)-gamma enzyme-linked immunospot (ELISPOT) assay on CTLs that were induced with peptides derived from TOPK. The CTLs in #4 induced with TOPK-A02-10-88 (SEQ ID NO: 72) (m) and in #4 induced with TOPK-A02-10-142 (SEQ ID NO: 76) (n) showed potent IFN-gamma production as compared with the control, respectively. The square on the well of these pictures indicates that the cells from corresponding well were expanded to establish CTL lines. In contrast, as is typical of negative data, no specific IFN-gamma production was observed from the CTL stimulated with TOPK-A02-9-55 (SEQ ID NO: 41) (o). In the figures, "+" indicates the IFN-gamma production against target cells pulsed with the appropriate peptide, and "−" indicates the IFN-gamma production against target cells not pulsed with any peptides.

FIG. 5-1 is composed of a series of line graphs, (a)-(f), depicting the IFN-gamma production of the CTL lines stimulated with TOPK-A02-9-240 (SEQ ID NO: 42) (a), TOPK-A02-9-19 (SEQ ID NO: 45) (b), TOPK-A02-9-235 (SEQ ID NO: 50) (c), TOPK-A02-9-12 (SEQ ID NO: 51) (d), TOPK-A02-9-285 (SEQ ID NO: 53) (e), and TOPK-A02-9-47 (SEQ ID NO: 54) (f). The quantity of IFN-gamma which CTL produced was measured by IFN-gamma enzyme-linked immunosorbent assay (ELISA). The results demonstrate that CTL lines established by stimulation with each peptide show potent IFN-gamma production as compared with the control. In the figures, "+" indicates the IFN-gamma production against target cells pulsed with the appropriate peptide, and "−" indicates the IFN-gamma production against target cells not pulsed with any peptides. R/S ratio indicates the ratio of the number of responder cells (CTL line) and stimulator cells.

FIG. 5-2 is composed of a series of line graphs, (g)-(k), depicting the IFN-gamma production of the CTL lines stimulated with TOPK-A02-10-236 (SEQ ID NO: 62) (g), TOPK-A02-10-231 (SEQ ID NO: 63) (h), TOPK-A02-10-47 (SEQ ID NO: 64) (i), TOPK-A02-10-239 (SEQ ID NO: 66) (j) and TOPK-A02-10-88 (SEQ ID NO: 72) (k). The quantity of IFN-gamma which CTL produced was measured by IFN-gamma enzyme-linked immunosorbent assay (ELISA). The results demonstrate that CTL lines established by stimulation with each peptide show potent IFN-gamma production as compared with the control. In the figures, "+" indicates the IFN-gamma production against target cells pulsed with the appropriate peptide, and "−" indicates the IFN-gamma production against target cells not pulsed with any peptides. R/S ratio indicates the ratio of the number of responder cells (CTL line) and stimulator cells.

DESCRIPTION OF EMBODIMENTS

Figure 2:
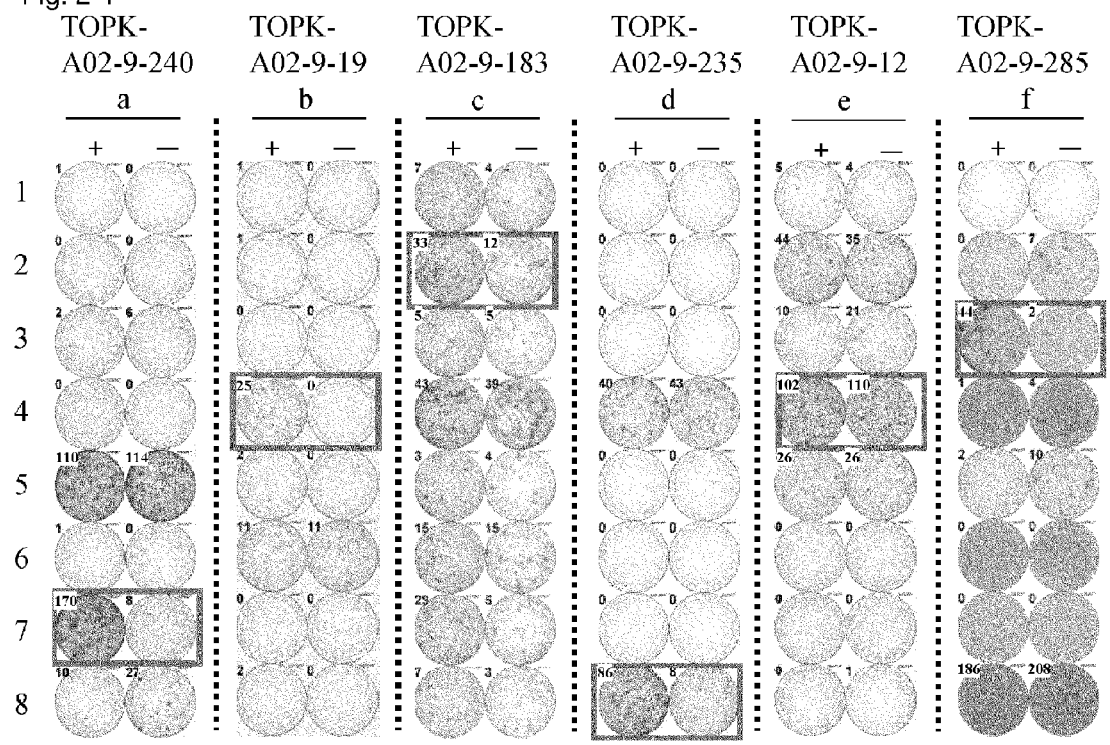
FIG. 2 is composed of a series of photographs, (a)-(o), depicting the results of interferon (IFN)-gamma enzyme-linked immunospot (ELISPOT) assay on CTLs that were induced with peptides derived from TOPK. The CTLs in well number #7 induced with TOPK-A02-9-240 (SEQ ID NO: 42) (a), in #4 induced with TOPK-A02-9-19 (SEQ ID NO: 45) (b), in #2 induced with TOPK-A02-9-183 (SEQ ID NO: 47) (c), in #8 induced with TOPK-A02-9-235 (SEQ ID NO: 50) (d), in #4 induced with TOPK-A02-9-12 (SEQ ID NO: 51) (e), in #3 induced with TOPK-A02-9-285 (SEQ ID NO: 53) (f), in #3 induced with TOPK-A02-9-47 (SEQ ID NO: 54) (g), in #5 induced with TOPK-A02-10-236 (SEQ ID NO: 62) (h), in #3 induced with TOPK-A02-10-231 (SEQ ID NO: 63) (i), in #8 induced with TOPK-A02-10-47 (SEQ ID NO: 64) (j), in #1 induced with TOPK-A02-10-239 (SEQ ID NO: 66) (k), and in #1 induced with TOPK-A02-10-272 (SEQ ID NO: 71) (l) showed potent IFN-gamma production as compared with the control, respectively. The square on the well of these pictures indicates that the cells from corresponding well were expanded to establish CTL lines. In contrast, as is typical of negative data, no specific IFN-gamma production was observed from the CTL stimulated with TOPK-A02-9-55 (SEQ ID NO: 41) (o). In the figures, "+" indicates the IFN-gamma production against target cells pulsed with the appropriate peptide, and "−" indicates the IFN-gamma production against target cells not pulsed with any peptides.

Further to the summary above, it is an object of the present invention to provide:

[1] An isolated peptide having CTL inducibility, wherein the peptide consists of the amino acid sequence of TOPK or an immunologically active fragment thereof.

[2] The isolated peptide of [1], wherein the peptide comprises an amino acid sequence selected from the group consisting of SEQ ID NOs: 2, 3, 6, 27, 28, 42, 45, 47, 50, 51, 53, 54, 62, 63, 64, 66, 71, 72 and 76.

[3] An isolated peptide selected from the group consisting of (i) and (ii) below:
(i) an isolated peptide of (a) or (b) below:
(a) an isolated peptide comprising an amino acid sequence selected from the group consisting of SEQ ID NOs: 2, 3, 6, 27 and 28,
(b) an isolated peptide comprising an amino acid sequence selected from the group consisting of SEQ ID NOs: 2, 3, 6, 27 and 28, in which 1, 2, or several amino acid(s) are substituted, inserted, deleted, and/or added, wherein the peptide has CTL inducibility,
(ii) an isolated peptide of (c) or (d) below:
(c) an isolated peptide comprising an amino acid sequence selected from the group consisting of SEQ ID NOs: 42, 45, 47, 50, 51, 53, 54, 62, 63, 64, 66, 71, 72 and 76,
(d) an isolated peptide comprising an amino acid sequence selected from the group consisting of SEQ ID NOs: 42, 45, 47, 50, 51, 53, 54, 62, 63, 64, 66, 71, 72 and 76, in which 1, 2, or several amino acid(s) are substituted, inserted, deleted, and/or added, wherein the peptide has CTL inducibility.

[4] The isolated peptide of [3], wherein the peptide has one or both of the following characteristics:
(a) the second amino acid from the N-terminus of an amino acid sequence selected from the group consisting of SEQ ID NOs: 2, 3, 6, 27 and 28 is substituted to be an amino acid selected from the group consisting of phenylalanine, tyrosine, methionine, and tryptophan, and
(b) the C-terminal amino acid of an amino acid sequence selected from the group consisting of SEQ ID NOs: 2, 3, 6, 27 and 28 is substituted to be an amino acid selected from the group consisting of phenylalanine, leucine, isoleucine, tryptophan, and methionine.

[5] The isolated peptide of [3], wherein the peptide has one or both of the following characteristics:
(a) the second amino acid from the N-terminus of an amino acid sequence selected from the group consisting of SEQ ID NOs: 42, 45, 47, 50, 51, 53, 54, 62, 63, 64, 66, 71, 72 and 76 is substituted to be an amino acid selected from the group consisting of leucine and methionine; and
(b) the C-terminal amino acid of an amino acid sequence selected from the group consisting of SEQ ID NOs: 42, 45, 47, 50, 51, 53, 54, 62, 63, 64, 66, 71, 72 and 76 is substituted to be an amino acid selected from the group consisting of valine and leucine.

[6] The isolated peptide of any one of [1] to [5], wherein said peptide has an ability to bind to an HLA antigen.

[7] The isolated peptide of [6], wherein said HLA antigen is HLA-A24 or HLA-A2.

[8] The isolated peptide of any one of [1] to [7], wherein said peptide is a nonapeptide or a decapeptide.

[9] An isolated polynucleotide encoding the isolated peptide of any one of [1] to [8].

[10] A composition for inducing a CTL, wherein the composition comprises one or more peptide(s) of any one of [1] to [8], or one or more polynucleotide(s) of [9].

[11] A pharmaceutical composition comprising:
(a) one or more peptide(s) of any one of [1] to [8],
(b) one or more polynucleotide(s) of [9],
(c) one or more APC(s) that present a complex of the peptide of any one of [1] to [8] and an HLA antigen on their surface;
(d) one or more exosomes that present a complex of the peptide of any one of [1] to [8] and an HLA antigen on their surface or (e) one or more CTLs that can recognize a cell presenting a complex of the peptide of any one of [1] to [8] and an HLA antigen on their surface, in combination with a pharmaceutically acceptable carrier, wherein the pharmaceutical composition is formulated for the treatment and/or prophylaxis of cancer, the prevention of a postoperative recurrence thereof, and/or the induction of an immune response against cancer.

[12] The pharmaceutical composition of [11], wherein said pharmaceutical composition is formulated for administration to a subject whose HLA antigen is HLA-A24 or HLA-A2.

[13] A method for inducing an antigen-presenting cell (APC) with CTL inducibility, said method comprising the step selected from the group consisting of:

(a) contacting an APC with a peptide of any one of [1] to [8] in vitro, ex vivo or in vivo, and (b) introducing a polynucleotide encoding the peptide of any one of [1] to [8] into an APC.

[14] A method for inducing a CTL, said method comprising a step selected from the group consisting of:

(a) co-culturing a CD8-positive T cell with an APC that presents on its surface a complex of an HLA antigen and the peptide of any one of [1] to [8], (b) co-culturing a CD8-positive T cell with an exosome that presents on its surface a complex of an HLA antigen and the peptide of any one of [1] to [8], and (c) introducing into a CD8-positive T cell a polynucleotide/polynucleotides encoding T cell receptor (TCR) subunit polypeptides, wherein the TCR formed by said TCR subunit polypeptides is capable of binding to a complex of an HLA antigen and the peptide of any one of [1] to [8] on a cell surface.

[15] An isolated APC that presents on its surface a complex of an HLA antigen and the peptide of any one of [1] to [8].

[16] The APC of [15], which is induced by the method of [13].

[17] An isolated CTL that targets the peptide of any one of [1] to [8].

[18] The CTL of [17], which is induced by the method of [14].

[19] A method of inducing an immune response against cancer in a subject, said method comprising the step of administering to the subject a composition comprising the peptide of any one of [1] to [8], an immunologically active fragment thereof, or a polynucleotide encoding the peptide or the fragment.

[20] An antibody or immunologically active fragment thereof against the peptide of any one of [1] to [8].

[21] A vector comprising a nucleotide sequence encoding the peptide of any one of [1] to [8].

[22] A host cell transformed or transfected with the vector of [21].

[23] A diagnostic kit comprising a peptide of any one of [1] to [8], the polynucleotide of [9] or the antibody of [20].

[24] A method of screening for a peptide having an ability to induce a CTL that has specific cytotoxic activity against a cell that presents a fragment derived from TOPK, wherein the method comprises the steps of:

(i) providing a candidate sequence consisting of an amino acid sequence modified by substituting, deleting, inserting and/or adding one, two or several amino acid residues to an original amino acid sequence, wherein the original amino acid sequence is selected from the group consisting of SEQ ID NOs: 2, 3, 6, 27, 28, 42, 45, 47, 50, 51, 53, 54, 62, 63, 64, 66, 71, 72 and 76;

(ii) selecting a candidate sequence that does not have substantial significant homology with the peptides derived from any known human gene products other than TOPK;

(iii) contacting a peptide consisting of the candidate sequence selected in step (ii) with an antigen presenting cell;

(iv) contacting the antigen presenting cell of step (iii) with a CD8-positive T cell; and (v) identifying the peptide of which CTL inducibility is same to or higher than a peptide consisting of the original amino acid sequence.

Although any methods and materials similar or equivalent to those described herein can be used in the practice or testing of embodiments of the present invention, the preferred methods, devices, and materials are now described. However, before the present materials and methods are described, it should be understood that these descriptions are merely illustrative and not intended to be limited. It should also be understood that the present invention is not limited to the particular sizes, shapes, dimensions, materials, methodologies, protocols, etc. described herein, as these may vary in accordance with routine experimentation and optimization. Furthermore, the terminology used in the description is for the purpose of describing the particular versions or embodiments only, and is not intended to limit the scope of the present invention which will be limited only by the appended claims.

The disclosure of each publication, patent or patent application mentioned in this specification is specifically incorporated by reference herein in its entirety. However, nothing herein is to be construed as an admission that the invention is not entitled to antedate such disclosure by virtue or prior invention.

Unless otherwise defined, all technical and scientific terms used herein have the same meaning as commonly understood by one of ordinary skill in the art to which the present invention belongs. In case of conflict, the present specification, including definitions, will control. In addition, the materials, methods, and examples are illustrative only and not intended to be limiting

I. DEFINITIONS

The words "a", "an", and "the" as used herein mean "at least one" unless otherwise specifically indicated.

The terms "isolated" and "purified" used in relation with a substance (e.g., peptide, antibody, polynucleotide, etc.) indicates that the substance is substantially free from at least one substance that may else be included in the natural source. Thus, an isolated or purified peptide refers to a peptide that are substantially free of cellular material such as carbohydrate, lipid, or other contaminating proteins from the cell or tissue source from which the peptide is derived, or substantially free of chemical precursors or other chemicals when chemically synthesized.

The term "substantially free of cellular material" includes preparations of a peptide in which the peptide is separated from cellular components of the cells from which it is isolated or recombinantly produced. Thus, a peptide that is substantially free of cellular material includes preparations of polypeptide having less than about 30%, 20%, 10%, or 5% (by dry weight) of heterologous protein (also referred to herein as a "contaminating protein"). When the peptide is recombinantly produced, it is also preferably substantially free of culture medium, which includes preparations of peptide with culture medium less than about 20%, 10%, or 5% of the volume of the peptide preparation. When the peptide is produced by chemical synthesis, it is preferably substantially free of chemical precursors or other chemicals, which includes preparations of peptide with chemical precursors or other chemicals involved in the synthesis of the peptide less than about 30%, 20%, 10%, 5% (by dry weight) of the volume of the peptide preparation. That a particular peptide preparation contains an isolated or purified peptide can be shown, for example, by the appearance of a single band following sodium dodecyl sulfate (SDS)-polyacrylamide gel electrophoresis of the protein preparation and Coomassie Brilliant Blue staining or the like of the gel. In a preferred embodiment, peptides and polynucleotides of the present invention are isolated or purified.

The terms "polypeptide", "peptide" and "protein" are used interchangeably herein to refer to a polymer of amino acid residues. The terms apply to amino acid polymers in which one or more amino acid residue(s) is/are one or more modified residue(s), or non-naturally occurring residue(s), such as an artificial chemical mimetic of a corresponding naturally occurring amino acid(s), as well as to naturally occurring amino acid polymers.

The term "oligopeptide" sometimes used in the present specification is used to refer to peptides which are 20 amino acid residues or fewer, typically 15 amino acid residues or fewer in length and is typically composed of between about 8 and about 11 amino acid residues, often 9 or 10 amino acid residues. The latter are referred to herein as "nonapeptide" and "decapeptide", respectively.

The term "amino acid" as used herein refers to naturally occurring and synthetic amino acids, as well as amino acid analogs and amino acid mimetics that similarly function to the naturally occurring amino acids. Amino acids may be either L-amino acids or D-amino acids. Naturally occurring amino acids are those encoded by the genetic code, as well as those modified after translation in cells (e.g., hydroxyproline, gamma-carboxyglutamate, and O-phosphoserine). The phrase "amino acid analog" refers to compounds that have the same basic chemical structure (an alpha carbon bound to a hydrogen, a carboxy group, an amino group, and an R group) as a naturally occurring amino acid but have a modified R group or modified backbones (e.g., homoserine, norleucine, methionine, sulfoxide, methionine methyl sulfonium). The phrase "amino acid mimetic" refers to chemical compounds that have different structures but similar functions to general amino acids.

Amino acids may be referred to herein by their commonly known three letter symbols or the one-letter symbols recommended by the IUPAC-IUB Biochemical Nomenclature Commission.

The terms "gene", "polynucleotide", "oligonucleotide" and "nucleic acid" are used interchangeably herein and, unless otherwise specifically indicated, are referred to by their commonly accepted single-letter codes.

The term "agent" and "composition" are used interchangeably herein to refer to a product that includes specified ingredients in specified amounts, as well as any product that results, directly or indirectly, from combination of the specified ingredients in the specified amounts. Such terms, when used in relation to the modifier "pharmaceutical" (as in "pharmaceutical agent" and "pharmaceutical composition") are intended to encompass a product including the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, in the context of the present invention, the terms "pharmaceutical agent" and "pharmaceutical composition" refer to any products made by admixing a molecule or compound of the present invention and a pharmaceutically or physiologically acceptable carrier.

The term "active ingredient" herein refers to a substance in an agent or composition that is biologically or physiologically active. Particularly, in the context of a pharmaceutical agent or composition, the term "active ingredient" refers to a component substance that shows an objective pharmacological effect. For example, in case of pharmaceutical agents or compositions for use in the treatment or prevention of cancer, active ingredients in the agents or compositions may lead to at least one biological or physiological action on cancer cells and/or tissues directly or indirectly. Preferably, such action may include reducing or inhibiting cancer cell growth, damaging or killing cancer cells and/or tissues, and so on. Typically, indirect effect of active ingredients is inductions of CTLs recognizing or killing cancer cells. Before being formulated, the "active ingredient" may also be referred to as "bulk", "drug substance" or "technical product".

The phrase "pharmaceutically acceptable carrier" or "physiologically acceptable carrier", as used herein, means a pharmaceutically or physiologically acceptable material, composition, substance or vehicle, including, but are not limited to, a liquid or solid filler, diluent, excipient, solvent or encapsulating material.

Some pharmaceutical agents or compositions of the present invention find particular use as vaccines. In the context of the present invention, the phrase "vaccine" (also referred to as an "immunogenic composition") refers to an agent or composition that has the function to improve, enhance and/or induce anti-tumor immunity upon inoculation into animals.

Unless otherwise defined, the term "cancer" refers to cancers or tumors that over-express the TOPK gene, examples of which include, but are not limited to, acute myeloid leukemia (AML), bladder cancer, breast cancer, cervical cancer, cholangiocellular carcinoma, colorectal cancer, diffuse-type gastric cancer, non small cell lung cancer (NSCLC), lymphoma, osteosarcoma, prostate cancer, renal carcinoma, small cell lung cancer (SCLC) and soft tissue tumor.

Unless otherwise defined, the terms "cytotoxic T lymphocyte", "cytotoxic T cell" and "CTL" are used interchangeably herein and unless otherwise specifically indicated, refer to a sub-group of T lymphocytes that are capable of recognizing non-self cells (e.g., tumor/cancer cells, virus-infected cells) and inducing the death of such cells.

Unless otherwise defined, the terms "HLA-A24" refers to the HLA-A24 type containing the subtypes, examples of which include, but are not limited to, HLA-A*2401, HLA-A*2402, HLA-A*2403, HLA-A*2404, HLA-A*2407, HLA-A*2408, HLA-A*2420, HLA-A*2425 and HLA-A*2488.

Unless otherwise defined, the term "HLA-A2", as used herein, representatively refers to the subtypes, examples of which include, but are not limited to, HLA-A*0201, HLA-A*0202, HLA-A*0203, HLA-A*0204, HLA-A*0205, HLA-A*0206, HLA-A*0207, HLA-A*0210, HLA-A*0211, HLA-A*0213, HLA-A*0216, HLA-A*0218, HLA-A*0219, HLA-A*0228 and HLA-A*0250.

Unless otherwise defined, the term "kit" as used herein, is used in reference to a combination of reagents and other materials. It is contemplated herein that the kit may include microarray, chip, marker, and so on. It is not intended that the term "kit" be limited to a particular combination of reagents and/or materials.

As used herein, in the context of a subject or patient, the phrase "subject's (or patient's) HLA antigen is HLA A24 or HLA-A2" refers to that the subject or patient homozygously or heterozygously possess HLA-A24 or HLA-A2 antigen gene as an MHC (major histocompatibility complex) Class 1 molecule, and HLA-A24 or HLA-A2 antigen is expressed in cells of the subject or patient as an HLA antigen.

To the extent that the methods and compositions of the present invention find utility in the context of the "treatment" of cancer, a treatment is deemed "efficacious" if it leads to clinical benefit such as, reduction in expression of TOPK gene, decrease in size, prevalence, or metastatic potential of the cancer in a subject, retarding progression of cancer, alleviation of a clinical symptom of cancer, prolongation of survival time, suppression of postoperative recurrence and so on. When the treatment is applied prophylactically, "efficacious" means that it retards or prevents cancers from forming or prevents or alleviates a clinical symptom of cancer. Efficaciousness is determined in association with any known method for diagnosing or treating the particular tumor type.

To the extent that the methods and compositions of the present invention find utility in the context of the "prevention" and "prophylaxis" of cancer, such terms are interchangeably used herein to refer to any activity that reduces the burden of mortality or morbidity from disease. Prevention and prophylaxis can occur "at primary, secondary and tertiary prevention levels." While primary prevention and prophylaxis avoid the development of a disease, secondary and tertiary levels of prevention and prophylaxis encompass activities aimed at the prevention and prophylaxis of the progression of a disease and the emergence of symptoms as well as reducing the negative impact of an already established disease by restoring function and reducing disease-related complications. Alternatively, prevention and prophylaxis can include a wide range of prophylactic therapies aimed at alleviating the severity of the particular disorder, e.g. reducing the proliferation and metastasis of tumors.

In the context of the present invention, the treatment and/or prophylaxis of cancer and/or the prevention of postoperative recurrence thereof include any of the following steps, such as the surgical removal of cancer cells, the inhibition of the growth of cancerous cells, the involution or regression of a tumor, the induction of remission and suppression of occurrence of cancer, the tumor regression, and the reduction or inhibition of metastasis. Effective treatment and/or the prophylaxis of cancer decreases mortality and improves the prognosis of individuals having cancer, decreases the levels of tumor markers in the blood, and alleviates detectable symptoms accompanying cancer. For example, reduction or improvement of symptoms constitutes effectively treating and/or the prophylaxis include 10%, 20%, 30% or more reduction, or stable disease.

In the context of the present invention, the term "antibody" refers to immunoglobulins and fragments thereof that are specifically reactive to a designated protein or peptide thereof. An antibody can include human antibodies, primatized antibodies, chimeric antibodies, bispecific antibodies, humanized antibodies, antibodies fused to other proteins or radiolabels, and antibody fragments. Furthermore, an antibody herein is used in the broadest sense and specifically covers intact monoclonal antibodies, polyclonal antibodies, multispecific antibodies (e.g., bispecific antibodies) formed from at least two intact antibodies, and antibody fragments so long as they exhibit the desired biological activity. An "antibody" indicates all classes (e.g., IgA, IgD, IgE, IgG and IgM).

Unless otherwise defined, all technical and scientific terms used herein have the same meaning as commonly understood by one of ordinary skill in the art to which this invention belongs.

II. PEPTIDES

Peptides of the present invention described in detail below may be referred to as "TOPK peptide(s)" or "TOPK polypeptide(s)".

To demonstrate that peptides derived from TOPK function as an antigen recognized by CTLs, peptides derived from TOPK (SEQ ID NO: 86) were analyzed to determine whether they were antigen epitopes restricted by HLA-A24 or HLA-A2 which are commonly encountered HLA alleles (Date Y et al., Tissue Antigens 47: 93-101, 1996; Kondo A et al., J Immunol 155: 4307-12, 1995; Kubo R T et al., J Immunol 152: 3913-24, 1994).

Candidates of HLA-A24 binding peptides derived from TOPK identified based on their binding affinities to HLA-A24 include:

TOPK-A24-9-230 (SEQ ID NO: 2), TOPK-A24-9-130 (SEQ ID NO: 3), TOPK-A24-9-237 (SEQ ID NO: 4), TOPK-A24-9-155 (SEQ ID NO: 5), TOPK-A24-9-232 (SEQ ID NO: 6), TOPK-A24-9-174 (SEQ ID NO: 7), TOPK-A24-9-73 (SEQ ID NO: 8), TOPK-A24-9-235 (SEQ ID NO: 9), TOPK-A24-9-19 (SEQ ID NO: 10), TOPK-A24-9-205 (SEQ ID NO: 11), TOPK-A24-9-77 (SEQ ID NO: 12), TOPK-A24-9-270 (SEQ ID NO: 13), TOPK-A24-9-58 (SEQ ID NO: 14), TOPK-A24-9-81 (SEQ ID NO: 15), TOPK-A24-9-278 (SEQ ID NO: 16), TOPK-A24-9-183 (SEQ ID NO: 17), TOPK-A24-9-227 (SEQ ID NO: 18), TOPK-A24-9-13 (SEQ ID NO: 19), TOPK-A24-9-146 (SEQ ID NO: 20), TOPK-A24-9-140 (SEQ ID NO: 21), TOPK-A24-9-103 (SEQ ID NO: 22), TOPK-A24-9-105 (SEQ ID NO: 23), TOPK-A24-9-118 (SEQ ID NO: 24), TOPK-A24-10-31 (SEQ ID NO: 25), TOPK-A24-10-155 (SEQ ID NO: 26), TOPK-A24-10-288 (SEQ ID NO: 27), TOPK-A24-10-289 (SEQ ID NO: 28), TOPK-A24-10-130 (SEQ ID NO: 29), TOPK-A24-10-47 (SEQ ID NO: 30), TOPK-A24-10-73 (SEQ ID NO: 31), TOPK-A24-10-102 (SEQ ID NO: 32), TOPK-A24-10-39 (SEQ ID NO: 33), TOPK-A24-10-4 (SEQ ID NO: 34), TOPK-A24-10-77 (SEQ ID NO: 35), TOPK-A24-10-241 (SEQ ID NO: 36), TOPK-A24-10-12 (SEQ ID NO: 37), TOPK-A24-10-148 (SEQ ID NO: 38), TOPK-A24-10-145 (SEQ ID NO: 39) and TOPK-A24-10-114 (SEQ ID NO: 40).

Of the above, the following peptides resulted in the successful establishment of CTLs after in vitro stimulation of T-cells by dendritic cells (DCs) loaded with these peptides:

TOPK-A24-9-230 (SEQ ID NO:2), TOPK-A24-9-130 (SEQ ID NO:3), TOPK-A24-9-232 (SEQ ID NO:6), TOPK-A24-10-288 (SEQ ID NO: 27) and TOPK-A24-10-289 (SEQ ID NO: 28).

Candidates of HLA-A2 binding peptides derived from TOPK identified based on their binding affinities to HLA-A2 include:

TOPK-A2-9-240 (SEQ ID NO: 42), TOPK-A2-9-34 (SEQ ID NO: 43), TOPK-A2-9-236 (SEQ ID NO: 44), TOPK-A2-9-19 (SEQ ID NO: 45), TOPK-A2-9-134 (SEQ ID NO: 46), TOPK-A2-9-183 (SEQ ID NO: 47), TOPK-A2-9-81 (SEQ ID NO: 48), TOPK-A2-9-149 (SEQ ID NO:

49), TOPK-A2-9-235 (SEQ ID NO: 50), TOPK-A2-9-12 (SEQ ID NO: 51), TOPK-A2-9-227 (SEQ ID NO: 52), TOPK-A2-9-285 (SEQ ID NO: 53), TOPK-A2-9-47 (SEQ ID NO: 54), TOPK-A2-9-310 (SEQ ID NO: 55), TOPK-A2-9-132 (SEQ ID NO: 56), TOPK-A2-9-242 (SEQ ID NO: 57), TOPK-A2-9-156 (SEQ ID NO: 58), TOPK-A2-9-138 (SEQ ID NO: 59), TOPK-A2-9-142 (SEQ ID NO: 60), TOPK-A2-10-190 (SEQ ID NO: 61), TOPK-A2-10-236 (SEQ ID NO: 62), TOPK-A2-10-231 (SEQ ID NO: 63), TOPK-A2-10-47 (SEQ ID NO: 64), TOPK-A2-10-234 (SEQ ID NO: 65), TOPK-A2-10-239 (SEQ ID NO: 66), TOPK-A2-10-290 (SEQ ID NO: 67), TOPK-A2-10-37 (SEQ ID NO: 68), TOPK-A2-10-20 (SEQ ID NO: 69), TOPK-A2-10-241 (SEQ ID NO: 70), TOPK-A2-10-272 (SEQ ID NO: 71), TOPK-A2-10-88 (SEQ ID NO: 72), TOPK-A2-10-81 (SEQ ID NO: 73), TOPK-A2-10-313 (SEQ ID NO: 74), TOPK-A2-10-54 (SEQ ID NO: 75), TOPK-A2-10-142 (SEQ ID NO: 76), TOPK-A2-10-35 (SEQ ID NO: 77), TOPK-A2-10-110 (SEQ ID NO: 78), TOPK-A2-10-223 (SEQ ID NO: 79), TOPK-A2-10-274 (SEQ ID NO: 80), TOPK-A2-10-173 (SEQ ID NO: 81), TOPK-A2-10-141 (SEQ ID NO: 82), TOPK-A2-10-292 (SEQ ID NO: 83) and TOPK-A2-10-180 (SEQ ID NO: 84).

Of the above, the following peptides resulted in the successful establishment of CTLs after in vitro stimulation of T-cells by dendritic cells (DCs) loaded with these peptides:

TOPK-A02-9-240 (SEQ ID NO:42), TOPK-A02-9-19 (SEQ ID NO:45), TOPK-A02-9-183 (SEQ ID NO:47), TOPK-A02-9-235 (SEQ ID NO:50), TOPK-A02-9-12 (SEQ ID NO:51), TOPK-A02-9-285 (SEQ ID NO:53), TOPK-A02-9-47 (SEQ ID NO:54), TOPK-A02-10-236 (SEQ ID NO:62), TOPK-A02-10-231 (SEQ ID NO:63), TOPK-A02-10-47 (SEQ ID NO:64), TOPK-A02-10-239 (SEQ ID NO:66), TOPK-A02-10-272 (SEQ ID NO:71), TOPK-A02-10-88 (SEQ ID NO:72) and TOPK-A02-10-142 (SEQ ID NO:76).

The established CTLs noted above showed potent specific CTL activity against target cells pulsed with respective peptides. These results demonstrate that TOPK is an antigen recognized by a CTL and that the peptides are epitope peptides of TOPK restricted by HLA-A24 or HLA-A2; therefore, such peptides may be effective as target antigens for cytotoxicity by CTLs.

Since the TOPK gene is over-expressed in cancer cells and tissues, including for example those of AML, bladder cancer, breast cancer, cervical cancer, cholangiocellular carcinoma, colorectal cancer, diffuse-type gastric cancer, NSCLC, lymphoma, osteosarcoma, prostate cancer, renal carcinoma, SCLC and soft tissue tumor, and not expressed in most normal organs, it represents a good target for immunotherapy. Thus, the present invention provides nonapeptides (peptides composed of nine amino acid residues) and decapeptides (peptides composed of ten amino acid residues) corresponding to CTL-recognized epitopes from TOPK. Particularly preferred examples of nonapeptides and decapeptides of the present invention include those peptides having an amino acid sequence selected from among SEQ ID NOs: 2 to 40 and 42 to 84.

Generally, software programs now available, for example, on the Internet, such as those described in Parker K C et al., J Immunol 1994, 152(1): 163-75 and Nielsen M et al., Protein Sci 2003; 12: 1007-17 can be used to calculate the binding affinities between various peptides and HLA antigens in silico. Binding affinity with HLA antigens can be measured as described, for example, in Parker K C et al., J Immunol 1994, 152(1): 163-75, Kuzushima K et al., Blood 2001, 98(6): 1872-81, Larsen M V et al. BMC Bioinformatics. 2007; 8: 424, Buus S et al. Tissue Antigens., 62:378-84, 2003, Nielsen M et al., Protein Sci 2003; 12: 1007-17, and Nielsen M et al. PLoS ONE 2007; 2: e796, which are summarized in, e.g., Lafuente E M et al., Current Pharmaceutical Design, 2009, 15, 3209-3220. Methods for determining binding affinity are described, for example, in the Journal of Immunological Methods (1995, 185: 181-190) and Protein Science (2000, 9: 1838-1846). Therefore, one can readily utilize such software programs to select those fragments derived from TOPK that have high binding affinity with HLA antigens using such software programs. Accordingly, the present invention encompasses peptides composed of any fragments derived from TOPK, which would be determined to bind with HLA antigens by such known programs. Furthermore, such peptides may include the peptide composed of the full length of TOPK sequence.

The peptides of the present invention, particularly the nonapeptides and decapeptides of the present invention, can be flanked with additional amino acid residues, so long as the resulting peptide retains its CTL inducibility. The particular additional amino acid residues can be composed of any kind of amino acids, so long as they do not impair the CTL inducibility of the original peptide. Thus, the present invention encompasses peptides having CTL inducibility, in particular peptides derived from TOPK (e.g., peptides including an amino acid sequence of SEQ ID NO: 2, 3, 6, 27, 28, 42, 45, 47, 50, 51, 53, 54, 62, 63, 64, 66, 71, 72, or 76). Such peptides are, for example, less than about 40 amino acids, often less than about 20 amino acids, and usually less than about 15 amino acids.

It is generally known that modification of one, two or more amino acids in a peptide will not influence the function of the peptide, and in some cases will even enhance the desired function of the original protein. In fact, modified peptides (i.e., peptides composed of an amino acid sequence, in which 1, 2 or several amino acid residues have been modified (i.e., substituted, added, deleted and/or inserted) as compared to an original reference sequence) have been known to retain the biological activity of the original peptide (Mark et al., Proc Natl Acad Sci USA 1984, 81: 5662-6; Zoller and Smith, Nucleic Acids Res 1982, 10: 6487-500; Dalbadie-McFarland et al., Proc Natl Acad Sci USA 1982, 79: 6409-13). Thus, in one embodiment, the peptides of the present invention have both CTL inducibility and an amino acid sequence selected from among SEQ ID NOs: 2 to 40 and 42 to 84, in which one, two or even more amino acids are added, deleted, inserted and/or substituted. In other words, the peptides of the present invention have both CTL inducibility and an amino acid sequence in which on, two or several amino acid(s) are substituted, deleted, inserted and/ or added in the amino acid sequence selected from among SEQ ID NOs: 2 to 40 and 42 to 84, provided the modified peptides retain the CTL inducibility of the original peptide.

Those of skill in the art will recognize that individual modifications (i.e., deletions, insertions, additions and/or substitutions) to an amino acid sequence that alter a single amino acid or a small percentage of the overall amino acid sequence tend to result in the conservation of the properties of the original amino acid side-chain. As such, they are often referred to as "conservative substitutions" or "conservative modifications", wherein the alteration of a protein results in a modified protein having a function analogous to the original protein. Conservative substitution tables providing functionally similar amino acids are well known in the art. Examples of amino acid side-chains characteristics that are desirable to conserve include, for example: hydrophobic amino acids (A, I, L, M, F, P, W, Y, V), hydrophilic amino acids (R, D, N, C, E, Q, G, H, K, S, T), and side-chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). In addition, the following eight groups each contain amino acids that are accepted in the art as conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins 1984).

Such conservatively modified peptides are also considered to be peptides of the present invention. However, peptides of the present invention are not restricted thereto and can include non-conservative modifications, so long as the resulting modified peptide retains the CTL inducibility of the original unmodified peptide. Furthermore, modified peptides should not exclude CTL inducible peptides derived from polymorphic variants, interspecies homologues, and alleles of TOPK.

Amino acid residues may be inserted, substituted and/or added to the peptides of the present invention or, alternatively, amino acid residues may be deleted therefrom to achieve a higher binding affinity. To retain the requisite CTL inducibility, one preferably modifies (i.e, deletes, inserts, adds and/or substitutes) only a small number (for example, 1, 2 or several) or a small percentage of amino acids. Herein, the term "several" means 5 or fewer amino acids, for example, 4 or 3 or fewer. The percentage of amino acids to be modified is preferably 20% or less, more preferably 15% or less, and even more preferably 10% or less, for example 1 to 5%.

When used in the context of immunotherapy, the peptides of the present invention should be presented on the surface of a cell or exosome, preferably as a complex with an HLA antigen. Therefore, it is preferable to select peptides that not only induce CTLs but also possess high binding affinity to the HLA antigen. To that end, the peptides can be modified by substitution, insertion, deletion and/or addition of the amino acid residues to yield a modified peptide having improved binding affinity. In addition to peptides that are naturally displayed, since the regularity of the sequences of peptides displayed by binding to HLA antigens is already known (J Immunol 1994, 152: 3913; Immunogenetics 1995, 41: 178; J Immunol 1994, 155: 4307), modifications based on such regularity can be introduced into the immunogenic peptides of the invention.

For example, peptides possessing high HLA-A24 binding affinity tend to have the second amino acid from the N-terminus substituted with phenylalanine, tyrosine, methionine, or tryptophan. Likewise, peptides in which the C-terminal amino acid is substituted with phenylalanine, leucine, isoleucine, tryptophan or methionine tend to have high HLA-A24 binding affinity. Accordingly, it may be desirable to substitute the second amino acid from the N-terminus with phenylalanine, tyrosine, methionine, or tryptophan, and/or the amino acid at the C-terminus with phenylalanine, leucine, isoleucine, tryptophan, or methionine in order to increase the HLA-A24 binding affinity. Thus, peptides having an amino acid sequence selected from among SEQ ID NOs: 2 to 40 (especially SEQ ID NOs: 2, 3, 6, 27 and 28), in which the second amino acid from the N-terminus of the amino acid sequence of the SEQ ID NO is substituted with phenylalanine, tyrosine, methionine, or tryptophan, and/or in which the C-terminus of the amino acid sequence of the SEQ ID NO is substituted with phenylalanine, leucine, isoleucine, tryptophan or methionine are encompassed by the present invention. Also, the present invention encompasses the peptides including an amino acid sequence in which one, two or several amino acid are substituted, deleted, inserted and/or added in the amino acid sequence selected from among SEQ ID NOs: 2 to 40 (especially SEQ ID NOs: 2, 3, 6, 27 and 28), such peptides having one or both of the following characteristic of (a) the second amino acid from the N-terminus is phenylalanine, tyrosine, methionine or tryptophan; and (b) the C-terminal amino acid is phenylalanine, leucine, isoleucine, tryptophan or methionine. In preferred embodiments, the peptides of the present invention include an amino acid sequence in which the second amino acid from the N-terminus is substituted with phenylalanine, tyrosine, methionine or tryptophan, and/or the C-terminal amino acid is substituted with phenylalanine, leucine, isoleucine, tryptophan or methionine in the amino acid sequence selected from among SEQ ID NOs: 2 to 40 (especially SEQ ID NOs: 2, 3, 6, 27 and 28).

Likewise, peptides showing high HLA-A2 binding affinity tend to have the second amino acid from the N-terminus substituted with leucine or methionine and/or the amino acid at the C-terminus substituted with valine or leucine. Alternatively, it may be desirable to substitute the second amino acid from the N-terminus with leucine or methionine, and/or the amino acid at the C-terminus with valine or leucine in order to increase the HLA-A2 binding affinity. Thus, peptides having an amino acid sequence selected from among SEQ ID NOs: 42 to 84 (especially SEQ ID NOs: 42, 45, 47, 50, 51, 53, 54, 62, 63, 64, 66, 71, 72 and 76), in which the second amino acid from the N-terminus of the amino acid sequence of the SEQ ID NO is substituted with leucine or methionine, and/or in which the C-terminus of the amino acid sequence of the SEQ ID NO is substituted with valine or leucine are encompassed by the present invention. Also, the present invention encompasses the peptides including an amino acid sequence in which one, two or several amino acid are substituted, deleted, inserted and/or added in the amino acid sequence selected from among SEQ ID NOs: 42 to 84 (especially SEQ ID NOs: 42, 45, 47, 50, 51, 53, 54, 62, 63, 64, 66, 71, 72 and 76), such peptides having one or both of the following characteristic of (a) the second amino acid from the N-terminus is leucine or methionine; and (b) the C-terminal amino acid is valine or leucine. In preferred embodiments, the peptides of the present invention include an amino acid sequence in which the second amino acid from the N-terminus is substituted with leucine or methionine, and/or the C-terminal amino acid is substituted with valine or leucine in the amino acid sequence selected from among SEQ ID NOs: 42 to 84 (especially SEQ ID NOs: 42, 45, 47, 50, 51, 53, 54, 62, 63, 64, 66, 71, 72 and 76).

Substitutions can be introduced not only at the terminal amino acids but also at the position of potential T cell receptor (TCR) recognition of peptides. Several studies have demonstrated that a peptide with amino acid substitutions can be equal to or better than the original, for example CAP1, p53$_{(264-272)}$, Her-2/neu$_{(369-377)}$ or gp100$_{(209-217)}$ (Zaremba et al. Cancer Res. 57, 4570-4577, 1997, T. K. Hoffmann et al. J. Immunol. (2002); 168(3):1338-47., S. O. Dionne et al. Cancer Immunol immunother. (2003) 52: 199-206 and S. O. Dionne et al. Cancer Immunology, Immunotherapy (2004) 53, 307-314).

The present invention also contemplates the addition of 1, 2 or several amino acids can also be added to the N and/or C-terminus of the present peptides. Such modified peptides having CTL inducibility are also included in the present invention.

For example, the present invention provides an isolated peptide of less than 15, 14, 13, 12, 11, or 10 amino acids in length, which has CTL inducibility and comprises the amino acid sequence selected from the group consisting of:

(i) an amino acid sequence selected from among SEQ ID NOs: 2 to 24 and 42 to 60, (ii) an amino acid sequence in which 1, 2 or several amino acid(s) are modified in the amino acid sequence selected from the group consisting of SEQ ID NOs: 2 to 24 and 42 to 60, wherein the peptide has an ability to induce a cytotoxic T lymphocyte, (iii) the amino acid sequence of (ii), wherein, in the context of HLA-A24, the amino acid sequence has one or both of the following characteristics:

(a) the second amino acid from the N-terminus of said SEQ ID NOs is or is modified to be an amino acid selected from the group consisting of phenylalanine, tyrosine, methionine, and tryptophan, and (b) the C-terminal amino acid of said SEQ ID NOs is or is modified to be an amino acid selected from the group consisting of phenylalanine, leucine, isoleucine, tryptophan, and methionine, and (iv) the amino acid sequence of (ii), wherein, in the context of HLA-A2, the amino acid sequence has one or both of the following characteristics:

(c) the second amino acid from the N-terminus of said SEQ ID NO is or is modified to be an amino acid selected from the group consisting of leucine and methionine; and (d) the C-terminal amino acid of said SEQ ID NO is or is modified to be an amino acid selected from the group consisting of valine and leucine.

Moreover, the present invention also provides an isolated peptide of less than 15, 14, 13, 12, or 11 amino acids in length, which has CTL inducibility and comprises the amino acid sequence selected from the group consisting of:

(i') an amino acid sequence selected from among SEQ ID NOs: 25 to 40 and 61 to 84, (ii') an amino acid sequence in which 1, 2 or several amino acid(s) are modified in the amino acid sequence selected from the group consisting of SEQ ID NOs: 25 to 40 and 61 to 84, wherein the peptide has an ability to induce a cytotoxic T lymphocyte, (iii') the amino acid sequence of (ii'), wherein, in the context of HLA-A24, the amino acid sequence has one or both of the following characteristics:

(a') the second amino acid from the N-terminus of said SEQ ID NOs is or is modified to be an amino acid selected from the group consisting of phenylalanine, tyrosine, methionine, and tryptophan, and (b') the C-terminal amino acid of said SEQ ID NOs is or is modified to be an amino acid selected from the group consisting of phenylalanine, leucine, isoleucine, tryptophan, and methionine.

(iv') the amino acid sequence of (ii'), wherein, in the context of HLA-A2, the amino acid sequence has one or both of the following characteristics:

(c') the second amino acid from the N-terminus of said SEQ ID NOs is or is modified to be an amino acid selected from the group consisting of leucine and methionine; and (d') the C-terminal amino acid of said SEQ ID NOs is or is modified to be an amino acid selected from the group consisting of valine and leucine.

These peptides bind with HLA antigens on APCs to be presented on APCs as complex with an HLA antigen when those peptides are contacted APCs. Alternatively, those peptides are introduced into APCs and processed to fragments having an amino acid sequence selected from among (i)-(iv) and (i')-(iv') in APCs to be presented on APCs as complexes with HLA antigens, when those peptides are contacted with APCs. Consequently, CTLs specific to such peptides are induced.

However, when the peptide sequence is identical to a portion of the amino acid sequence of an endogenous or exogenous protein having a different function, negative side effects such as autoimmune disorders and/or allergic symptoms against specific substances may be induced. Therefore, it may be desirable to first perform homology searches using available databases to avoid situations in which the sequence of the peptide matches the amino acid sequence of another protein. When it becomes clear from the homology searches that no peptide identical to or having 1 or 2 amino acid differences as compared to the objective peptide exists in nature, the objective peptide can be modified in order to increase its binding affinity with HLA antigens, and/or increase its CTL inducibility without any danger of such side effects.

Although peptides having high binding affinity to the HLA antigens as described above are expected to be highly effective, the candidate peptides, which are selected according to the presence of high binding affinity as an indicator, are further examined for the presence of CTL inducibility. Herein, the phrase "CTL inducibility" indicates the ability of the peptide to induce cytotoxic T lymphocytes (CTLs) when presented on antigen-presenting cells (APCs). Further, "CTL inducibility" includes the ability of the peptide to induce CTL activation, CTL proliferation, promote lysis of target cells by CTL, and to increase IFN-gamma production by CTL.

Confirmation of CTL inducibility is accomplished by inducing APCs carrying human MHC antigens (for example, B-lymphocytes, macrophages, and dendritic cells (DCs)), or more specifically DCs derived from human peripheral blood mononuclear leukocytes, and after stimulation of APCs with a test peptides, mixing APCs with CD8 positive T cells to induce CTLs, and then measuring the IFN-gamma produced and released by CTL against the target cells. As the reaction system, transgenic animals that have been produced to express a human HLA antigen (for example, those described in BenMohamed L, Krishnan R, Longmate J, Auge C, Low L, Primus J, Diamond D J, Hum Immunol 2000, 61(8): 764-79, Related Articles, Books, Linkout Induction of CTL response by a minimal epitope vaccine in HLA A*0201/DR1 transgenic mice: dependence on HLA class II restricted T(H) response) can be used. Alternatively, the target cells can be radiolabeled with $^{51}$Cr and such, and cytotoxic activity of CTL can be calculated from radioactivity released from the target cells. Alternatively, CTL inducibility can be assessed by measuring IFN-gamma produced and released by CTL in the presence of APCs that carry immobilized peptides, and visualizing the inhibition zone on the media using anti-IFN-gamma monoclonal antibodies.

As a result of examining the CTL inducibility of the peptides as described above, it was discovered that nonapeptides or decapeptides selected from among the amino acid sequences indicated by SEQ ID NOs: 2, 3, 6, 27, 28, 42, 45, 47, 50, 51, 53, 54, 62, 63, 64, 66, 71, 72 and 76 showed particularly high CTL inducibility as well as high binding affinity to an HLA antigen. Thus, these peptides are exemplified as preferred embodiments of the present invention.

Furthermore, homology analysis results demonstrated that such peptides do not have significant homology with peptides derived from any other known human gene products. Accordingly, the possibility of unknown or undesired immune responses arising when used for immunotherapy is lowered. Therefore, also from this aspect, these peptides are useful for eliciting immunity against TOPK in cancer patients. Thus, the preferred examples of the peptides of the present invention include, but are not limited to, peptides having an amino acid sequence selected from among SEQ ID NOs: 2, 3, 6, 27, 28, 42, 45, 47, 50, 51, 53, 54, 62, 63, 64, 66, 71, 72 and 76 and modified peptides thereof.

As noted above, the peptides of the present invention has an ability to induce a CTL specific to TOPK. For example, the peptides having an amino acid sequence selected from among SEQ ID NOs: 2, 3, 6, 27 and 28, or modified peptides thereof has an ability to induce a CTL that can show specific cytotoxic activity against a cell presenting a peptide derived from TOPK via HLA-A24 (e.g., cells expressing TOPK and HLA-A24). Examples of such cells include HLA-A24 positive cancer cells. Likewise, the peptides having an amino acid sequence selected from among SEQ ID NOs: 42, 45, 47, 50, 51, 53, 54, 62, 63, 64, 66, 71, 72 and 76, or modified peptides thereof has an ability to induce a CTL that can show specific cytotoxic activity against a cell presenting a peptide derived from TOPK via HLA-A2 (e.g., cells expressing TOPK and HLA-A2). Examples of such cells include HLA-A2 positive cancer cells.

In addition to the above-described modifications, the peptides of the present invention can also be linked to other peptides, so long as the resulting linked peptide retains the requisite CTL inducibility of the original peptide, and more preferably also retains the requisite HLA binding ability. Examples of suitable "other" peptides include: the peptides of the present invention or the CTL-inducible peptides derived from other TAAs. The peptide of the present invention can be linked "other" peptide via a linker directly or indirectly. Suitable inter-peptide linkers are well known in the art and include, for example AAY (P. M. Daftarian et al., J Trans Med 2007, 5:26), AAA, NKRK (R. P. M. Sutmuller et al., J. Immunol. 2000, 165: 7308-7315) or K (S. Ota et al., Can Res. 62, 1471-1476, K. S. Kawamura et al., J. Immunol. 2002, 168: 5709-5715).

For example, non-TOPK tumor associated antigen peptides also can be used subsequently or simultaneously to increase the immune response via HLA class I and/or class II. It is well established that cancer cells can express more than one tumor associated gene. Thus, it is within the scope of routine experimentation for one of ordinary skill in the art to determine whether a particular subject expresses additional tumor associated genes, and then to include HLA class I-binding peptides and/or HLA class II-binding peptides derived from such gene products in the pharmaceutical compositions or vaccines of the present invention.

Some of HLA class I- and HLA class II-binding peptides are known to those of ordinary skill in the art (for example, see Coulie, Stem Cells 13:393-403, 1995), and can be used in the present invention in a like manner as those disclosed herein. Thus, one of ordinary skill in the art can readily prepare polypeptides including one or more TOPK peptides and one or more of the non-TOPK peptides, or nucleic acids encoding such polypeptides, using standard procedures of molecular biology.

The above described linked peptides are referred to herein as "polytopes", i.e., groups of two or more potentially immunogenic or immune response stimulating peptides which can be joined together in various arrangements (e.g., concatenated, overlapping). The polytope (or nucleic acid encoding the polytope) can be administered in a standard immunization protocol, e.g., to animals, to test the effectiveness of the polytope in stimulating, enhancing and/or provoking an immune response.

The peptides can be joined together directly or via the use of flanking sequences to form polytopes, and the use of polytopes as vaccines is well known in the art (see, e.g., Thomson et al., Proc. Natl. Acad. Sci. USA 92(13):5845-5849, 1995; Gilbert et al., Nature Biotechnol. 15(12):1280-1284, 1997; Thomson et al., J. Immunol. 157(2):822-826, 1996; Tarn et al., J. Exp. Med. 171(1):299-306, 1990). Polytopes containing various numbers and combinations of epitopes can be prepared and tested for recognition by CTLs and for efficacy in increasing an immune response.

The peptides of the present invention can also be linked to other substances, so long as the resulting linked peptide retains the requisite CTL inducibility of the original peptide. Examples of suitable substances include, for example: peptides, lipids, sugar and sugar chains, acetyl groups, natural and synthetic polymers, etc. The peptides can contain modifications such as glycosylation, side chain oxidation, or phosphorylation, etc., provided the modifications do not destroy the biological activity of the original peptide. These kinds of modifications can be performed to confer additional functions (e.g., targeting function, and delivery function) or to stabilize the peptide.

For example, to increase the in vivo stability of a peptide, it is known in the art to introduce D-amino acids, amino acid mimetics or unnatural amino acids; this concept can also be adapted to the present peptides. The stability of a peptide can be assayed in a number of ways. For instance, peptidases and various biological media, such as human plasma and serum, can be used to test stability (see, e.g., Verhoef et al., Eur J Drug Metab Pharmacokin 1986, 11: 291-302).

Moreover, as noted above, among the modified peptides that are substituted, deleted inserted or added by 1, 2 or several amino acid residues, those having same or higher activity as compared to original peptides can be screened for or selected. The present invention, therefore, also provides the method of screening for or selecting modified peptides having same or higher activity as compared to originals. An illustrative method includes the steps of:

a: modifying (i.e., substituting, deleting, inserting or adding) at least one amino acid residue of a peptide of the present invention:

b: determining the activity of the peptide:

c: selecting the peptide having same or higher activity as compared to the original.

In preferred embodiments, the present invention provides a method of screening for a peptide having an ability to induce a CTL that has specific cytotoxic activity against a cell that presents a fragment derived from TOPK, wherein the method comprises the steps of:

(i) providing a candidate sequence consisting of an amino acid sequence modified by substituting, deleting, inserting and/or adding one, two or several amino acid residues to an original amino acid sequence, wherein the original amino acid sequence is selected from the group consisting of SEQ ID NOs: 2, 3, 6, 27, 28, 42, 45, 47, 50, 51, 53, 54, 62, 63, 64, 66, 71, 72 and 76;

(ii) selecting a candidate sequence that does not have substantial significant homology (or sequence identity) with the peptides derived from any known human gene products other than TOPK;

(iii) contacting a peptide consisting of the candidate sequence selected in step (ii) with an antigen presenting cell;

(iv) contacting the antigen presenting cell of step (iii) with a CD8 positive T cell; and (v) identifying the peptide of which CTL inducibility is same to or higher than a peptide consisting of the original amino acid sequence.

Herein, the activity to be assayed may include MHC binding activity, APC or CTL inducibility and cytotoxic activity. Preferably, the activity of the peptide to be assayed is CTL inducibility.

III. PREPARATION OF TOPK PEPTIDES

The peptides of the present invention can be prepared using well known techniques. For example, the peptides can be prepared synthetically, using recombinant DNA technology or chemical synthesis. The peptides of the present invention can be synthesized individually or as longer polypeptides including two or more peptides. The peptides can then be isolated i.e., purified or isolated so as to be substantially free of other naturally occurring host cell proteins and fragments thereof, or any other chemical substances.

The peptides of the present invention may contain modifications, such as glycosylation, side chain oxidation, or phosphorylation, provided the modifications do not destroy the biological activity of the original peptide. Other illustrative modifications include incorporation of one or more D-amino acids or other amino acid mimetics that can be used, for example, to increase the serum half life of the peptides.

Peptides of the present invention can be obtained through chemical synthesis based on the selected amino acid sequence. Examples of conventional peptide synthesis methods that can be adapted for the synthesis include:

(i) Peptide Synthesis, Interscience, New York, 1966;
(ii) The Proteins, Vol. 2, Academic Press, New York, 1976;
(iii) Peptide Synthesis (in Japanese), Maruzen Co., 1975;
(iv) Basics and Experiment of Peptide Synthesis (in Japanese), Maruzen Co., 1985;
(v) Development of Pharmaceuticals (second volume) (in Japanese), Vol. 14 (peptide synthesis), Hirokawa, 1991;
(vi) WO99/67288; and
(vii) Barany G. & Merrifield R. B., Peptides Vol. 2, "Solid Phase Peptide Synthesis", Academic Press, New York, 1980, 100-118.

Alternatively, the present peptides can be obtained adapting any known genetic engineering method for producing peptides (e.g., Morrison J, J Bacteriology 1977, 132: 349-51; Clark-Curtiss & Curtiss, Methods in Enzymology (eds. Wu et al.) 1983, 101: 347-62). For example, first, a suitable vector harboring a polynucleotide encoding the objective peptide in an expressible form (e.g., downstream of a regulatory sequence corresponding to a promoter sequence) is prepared and transformed into a suitable host cell. The host cell is then cultured to produce the peptide of interest. The peptide can also be produced in vitro adopting an in vitro translation system.

IV. POLYNUCLEOTIDES

The present invention also provides a polynucleotide that encodes any of the aforementioned peptides of the present invention. These include polynucleotides derived from the natural occurring TOPK gene (e.g., GenBank Accession No. NM_018492 (SEQ ID NO: 85)) as well as those having a conservatively modified nucleotide sequence thereof. Herein, the phrase "conservatively modified nucleotide sequence" refers to sequences which encode identical or essentially identical amino acid sequences. Due to the degeneracy of the genetic code, a large number of functionally identical nucleic acids encode any given protein. For instance, the codons GCA, GCC, GCG, and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a peptide also describes every possible silent variation of the nucleic acid. One of ordinary skill in the art will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a peptide is implicitly described in each disclosed sequence.

The polynucleotide of the present invention can be composed of DNA, RNA, and derivatives thereof. As is well known in the art, a DNA is suitably composed of bases such as A, T, C, and G, and T is replaced by U in an RNA. One of skill will recognize that non-naturally occurring bases may be included in polynucleotides, as well.

The polynucleotide of the present invention can encode multiple peptides of the present invention with or without intervening amino acid sequences in between. For example, the intervening amino acid sequence can provide a cleavage site (e.g., enzyme recognition sequence) of the polynucleotide or the translated peptides. Furthermore, the polynucleotide can include any additional sequences to the coding sequence encoding the peptide of the present invention. For example, the polynucleotide can be a recombinant polynucleotide that includes regulatory sequences required for the expression of the peptide or can be an expression vector (plasmid) with marker genes and such. In general, such recombinant polynucleotides can be prepared by the manipulation of polynucleotides through conventional recombinant techniques using, for example, polymerases and endonucleases.

Both recombinant and chemical synthesis techniques can be used to produce the polynucleotides of the present invention. For example, a polynucleotide can be produced by insertion into an appropriate vector, which can be expressed when transfected into a competent cell. Alternatively, a polynucleotide can be amplified using PCR techniques or expression in suitable hosts (see, e.g., Sambrook et al., Molecular Cloning: A Laboratory Manual, Cold Spring Harbor Laboratory, New York, 1989). Alternatively, a polynucleotide can be synthesized using the solid phase techniques, as described in Beaucage S L & Iyer R P, Tetrahedron 1992, 48: 2223-311; Matthes et al., EMBO J. 1984, 3: 801-5.

V. EXOSOMES

The present invention further provides intracellular vesicles, called exosomes, that present complexes formed between the peptides of the present invention and HLA antigens on their surface. Exosomes can be prepared, for example, using the methods detailed in Japanese Patent Application Kohyo Publications Nos. Hei 11-510507 and WO99/03499, and can be prepared using APCs obtained from patients who are subject to treatment and/or prevention. The exosomes of the present invention can be inoculated as vaccines, in a fashion similar to the peptides of the present invention.

The type of HLA antigens included in the complexes must match that of the subject requiring treatment and/or prevention. For example, in the Japanese population, HLA-A24 and HLA-A2, particularly HLA-A*2402 and HLA-A*0201 and HLA-A*0206, are prevalent and therefore would be appropriate for treatment of Japanese patients. The use of the HLA-A24 type that are highly expressed among the Japanese and Caucasian is favorable for obtaining effective results, and subtypes such as HLA-A*2402, HLA-A*0201 and HLA-A*0206 also find use. Typically, in the clinic, the type of HLA antigen of the patient requiring treatment is investigated in advance, which enables the appropriate selection of peptides having high levels of binding affinity to the particular antigen, or having CTL inducibility by antigen presentation. Furthermore, in order to obtain peptides having both high binding affinity and CTL inducibility, substitution, insertion, deletion and/or addition of 1, 2, or several amino acids can be performed based on the amino acid sequence of the naturally occurring TOPK partial peptide.

When the exosome of the present invention possess HLA-A24 type as an antigen, the peptides including the amino acid sequence selected from among SEQ ID NOs: 2 to 40 (especially SEQ ID NOs: 2, 3, 6, 27 and 28) have particular utility.

Alternatively, when the exosome of the present invention possess HLA-A2 type as an antigen, the peptides including the amino acid sequence selected from among SEQ ID NOs: 42 to 84 (especially SEQ ID NOs: 42, 45, 47, 50, 51, 53, 54, 62, 63, 64, 66, 71, 72 and 76) have particular utility.

In some embodiments, the exosomes of the present invention are exosomes that present a complex of the peptide of the present invention and HLA-A24 or HLA-A2 antigen on their surface. In typical embodiments, the exosome of the presents invention present a complex of a peptide having an amino acid sequence of SEQ ID NO: 2, 3, 6, 27 or 28 (or modified peptide thereof) and HLA-A24 on its surface. In other embodiments, the exosome of the present invention presents a complex of a peptide having an amino acid sequence of SEQ ID NO: 42, 45, 47, 50, 51, 53, 54, 62, 63, 64, 66, 71, 72 or 76 (or modified peptide thereof) and HLA-A2 on its surface.

VI. ANTIGEN-PRESENTING CELLS (APCS)

The present invention also provides isolated antigen-presenting cells (APCs) that present complexes formed between HLA antigens and the peptides of the present invention on its surface. The APCs can be derived from patients who are subject to treatment and/or prevention, and can be administered as vaccines by themselves or in combination with other drugs including the peptides, exosomes, or CTLs of the present invention.

The APCs are not limited to a particular kind of cells. Examples of APCs include, but are not limited to, dendritic cells (DCs), Langerhans cells, macrophages, B cells, and activated T cells, which are known to present proteinaceous antigens on their cell surface so as to be recognized by lymphocytes. Since DCs are representative APCs having the strongest CTL inducing activity among APCs, DCs can be preferably used as the APCs of the present invention.

For example, the APCs of the present invention can be obtained by inducing DCs from peripheral blood monocytes and then contacting (stimulating) them with the peptides of the present invention in vitro, ex vivo or in vivo. When the peptides of the present invention are administered to the subjects, APCs that present the peptides of the present invention are induced in the body of the subject. Herein, the phrase "inducing an APC" includes contacting (stimulating) an antigen-presenting cell with the peptides of the present invention, or introducing a polynucleotide encoding the peptide of the present invention into an antigen-presenting cell to have the APC present a complex formed between an HLA antigen and a peptide of the present invention on its surface. For example, the APCs of the present invention can be obtained by collecting APCs from a subject after administering one or more peptides of the present invention to the subject. Alternatively, the APCs of the present invention can be obtained by contacting APCs, which have been collected from a subject, with the peptide of the present invention.

The APCs of the present invention can be administered to a subject for inducing immune response against cancer in the subject by themselves or in combination with other drugs including the peptides, exosomes or CTLs of the present invention. For example, the ex vivo administration can include steps of:
 a: collecting APCs from a first subject,
 b: contacting the APCs of step a, with the peptide, and
 c: administering the APCs of step b to a second subject.

The first subject and the second subject can be the same individual, or may be different individuals. The APCs obtained by step b can be formulated and administered a vaccine for treating and/or preventing cancer, such as bladder cancer, breast cancer, cervical cancer, cholangiocellular carcinoma, CML, colorectal cancer, esophageal cancer, gastric cancer, diffuse-type gastric cancer, NSCLC, lymphoma, osteosarcoma, ovarian cancer, pancreatic cancer, prostate cancer, SCLC, soft tissue tumor and testicular tumor, but not limited thereto.

In the context of the present invention, one may utilize one or more peptides of the present invention for manufacturing a pharmaceutical composition for inducing an antigen-presenting cell. A method or process for manufacturing a pharmaceutical composition for inducing an antigen-presenting cell is provided herein and preferably includes the step of admixing or formulating the peptide of the invention with a pharmaceutically acceptable carrier.

The present invention also provides for the use of the peptide of the present invention for inducing an antigen-presenting cell.

According to an aspect of the present invention, the APCs of the present invention have CTL inducibility. In the context of the APCs, the phrase "CTL inducibility" refers to the ability of an APC to induce a CTL when contacted with a CD8 positive T cell. Further, "CTL inducibility" includes the ability of an APC to induce CTL activation, CTL proliferation, promote lysis of a target cell by a CTL, and to increase IFN-gamma production by a CTL. In particular, the APCs of the present invention have an ability to induce CTLs specific to TOPK.

Such APCs having CTL inducibility can be prepared by a method that includes the step of transferring a polynucleotide encoding the peptide of the present invention to APCs in vitro as well as the method mentioned above. The introduced polynucleotide can be in the form of DNAs or RNAs. Examples of methods for introduction include, without particular limitations, various methods conventionally performed in this field, such as lipofection, electroporation, and calcium phosphate method can be used. More specifically, it can be performed as described in Cancer Res 1996, 56: 5672-7; J Immunol 1998, 161: 5607-13; J Exp Med 1996, 184: 465-72; Published Japanese Translation of International Publication No. 2000-509281. By transferring the gene encoding the peptide of the present invention into APCs, the gene undergoes transcription, translation, and such in the cell, and then the obtained protein is processed by MHC Class I or Class II, and proceeds through a presentation pathway to present the peptides of the present invention. Alternatively, the APCs of the present invention can be prepared by a method which induces the step of contacting APCs with the peptide of the present invention.

In some embodiments, the APCs of the present invention are APCs that present complexes of HLA-A24 or HLA-A2 antigen and the peptide of the present invention on their surface. In typical embodiments, the APC of the present invention presents a complex of a peptide having an amino acid sequence of SEQ ID NO: 2, 3, 6, 27 or 28 (or modified peptide thereof) and HLA-A24 on its surface. In other embodiments, the APC of the present invention presents a complex of a peptide having an amino acid sequence of SEQ ID NO: 42, 45, 47, 50, 51, 53, 54, 62, 63, 64, 66, 71, 72 or 76 (or modified peptide thereof) and HLA-A2 on its surface.

VII. CYTOTOXIC T LYMPHOCYTES (CTLS)

A CTL induced against any one of the peptides of the present invention strengthens the immune response targeting cancer cells in vivo and thus can be used as vaccines, in a fashion similar to the peptides per se. Thus, the present invention provides isolated CTLs that are specifically induced or activated by any one of the peptides of the present invention.

Such CTLs can be obtained by (1) administering the peptide(s) of the present invention to a subject, (2) contacting (stimulating) subject-derived APCs, and CD8-positive T cells, or peripheral blood mononuclear leukocytes in vitro with the peptide(s) of the present invention, (3) contacting CD8-positive T cells or peripheral blood mononuclear leukocytes in vitro with the APCs or exosomes presenting a complex of an HLA antigen and the peptide of the present invention on its surface, or (4) introducing a polynucleotide/polynucleotides encoding T cell receptor (TCR) subunits that can form a TCR having an ability to bind to a complex of an HLA antigen and the peptide of the present invention on a cell surface. Such APCs or exosomes for the method of (3) can be prepared by the methods described above. Details of the method of (4) is described bellow in section "VIII. T Cell Receptor (TCR)".

The CTLs of the present invention can be derived from patients who are subject to treatment and/or prevention, and can be administered by themselves or in combination with other drugs including the peptides, APC or exosomes for the purpose of regulating effects. The obtained CTLs act specifically against target cells presenting the peptides of the present invention, for example, the same peptides used for induction. The target cells can be cells that endogenously express TOPK, such as cancer cells, or cells that are transfected with the TOPK gene; and cells that present a peptide of the present invention on the cell surface due to stimulation by the peptide can also serve as targets of activated CTL attack.

In some embodiments, the CTLs of the present invention can recognize cells presenting complexes of an HLA-A24 or HLA-A2 antigen and the peptide of the present invention on their surface. In the context of CTLs, the phrase "recognize a cell" refers to binding a complex of an HLA-A24 or HLA-A2 antigen and the peptide of the present invention on the cell surface via its TCR and showing specific cytotoxic activity against the cell. Herein, "specific cytotoxic activity" refers to showing cytotoxic activity against the cell presenting a complex of an HLA-A24 or HLA-A2 antigen and the peptide of the present invention but not other cells. Accordingly, the CTLs that show specific cytotoxic activity against a cell presenting the peptide of the present invention are included in the present invention.

In typical embodiments, the CTL of the present invention can recognize a cell presenting a peptide having an amino acid sequence of SEQ ID NO: 2, 3, 6, 27 or 28 (or modified peptide thereof) via an HLA-A24. In preferred embodiments, such CTL of the present invention can recognize a cell expressing TOPK and an HLA-A24 (e.g., HLA-A24 positive cancer cell).

In other embodiments, the CTL of the present invention can recognize a cell presenting a peptide having an amino acid sequence of SEQ ID NO: 42, 45, 47, 50, 51, 53, 54, 62, 63, 64, 66, 71, 72 or 76 (or modified peptide thereof) via an HLA A2. In preferred embodiments, such CTL of the present invention can recognize a cell expressing TOPK and an HLA-A2 (e.g., HLA-A2 positive cancer cell).

VIII. T CELL RECEPTOR (TCR)

The present invention also provides a composition that includes one or more polynucleotides encoding polypeptides that are capable of forming a subunit of a T cell receptor (TCR), and methods of using the same. Such TCR subunits have the ability to form TCRs that confer specificity to T cells against tumor cells expressing TOPK. By using known methods in the art, the polynucleotide encoding each of alpha- and beta-chains as the TCR subunits of the CTL induced with the peptides of the present invention can be identified (WO2007/032255 and Morgan et al., J Immunol, 171, 3288 (2003)). For example, the PCR method is preferred to analyze the TCR. The PCR primers for the analysis can be, for example, 5'-R primers (5'-gtctaccaggcattcgcttcat-3') (SEQ ID NO: 87) as a 5' side primer, and 3-TRa-C primers (5'-tcagctggaccacagccgcagcgt-3') (SEQ ID NO: 88) specific to TCR alpha chain C region, 3-TRb-C1 primers (5'-tcagaaatcctttctcttgac-3') (SEQ ID NO: 89) specific to TCR beta chain C1 region or 3-TRbeta-C2 primers (5'-ctagcctctggaatcctttctctt-3') (SEQ ID NO: 90) specific to TCR beta chain C2 region as 3' side primers, but not limited thereto. The derivative TCRs can bind target cells presenting the TOPK peptide with high avidity, and optionally mediate efficient killing of target cells presenting the TOPK peptide of the present invention in vivo and in vitro.

The polynucleotide/polynucleotides encoding the TCR subunits (i.e., the polynucleotide encoding both of the TCR subunits or polynucleotides encoding each of TCR subunits) can be incorporated into suitable vectors, e.g., retroviral vectors. These vectors are well known in the art. The polynucleotides or the vectors including them usefully can be transferred into a T cell (e.g., CD8-positive T cell), for example, a T cell from a patient. Advantageously, the present invention provides an off-the-shelf composition allowing rapid modification of a patient's own T cells (or those of another mammal) to rapidly and easily produce modified T cells having excellent cancer cell killing properties.

Specific TCRs against the peptides of the present invention should be capable of specifically recognizing a complex of a peptide of the present invention and an HLA antigen, giving a T cell specific activity against the target cell presenting a complex of the peptide of the present invention and an HLA antigen when the TCR is expressed on the surface of the T cell. The requisite activity can be confirmed by any known methods that CTL prepared by introducing the polypeptide(s) encoding such TCR subunits can be specifically recognize such target cells. Preferred examples of such method include, for example, tetramer analysis using HLA molecules and the peptides of the present invention, and ELISPOT assay. By ELISPOT assay, it can be confirmed that CTLs prepared by the method as describe above can specifically recognize the target cells, and that the signals generated by such recognition by transmitted intracellularly. Furthermore, it can be confirmed by a known method that CTLs prepared by the method described above have specific cytotoxic activity against the target cells. Examples of such methods includes, for example, chromium release assay using cells expressing both of TOPK and HLA-A24 or HLA-A2.

In one aspect, the present invention provides CTLs that are prepared by transduction with the polypeptide/polypeptides encoding the TCR subunit polypeptides (i.e., the polynucleotide encoding both of the TCR subunits or polynucleotides encoding each of TCR subunits), wherein the TCR formed by such TCR subunits can bind to a complex of the TOPK peptide having an amino acid sequence selected from among SEQ ID NOs: 2 to 40 and an HLA-A24 antigen on cell surface, or can bind to a complex of the TOPK peptide having an amino acid sequence selected from among SEQ ID NOs: 42 to 84 and an HLA-A2 antigen on cell surface.

The transduced CTLs are capable of homing to cancer cells in vivo, and can be expanded by well known culturing methods in vitro (e.g., Kawakami et al., J. Immunol., 142, 3452-3461 (1989)). The CTLs of the present invention can be used to form an immunogenic composition useful in either or both of the treatment and the prevention of cancer in a patient in need of therapy or protection (See WO2006/031221 the contents of which are incorporated by reference herein).

IX. PHARMACEUTICAL AGENTS OR COMPOSITIONS

Since TOPK expression is specifically elevated in cancers, examples of which include, but are not necessarily limited to, AML, bladder cancer, breast cancer, cervical cancer, cholangiocellular carcinoma, colorectal cancer, diffuse-type gastric cancer, NSCLC, lymphoma, osteosarcoma, prostate cancer, renal carcinoma, SCLC and soft tissue tumor as compared with normal tissue, the peptides or polynucleotides of the present invention may be used to induce an immune response against cancer and thus serve to treat and/or prevent cancer and/or to prevent a metastatic or post-operative recurrence thereof. Thus, the present invention provides pharmaceutical compositions or agents formulated for the treatment and/or prophylaxis of cancer, and/or for the prevention of a postoperative recurrence thereof, such compositions or agents including one or more of the peptides, or polynucleotides of the present invention as one or more active ingredients. Alternatively, the peptides of the present invention can be expressed on the surface of any of the foregoing exosomes or cells, such as APCs, for the use as pharmaceutical compositions or agents. In addition, the aforementioned CTLs which target any one of the peptides of the present invention can also be used as the active ingredient of the present pharmaceutical compositions or agents.

Accordingly, the present invention provides agents or compositions including at least one active ingredient selected from among:

(a) one or more peptides of the present invention;

(b) one or more polynucleotides encoding such a peptide of the present invention in an expressible form;

(c) one or more APCs or an exosomes of the present invention; and (d) one or more CTLs of the present invention.

The pharmaceutical compositions or agents of the present invention also find use as a vaccine. In the context of the present invention, the phrase "vaccine" (also referred to as an "immunogenic composition") refers to an agent or composition that has the function to improve, enhance and/or induce anti-tumor immunity upon inoculation into an animal. In other words, the present invention provides the pharmaceutical agents or compositions for inducing an immune response against cancer in a subject.

The pharmaceutical compositions or agents of the present invention can be used to treat and/or prevent cancer and/or prevent a postoperative or metastatic recurrence thereof in subjects or patients. Examples of such subjects include humans as well as other mammals including, but not limited to, mice, rats, guinea-pigs, rabbits, cats, dogs, sheep, goats, pigs, cattle, horses, monkeys, baboons, and chimpanzees, particularly commercially important animals or domesticated animals. In some embodiments, the pharmaceutical agents or compositions of the present invention can be formulated for the administration to a subject whose HLA antigen is HLA-A24 or HLA-A2.

In another embodiment, the present invention also provides the use of an active ingredient in the manufacture of a pharmaceutical composition or agent for treating and/or preventing cancer or tumor, and/or preventing a post-operative recurrence thereof, said active ingredient selected from among:

(a) a peptide of the present invention;

(b) a polynucleotide encoding such a peptide of the present invention in an expressible form;

(c) an APC presenting a peptide of the present invention on its surface;

(d) an exosome presenting a peptide of the present invention on its surface; and (e) a cytotoxic T cell of the present invention.

Alternatively, the present invention further provides an active ingredient for use in either or both of the treatment and prevention of cancers or tumors, and/or prevention of a post-operative recurrence thereof, said active ingredient selected from among:

(a) a peptide of the present invention;

(b) a polynucleotide encoding such a peptide of the present invention in an expressible form;

(c) an APC presenting a peptide of the present invention on its surface;

(d) an exosome presenting a peptide of the present invention on its surface; and (e) a cytotoxic T cell of the present invention.

Alternatively, the present invention further provides a method or process for the manufacture of a pharmaceutical composition or agent for treating and/or preventing a cancer or tumor, and/or preventing of a post-operative recurrence thereof, wherein the method or process includes the step of formulating a pharmaceutically or physiologically acceptable carrier with an active ingredient selected from among:

(a) a peptide of the present invention;
(b) a polynucleotide encoding such a peptide of the present invention in an expressible form;
(c) an APC presenting a peptide of the present invention on its surface;
(d) an exosome presenting a peptide of the present invention on its surface; and
(e) a cytotoxic T cell of the present invention.

In another embodiment, the present invention also provides a method or process for the manufacture of a pharmaceutical composition or agent for treating and/or preventing a cancer or tumor, and/or preventing of a post-operative recurrence thereof, wherein the method or process includes the steps of admixing an active ingredient with a pharmaceutically or physiologically acceptable carrier, wherein the active ingredient is selected from among:

(a) a peptide of the present invention;
(b) a polynucleotide encoding such a peptide of the present invention in an expressible form;
(c) an APC presenting a peptide of the present invention on its surface;
(d) an exosome presenting a peptide of the present invention on its surface; and
(e) a cytotoxic T cell of the present invention.

In another embodiment, the present invention also provides a method for treating and/or preventing cancer or tumor, and/or preventing a post-operative recurrence thereof, wherein the method comprises the step of administering to a subject at least one active ingredient selected from among:

(a) a peptide of the present invention;
(b) a polynucleotide encoding such a peptide of the present invention in an expressible form;
(c) an APC presenting a peptide of the present invention on its surface;
(d) an exosome presenting a peptide of the present invention on its surface; and
(e) a cytotoxic T cell of the present invention.

According to the present invention, peptides having an amino acid sequence selected from among SEQ ID NOs: 2 to 40 can be HLA-A24 restricted epitope peptides. Among these peptides, peptides having an amino acid sequence selected from among SEQ ID NOs: 2, 3, 6, 27 and 28 can effectively induce potent and specific immune response against cancer expressing HLA-A24 and TOPK in a subject. Likewise, the peptides having an amino acid sequence selected from among SEQ ID NOs: 42 to 84 can be HLA-A2 restricted epitope peptides. Among these peptides, peptides having an amino acid sequence selected from among SEQ ID NOs: 42, 45, 47, 50, 51, 53, 54, 62, 63, 64, 66, 71, 72 and 76 can effectively induce potent and specific immune response against cancer expressing HLA-A2 and TOPK in a subject. Therefore, the pharmaceutical compositions or agents which include any of peptides with the amino acid sequence selected from among SEQ ID NOs: 2 to 40 (especially SEQ ID NOs: 2, 3, 6, 27 and 28) and modified peptides thereof are particularly suited for the administration to subjects whose HLA antigen is HLA-A24. Likewise, the pharmaceutical compositions or agents which include any of peptides with the amino acid sequence selected from among SEQ ID NOs: 42 to 84 (especially SEQ ID NOs: 42, 45, 47, 50, 51, 53, 54, 62, 63, 64, 66, 71, 72 and 76) modified peptides thereof are particularly suited for the administration to subjects whose HLA antigen is HLA-A2. The same applies to pharmaceutical compositions or agents that contain polynucleotides encoding any of these peptides (i.e., the polynucleotides of the present invention).

Cancers to be treated by the pharmaceutical compositions or agents of the present invention include all kinds of cancers wherein TOPK is involved, including, but not limited to, AML, bladder cancer, breast cancer, cervical cancer, cholangiocellular carcinoma, colorectal cancer, diffuse-type gastric cancer, NSCLC, lymphoma, osteosarcoma, prostate cancer, renal carcinoma, SCLC and soft tissue tumor.

The pharmaceutical compositions or agents of the present invention can contain in addition to the aforementioned active ingredients, other peptides that have the ability to induce CTLs against cancerous cells, other polynucleotides encoding the other peptides, other cells that present the other peptides, and the like. Examples of such "other" peptides having the ability to induce CTLs against cancerous cells include, but are not limited to, cancer specific antigens (e.g., identified TAAs).

If necessary, the pharmaceutical compositions or agents of the present invention can optionally include other therapeutic substances as an additional active ingredient, so long as the substance does not inhibit the anti-tumoral effect of the active ingredient, e.g., any of the peptides of the present invention. For example, formulations can include anti-inflammatory substances, pain killers, chemotherapeutics, and the like. In addition to including other therapeutic substances in the medicament itself, the medicaments of the present invention can also be administered sequentially or con-currently with one or more other pharmacologic compositions. The amounts of medicament and pharmacologic composition depend, for example, on what type of pharmacologic composition(s) is/are used, the disease being treated, and the schedule and routes of administration.

Those of skill in the art will recognize that, in addition to the ingredients particularly mentioned herein, the pharmaceutical compositions or agents of the present invention can include other substances conventional in the art having regard to the type of formulation in question (e.g., fillers, binders, diluents, excipients, etc.).

In one embodiment of the present invention, the pharmaceutical compositions or agents of the present invention can be included in articles of manufacture and kits containing materials useful for treating the pathological conditions of the disease to be treated, e.g., cancer. The article of manufacture can include a container of any of the present pharmaceutical compositions or agents with a label. Suitable containers include bottles, vials, and test tubes. The containers can be formed from a variety of materials, such as glass or plastic. The label on the container should indicate the composition or agent is used for treating or prevention of one or more conditions of the disease. The label can also indicate directions for administration and so on.

In addition to the container described above, a kit including a pharmaceutical composition or agent of the present invention can optionally further include a second container housing a pharmaceutically-acceptable diluent. It can further include other materials desirable from a commercial and user standpoint, including other buffers, diluents, filters, needles, syringes, and package inserts with instructions for use.

The pharmaceutical compositions or agents can, if desired, be packaged in a pack or dispenser device which can contain one or more unit dosage forms containing the active ingredient. The pack can, for example, include metal or plastic foil, such as a blister pack. The pack or dispenser device can be accompanied by instructions for administration.

(1) Pharmaceutical Agents or Compositions Containing Peptides as the Active Ingredient:

The peptides of this invention can be administered directly as a pharmaceutical composition or agent, or if necessary, may be formulated by conventional formulation methods. In the latter case, in addition to the peptides of this invention, carriers, excipients, and such that are ordinarily used for drugs can be included as appropriate without particular limitations. Examples of such carriers include, but are not limited to, sterilized water, physiological saline, phosphate buffer, culture fluid and such. Furthermore, the pharmaceutical compositions or agents can contain as necessary, stabilizers, suspensions, preservatives, surfactants and such. The pharmaceutical compositions or agents of the present invention can be used for anticancer purposes.

The peptides of the present invention can be prepared as a combination composed of two or more of peptides of the present invention, to induce CTLs in vivo. The peptide combination can take the form of a cocktail or can be conjugated to each other using standard techniques. For example, the peptides can be chemically linked or expressed as a single fusion polypeptide sequence. The peptides in the combination can be the same or different. By administering the peptides of the present invention, the peptides are presented at a high density by the HLA antigens on APCs, then CTLs that specifically react toward the complex formed between the displayed peptide and the HLA antigen are induced. Alternatively, APCs (e.g., DCs) are removed from subjects and then stimulated by the peptides of the present invention to obtain APCs that present any of the peptides of the present invention on their cell surface. These APCs are readministered to the subjects to induce CTLs in the subjects, and as a result, aggressiveness towards the tumor-associated endothelium can be increased.

The pharmaceutical compositions or agents for the treatment and/or prevention of cancer containing any peptide of the present invention as the active ingredient can also include an adjuvant known to effectively establish cellular immunity. Alternatively, the pharmaceutical compositions or agents can be administered with other active ingredients, or administered by formulation into granules. An adjuvant refers to a compound that enhances the immune response against the protein when administered together (or successively) with the protein having immunological activity. Adjuvants contemplated herein include those described in the literature (Clin Microbiol Rev 1994, 7: 277-89). Examples of suitable adjuvants include, but are not limited to, aluminum phosphate, aluminum hydroxide, alum, cholera toxin, *salmonella* toxin, IFA (Incomplete Freund's adjuvant), CFA (Complete Freund's adjuvant), ISCOMatrix, GM-CSF, CpG, O/W emulsion and the like.

Furthermore, liposome formulations, granular formulations in which the peptide is bound to few-micrometers diameter beads, and formulations in which a lipid is bound to the peptide may be conveniently used.

In another embodiment of the present invention, the peptides of the present invention may also be administered in the form of a pharmaceutically acceptable salt. Examples of preferred salts include salts with an alkali metal, salts with a metal, salts with an organic base, salts with an organic acid (e.g., acetic acid, formic acid, propionic acid, fumaric acid, maleic acid, succinic acid, tartaric acid, citric acid, malic acid, oxalic acid, benzoic acid, methanesulfonic acid and so on) and salts with an inorganic acid (e.g., hydrochloric acid, phosphoric acid, hydrobromic acid, sulfuric acid and so on). As used herein, the phrase "pharmaceutically acceptable salt" refers to those salts that retain the biological effectiveness and properties of the compound and which are obtained by reaction with inorganic acids or bases such as hydrochloric acid, hydrobromic acid, sulfuric acid, nitric acid, phosphoric acid, methanesulfonic acid, ethanesulfonic acid, p-toluenesulfonic acid, salicylic acid and the like.

In some embodiments, the pharmaceutical compositions or agents of the present invention may further include a component that primes CTLs. Lipids have been identified as substances capable of priming CTLs in vivo against viral antigens. For example, palmitic acid residues can be attached to the epsilon- and alpha-amino groups of a lysine residue and then linked to a peptide of the present invention. The lipidated peptide can then be administered either directly in a micelle or particle, incorporated into a liposome, or emulsified in an adjuvant. As another example of lipid priming of CTL responses, *E. coli* lipoproteins, such as tripalmitoyl-S-glycerylcysteinyl-seryl-serine (P3CSS) can be used to prime CTLs when covalently attached to an appropriate peptide (see, e.g., Deres et al., Nature 1989, 342: 561-4).

Examples of suitable methods of administration include, but are not necessarily limited to, oral, intradermal, subcutaneous, intramuscular, intraosseous, peritoneal, and intravenous injection, or such, and systemic administration or local administration to the vicinity of the targeted sites (i.e., direct injection). The administration can be performed by single administration or boosted by multiple administrations. The dose of the peptides of the present invention can be adjusted appropriately according to the disease to be treated, age of the patient, weight, method of administration, and such, and is ordinarily 0.001 mg to 1000 mg, for example, 0.01 mg to 100 mg, for example, 0.1 mg to 10 mg, for example, 0.5 mg to 5 mg, and can be administered once in a few days to few months. One skilled in the art can readily determine suitable and optimal dosages.

(2) Pharmaceutical Agents or Compositions Containing Polynucleotides as Active Ingredient:

The pharmaceutical compositions or agents of the present invention can also contain nucleic acids encoding the peptides of the present invention in an expressible form. Herein, the phrase "in an expressible form" means that the polynucleotide, when introduced into a cell, will be expressed in vivo as a polypeptide that induces anti-tumor immunity. In an illustrative embodiment, the nucleic acid sequence of the polynucleotide of interest includes regulatory elements necessary for expression of the polynucleotide. The polynucleotide(s) can be equipped so to achieve stable insertion into the genome of the target cell (see, e.g., Thomas K R & Capecchi M R, Cell 1987, 51: 503-12 for a description of homologous recombination cassette vectors). See, e.g., Wolff et al., Science 1990, 247: 1465-8; U.S. Pat. Nos. 5,580,859; 5,589,466; 5,804,566; 5,739,118; 5,736,524; 5,679,647; and WO 98/04720. Examples of DNA-based delivery technologies include "naked DNA", facilitated (bupivacaine, polymers, peptide-mediated) delivery, cationic lipid complexes, and particle-mediated ("gene gun") or pressure-mediated delivery (see, e.g., U.S. Pat. No. 5,922, 687).

The peptides of the present invention can also be expressed by viral or bacterial vectors. Examples of expression vectors include attenuated viral hosts, such as vaccinia or fowlpox. This approach involves the use of vaccinia virus, e.g., as a vector to express nucleotide sequences that encode the peptide. Upon introduction into a host, the recombinant vaccinia virus expresses the immunogenic peptide, and thereby elicits an immune response. Vaccinia vectors and methods useful in immunization protocols are described in, e.g., U.S. Pat. No. 4,722,848. Another vector is BCG (Bacille Calmette Guerin). BCG vectors are described in Stover et al., Nature 1991, 351: 456-60. A wide variety of other vectors useful for therapeutic administration or immunization e.g., adeno and adeno-associated virus vectors, retroviral vectors, *Salmonella typhi* vectors, detoxified anthrax toxin vectors, and the like, will be apparent. See, e.g., Shata et al., Mol Med Today 2000, 6: 66-71; Shedlock et al., J Leukoc Biol 2000, 68: 793-806; Hipp et al., In Vivo 2000, 14: 571-85.

Delivery of a polynucleotide into a patient can be either direct, in which case the patient is directly exposed to a polynucleotide-carrying vector, or indirect, in which case, cells are first transformed with the polynucleotide of interest in vitro, then the cells are transplanted into the patient. Theses two approaches are known, respectively, as in vivo and ex vivo gene therapies.

For general reviews of the methods of gene therapy, see Goldspiel et al., Clinical Pharmacy 1993, 12: 488-505; Wu and Wu, Biotherapy 1991, 3: 87-95; Tolstoshev, Ann Rev Pharmacol Toxicol 1993, 33: 573-96; Mulligan, Science 1993, 260: 926-32; Morgan & Anderson, Ann Rev Biochem 1993, 62: 191-217; Trends in Biotechnology 1993, 11(5): 155-215). Methods commonly known in the art of recombinant DNA technology that are applicable to the present invention are described by Ausubel et al. in Current Protocols in Molecular Biology (John Wiley & Sons, NY, 1993); and Krieger in Gene Transfer and Expression, A Laboratory Manual (Stockton Press, NY, 1990).

Like administration of peptides, administration of polynucleotides may be performed by oral, intradermal, subcutaneous, intravenous, intramuscular, intraosseous, and/or peritoneal injection, or such, and via systemic administration or local administration to the vicinity of the targeted sites finds use. The administration can be performed by single administration or boosted by multiple administrations. The dose of the polynucleotide in the suitable carrier or cells transformed with the polynucleotide encoding the peptides of the present invention can be adjusted appropriately according to the disease to be treated, age of the patient, weight, method of administration, and such, and is ordinarily 0.001 mg to 1000 mg, for example, 0.01 mg to 100 mg, for example, 0.1 mg to 10 mg, for example, 0.5 mg to 5 mg, and can be administered once every a few days to once every few months. One skilled in the art can readily determine suitable and optimal dosages.

X. METHODS OF USING THE PEPTIDES, POLYNUCLEOTIDE, EXOSOMES, APCS AND CTLS

The peptides and polynucleotides of the present invention can be used for preparing or inducing APCs and CTLs. The exosomes and APCs of the present invention can be also used for preparing or inducing CTLs. The peptides, polynucleotides, exosomes and APCs can be used in combination with any other compounds so long as the additional compounds do not inhibit CTL inducibility. Thus, any of the aforementioned pharmaceutical compositions or agents of the present invention can be used for preparing or inducing CTLs. In addition thereto, those including the peptides or polynucleotides can be also used for preparing or inducing APCs as discussed below.

(1) Method of Inducing Antigen-Presenting Cells (APCs)

The present invention provides methods of inducing APCs with high CTL inducibility using the peptides or polynucleotides of the present invention.

The methods of the present invention include the step of contacting APCs with the peptides of the present invention in vitro, ex vivo or in vivo. For example, the method of inducing APCs ex vivo can include steps of:

a: collecting APCs from a subject: and
 b: contacting the APCs of step a with the peptide of the present invention.

The APCs are not limited to a particular kind of cells. Examples of APCs include, but are not limited to, DCs, Langerhans cells, macrophages, B cells, and activated T cells, which are known to present proteinaceous antigens on their cell surface so as to be recognized by lymphocytes. Preferably, DCs can be used since they have the strongest CTL inducibility among APCs. Any one of peptides of the present invention can be used by itself or in combination with other peptides of the present invention or CTL-inducible peptides derived from TAAs other than TOPK.

On the other hand, when the peptides of the present invention are administered to a subject, the APCs are contacted with the peptides in vivo, and consequently, the APCs with CTL inducibility are induced in the body of the subject. Thus, the method of the present invention may include the step of administering a peptide of the present invention to a subject to induce an APC with CTL inducibility in the body of the subject. Similarly, when the polynucleotides of this invention are administered to a subject in an expressible form, the peptides of the present invention are expressed and contacted with APCs in vivo, and consequently, the APCs with CTL inducibility are induced in the body of the subject. Thus, the methods of the present invention may include the step of administering a polynucleotide of the present invention to a subject to induce an APC with CTL inducibility in the body of the subject. The phrase "expressible form" was described above in section "IX. Pharmaceutical Agents or Compositions (2) Pharmaceutical Agents or Compositions Containing Polynucleotides as the Active Ingredient".

Alternatively, the methods of the present invention may include the step of introducing a polynucleotide encoding the peptide of the present invention into an APC to induce an APC with CTL inducibility. For example, the method can include steps of:

a: collecting APCs from a subject: and
 b: introducing a polynucleotide encoding the peptide of the present invention into the APC of step a.

Step b can be performed as described above in section "VI. Antigen-Presenting Cells".

Alternatively, the methods of the present invention may include the step of preparing an antigen-presenting cell (APC) that can specifically induce CTL activity against TOPK, via one of the following steps:

(a) contacting an APC with a peptide of the present invention in vitro, ex vivo or in vivo; and
 (b) introducing a polynucleotide encoding a peptide of the present invention into an APC.

Alternatively, the methods of the present invention may serve to induce an APC having CTL inducibility, such methods including a step selected from among:

(a) contacting an APC with the peptide of the present invention;

(b) introducing the polynucleotide encoding the peptide of the present invention into an APC.

In a preferred embodiment, the present invention provides the method of inducing or preparing an APC having CTL inducibility, such method including one of the following steps:

(a) contacting an APC expressing HLA-A24 with a peptide having an amino acid sequence selected from among SEQ ID NOs: 2 to 40 (especially SEQ ID NOs: 2, 3, 6, 27 and 28) or modified peptide thereof in vitro, ex vivo or in vivo; and (b) introducing a polynucleotide encoding a peptide having an amino acid sequence selected from among SEQ ID NOs: 2 to 40 (especially SEQ ID NOs: 2, 3, 6, 27 and 28) or modified peptide thereof into an APC expressing HLA-A2.

APCs induced by the above method present such peptides via HLA-A24 on their surface, and can induce CTLs having specific cytotoxic activity against cells expressing HLA-A24 and TOPK.

In another embodiment, the present invention provides the method of inducing or preparing an APC having CTL inducibility, such method including one of the following steps:

(a) contacting an APC expressing HLA-A2 with a peptide having an amino acid sequence selected from among SEQ ID NOs: 42 to 84 (especially SEQ ID NOs: 42, 45, 47, 50, 51, 53, 54, 62, 63, 64, 66, 71, 72 and 76) or modified peptide thereof in vitro, ex vivo or in vivo; and (b) introducing a polynucleotide encoding a peptide having an amino acid sequence selected from among SEQ ID NOs: SEQ ID NOs: 42 to 84 (especially SEQ ID NOs: 42, 45, 47, 50, 51, 53, 54, 62, 63, 64, 66, 71, 72 and 76) or modified peptide thereof into an APC expressing HLA-A2.

APCs induced by the above method present such peptides via HLA-A2 on their surface, and can induce CTLs having specific cytotoxic activity against cells expressing HLA-A2 and TOPK.

The methods of the present invention can be carried out in vitro, ex vivo or in vivo. Preferably, the methods of the present invention can be carried out in vitro or ex vivo. APCs used for induction of APCs having CTL inducibility can be preferably APCs expressing HLA-A24 or HLA-A2 antigen. Such APCs can be prepared by the methods well-known in the arts from peripheral blood mononuclear cells (PBMCs) obtained from a subject whose HLA antigen is HLA-A24 or HLA-A2. The APCs induced by the method of the present invention can be APCs that present a complex of the peptide of the present invention and HLA antigen (HLA A24 or HLA-A2 antigen) in its surface. When APCs induced by the method of the present invention are administered to a subject in order to induce immune responses against cancer in the subject, the subject is preferably the same one from whom APCs are derived. However, the subject may be a different one from the APC donor so long as the subject has the same HLA type with the APC donor.

In another embodiment, the present invention provide agents or compositions for use in inducing an APC having CTL inducibility, and such agents or compositions include one or more peptides or polynucleotides of the present invention.

In another embodiment, the present invention provides the use of the peptide of the present invention or the polynucleotide encoding the peptide in the manufacture of an agent or composition formulated for inducing APCs.

Alternatively, the present invention further provides the peptide of the present invention or the polypeptide encoding the peptide for use in inducing an APC having CTL inducibility.

(2) Method of Inducing CTLs

The present invention also provides methods for inducing CTLs using the peptides, polynucleotides, exosomes or APCs of the present invention.

The present invention also provides methods for inducing CTLs using a polynucleotide/polynucleotides encoding polypeptides (i.e., TCR subunits) that are capable of forming a T cell receptor (TCR) that is capable of recognizing a complex of the peptide of the present invention and an HLA antigen. Preferably, the methods for inducing CTLs include at least one step selected from among:

a: contacting a CD8-positive T cell with an antigen-presenting cell that presents on its surface a complex of an HLA antigen and a peptide of the preset invention;

b: contacting a CD8-positive T cell with an exosome that presents on its surface a complex of an HLA antigen and a peptide of the present invention; and c: introducing a polynucleotide/polynucleotides encoding polypeptides that are capable of forming a TCR that is capable of recognizing a complex of a peptide of the present invention and an HLA antigen into a CD8-positive T cell.

When the peptides, polynucleotides, APCs, or exosomes of the present invention are administered to a subject, CTLs are induced in the body of the subject, and the strength of the immune response targeting the cancer cells expressing TOPK is enhanced. Thus, instead of the step aforementioned step, the methods of the present invention may include the step of administering the peptides, polynucleotides, APCs or exosomes of the present invention to a subject.

Alternatively, CTLs can be also induced by using them ex vivo or in vivo, and after inducing CTLs, the activated CTLs are returned to the subject. For example, the method can include steps of:

a: collecting APCs from subject:

b: contacting the APCs of step a, with the peptide of the present invention: and c: co-culturing the APCs of step b with CD8-positive T cells.

The APCs to be co-cultured with the CD8-positive T cells in above step c can also be prepared by transferring a polynucleotide of the present invention into APCs as described above in section "VI. Antigen-Presenting Cells", although the present invention is not limited thereto and thus encompasses any APCs that effectively present on its surface a complex of an HLA antigen and a peptide of the present invention.

One may optionally utilize an exosome that presents on its surface a complex of an HLA antigen and the peptide of the present invention instead of the afore-mentioned APCs. Namely, the present invention can includes the step of co-culturing exosomes presenting on its surface a complex of an HLA antigen and the peptide of the present invention. Such exosomes can be prepared by the methods described above in section "V. Exosomes". Suitable APCs and exosomes for the method of the present invention present a complex of the peptide of the present invention and HLA-A24 or HLA-A2 on its surface. For example, an APC or exosome that present a complex of an HLA-A24 and a peptide having an amino acid sequence selected from among SEQ ID NOs: 2, 3, 6, 27 and 28 (or modified peptide thereof) on its surface can be preferably utilize for inducing a CTL having specific cytotoxic activity against a cell expressing HLA-A24 and TOPK. Likewise, an APC or exosome that present a complex of an HLA-A2 and a peptide having an amino acid sequence selected from among SEQ ID NOs: 42, 45, 47, 50, 51, 53, 54, 62, 63, 64, 66, 71, 72 and 76 (or modified peptide thereof) on its surface can be preferably utilize for inducing a CTL having specific cytotoxic activity against a cell expressing HLA-A2 and TOPK.

Furthermore, the CTL of the present invention can be induced by introducing into a CD8 positive T cell a polynucleotide/polynucleotides encoding the TCR subunits, wherein the TCR formed by such TCR subunits is capable of binding to a complex of an HLA antigen and the peptide of the invention on a cell surface. Such transduction can be performed as described above in section "VIII. T Cell Receptor (TCR)".

The methods of the present invention can be carried out in vitro, ex vivo or in vivo. Preferably, the methods of the present invention can be carried out in vitro or ex vivo. CD8-positive T cells used for induction of CTLs can be prepared by well-known methods in the art from PBMCs obtained from a subject. In preferred embodiments, the donor for CD8-positive T cells can be a subject whose HLA antigen is HLA-A24 or HLA-A2. The CTLs induced by the methods of the present invention can be CTLs that can recognize cells presenting a complex of the peptide of the present invention and HLA antigen on its surface. Such CTLs can show specific cytotoxic activity against cells that present the peptide of the present invention on its surface, and therefore, can show specific cytotoxic activity against cells expressing TOPK (e.g., cancer cells). When CTLs induced by the method of the present invention are administered to a subject in order to induce immune responses against cancer in the subject, the subject is preferably the same one from whom CD8-positive T cells are derived. However, the subject may be a different one from the CD8-positive T cell donor so long as the subject has the same HLA type with the CD8-positive T cell donor.

In addition, the present invention provides a method or process for manufacturing a pharmaceutical composition or agent that induces CTLs, wherein the method includes the step of admixing or formulating the peptide of the present invention with a pharmaceutically acceptable carrier.

In another embodiment, the present invention provide an agent or composition for inducing a CTL, wherein the agent or composition comprises one or more peptide(s), one or more polynucleotide(s), or one o more APCs or exosomes of the present invention.

In another embodiment, the present invention provides the use of the peptide, the polynucleotide, or APC or exosome of the present invention in the manufacture of an agent or composition formulated for inducing a CTL.

Alternatively, the present invention further provides the peptide, the polynucleotide, or APC or exosome of the present invention for use in inducing a CTL.

(3) Methods of Inducing Immune Response

Moreover, the present invention provides methods of inducing immune response against diseases related to TOPK. Diseases contemplated include cancer, examples of which include, but are not limited to, AML, bladder cancer, breast cancer, cervical cancer, cholangiocellular carcinoma, colorectal cancer, diffuse-type gastric cancer, NSCLC, lymphoma, osteosarcoma, prostate cancer, renal carcinoma, SCLC and soft tissue tumor.

The methods of the present invention may include the step of administering agent(s) or composition(s) containing any of the peptides of the present invention or polynucleotides encoding them. Alternatively, the method of the present invention also includes the step of administering exosomes or APCs presenting any of the peptides of the present invention. For details, see the item of "IX. Pharmaceutical Agents or Compositions", particularly the part describing the use of the pharmaceutical compositions of the present invention as vaccines. In addition, the exosomes and APCs that can be employed for the present methods for inducing immune response are described in detail under the items of "V. Exosomes", "VI. Antigen-Presenting Cells (APCs)", and (1) and (2) of "X. Methods of Using the Peptides, Exosomes, APCs and CTLs", supra.

The present invention also provides a method or process for manufacturing a pharmaceutical composition or agent that induce an immune response against cancer, wherein the method may include the step of admixing or formulating a peptide or polynucleotide of the present invention with a pharmaceutically acceptable carrier.

Alternatively, the method of the present invention may include the step of administrating a vaccine or a pharmaceutical composition or agent of the present invention that contains:

(a) a peptide of the present invention;
(b) a polynucleotide encoding the peptide of the present invention in an expressible form;
(c) an APC presenting a peptide of the present invention on its surface;
(d) an exosome presenting a peptide of the present invention on its surface; or
(e) a cytotoxic T cell of the present invention.

In the context of the present invention, a cancer over-expressing TOPK can be treated with these active ingredients. Examples of such cancer include, but are not limited to, AML, bladder cancer, breast cancer, cervical cancer, cholangiocellular carcinoma, colorectal cancer, diffuse-type gastric cancer, NSCLC, lymphoma, osteosarcoma, prostate cancer, renal carcinoma, SCLC and soft tissue tumor. Accordingly, prior to the administration of the vaccines or pharmaceutical compositions or agents including the aforementioned active ingredients, it is preferable to confirm whether the expression level of TOPK in the subject to be treated is enhanced. Thus, in one embodiment, the present invention provides a method for treating cancer (over) expressing TOPK in a patient in need thereof, such method including the steps of:

i) determining the expression level of TOPK in biological sample(s) obtained from a subject with the cancer to be treated;
ii) comparing the expression level of TOPK with normal control; and
iii) administrating at least one component selected from among (a) to (e) described above to a subject with cancer over-expressing TOPK as compared with normal control.

Alternatively, the present invention provides a vaccine or pharmaceutical composition including at least one component selected from among (a) to (e) described above, to be administered to a subject having cancer over-expressing TOPK. In other words, the present invention further provides a method for identifying a subject to be treated with the TOPK polypeptide of the present invention, such method including the step of determining an expression level of TOPK in subject-derived biological sample(s), wherein an increase of the level compared to a normal control level of the gene indicates that the subject may have cancer which may be treated with the TOPK polypeptide of the present invention. The methods of treating cancer of the present invention will be described in more detail in below.

Any subject-derived cell or tissue can be used for the determination of TOPK expression so long as it includes the objective transcription or translation product of TOPK. Examples of suitable samples include, but are not limited to, bodily tissues and fluids, such as blood, sputum and urine. Preferably, the subject-derived cell or tissue sample contains a cell population including an epithelial cell, more preferably a cancerous epithelial cell or an epithelial cell derived from tissue suspected to be cancerous. Further, if necessary, the cell may be purified from the obtained bodily tissues and fluids, and then used as the subjected-derived sample.

A subject to be treated by the present method is preferably a mammal. Illustrative mammals include, but are not limited to, e.g., human, non-human primate, mouse, rat, dog, cat, horse, and cow.

According to the present invention, the expression level of TOPK in biological sample obtained from a subject may be determined. The expression level can be determined at the transcription (nucleic acid) product level, using methods known in the art. For example, the mRNA of TOPK may be quantified using probes by hybridization methods (e.g., Northern hybridization). The detection may be carried out on a chip or an array. The use of an array is preferable for detecting the expression level of TOPK. Those skilled in the art can prepare such probes utilizing the sequence information of TOPK. For example, the cDNA of TOPK may be used as the probes. If necessary, the probes may be labeled with a suitable label, such as dyes, fluorescent substances and isotopes, and the expression level of the gene may be detected as the intensity of the hybridized labels.

Furthermore, the transcription product of TOPK may be quantified using primers by amplification-based detection methods (e.g., RT-PCR). Such primers may be prepared based on the available sequence information of the gene.

Specifically, a probe or primer used for the present method hybridizes under stringent, moderately stringent, or low stringent conditions to the mRNA of TOPK. As used herein, the phrase "stringent (hybridization) conditions" refers to conditions under which a probe or primer will hybridize to its target sequence, but not to other sequences. Stringent conditions are sequence-dependent and will be different under different circumstances. Specific hybridization of longer sequences is observed at higher temperatures than shorter sequences. Generally, the temperature of a stringent condition is selected to be about 5 degree Centigrade lower than the thermal melting point (Tm) for a specific sequence at a defined ionic strength and pH. The Tm is the temperature (under a defined ionic strength, pH and nucleic acid concentration) at which 50% of the probes complementary to their target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30 degree Centigrade for short probes or primers (e.g., 10 to 50 nucleotides) and at least about 60 degree Centigrade for longer probes or primers. Stringent conditions may also be achieved with the addition of destabilizing substances, such as formamide.

A probe or primer of the present invention is typically a substantially purified oligonucleotide. The oligonucleotide typically includes a region of nucleotide sequence that hybridizes under stringent conditions to at least about 2000, 1000, 500, 400, 350, 300, 250, 200, 150, 100, 50, or 25, consecutive sense strand nucleotide sequence of a nucleic acid including a TOPK sequence, or an anti sense strand nucleotide sequence of a nucleic acid including a TOPK sequence, or of a naturally occurring mutant of these sequences. In particular, for example, in a preferred embodiment, an oligonucleotide having 5-50 in length can be used as a primer for amplifying the genes, to be detected. More preferably, mRNA or cDNA of a TOPK gene can be detected with oligonucleotide probe or primer of a specific size, generally 15-30b in length. The size may range from at least 10 nucleotides, at least 12 nucleotides, at least 15 nucleotides, at least 20 nucleotides, at least 25 nucleotides, at least 30 nucleotides and the probes and primers may range in size from 5-10 nucleotides, 10-15 nucleotides, 15-20 nucleotides, 20-25 nucleotides and 25-30 nucleotides. In preferred embodiments, length of the oligonucleotide probe or primer can be selected from 15-25. Assay procedures, devices, or reagents for the detection of gene by using such oligonucleotide probe or primer are well known (e.g. oligonucleotide microarray or PCR). In these assays, probes or primers can also include tag or linker sequences. Further, probes or primers can be modified with detectable label or affinity ligand to be captured. Alternatively, in hybridization based detection procedures, a polynucleotide having a few hundreds (e.g., about 100-200) bases to a few kilo (e.g., about 1000-2000) bases in length can also be used for a probe (e.g., northern blotting assay or cDNA microarray analysis).

Alternatively, the translation product may be detected for the diagnosis of the present invention. For example, the quantity of TOPK protein (SEQ ID NO: 86) or the immunologically fragment thereof may be determined. Methods for determining the quantity of the protein as the translation product include immunoassay methods that use an antibody specifically recognizing the protein. The antibody may be monoclonal or polyclonal. Furthermore, any fragment or modification (e.g., chimeric antibody, scFv, Fab, F(ab')$_2$, Fv, etc.) of the antibody may be used for the detection, so long as the fragment or modified antibody retains the binding ability to the TOPK protein. Such antibodies against the peptides of the present invention and the fragments thereof are also provided by the present invention. Methods to prepare these kinds of antibodies for the detection of proteins are well known in the art, and any method may be employed in the present invention to prepare such antibodies and equivalents thereof.

As another method to detect the expression level of TOPK gene based on its translation product, the intensity of staining may be measured via immunohistochemical analysis using an antibody against the TOPK protein. Namely, in this measurement, strong staining indicates increased presence/ level of the protein and, at the same time, high expression level of TOPK gene.

The expression level of a target gene, e.g., the TOPK gene, in cancer cells can be determined to be increased if the level increases from the control level (e.g., the level in normal cells) of the target gene by, for example, 10%, 25%, or 50%; or increases to more than 1.1 fold, more than 1.5 fold, more than 2.0 fold, more than 5.0 fold, more than 10.0 fold, or more.

The control level may be determined at the same time as the cancer cells by using a sample(s) previously collected and stored from a subject/subjects whose disease state(s) (cancerous or non-cancerous) is/are known. In addition, normal cells obtained from non-cancerous regions of an organ that has the cancer to be treated may be used as normal control. Alternatively, the control level may be determined by a statistical method based on the results obtained by analyzing previously determined expression level(s) of TOPK gene in samples from subjects whose disease states are known. Furthermore, the control level can be derived from a database of expression patterns from previously tested cells. Moreover, according to an aspect of the present invention, the expression level of TOPK gene in a biological sample may be compared to multiple control levels, which are determined from multiple reference samples. It is preferred to use a control level determined from a reference sample derived from a tissue type similar to that of the subject-derived biological sample. Moreover, it is preferred to use the standard value of the expression levels of TOPK gene in a population with a known disease state. The standard value may be obtained by any method known in the art. For example, a range of mean+/−2 S.D. or mean+/−3 S.D. may be used as the standard value.

In the context of the present invention, a control level determined from a biological sample that is known to be non-cancerous is referred to as a "normal control level". On the other hand, if the control level is determined from a cancerous biological sample, it is referred to as a "cancerous control level". Difference between a sample expression level and a control level can be normalized to the expression level of control nucleic acids, e.g., housekeeping genes, whose expression levels are known not to differ depending on the cancerous or non-cancerous state of the cell. Exemplary control genes include, but are not limited to, beta-actin, glyceraldehyde 3 phosphate dehydrogenase, and ribosomal protein P1.

When the expression level of TOPK gene is increased as compared to the normal control level, or is similar/equivalent to the cancerous control level, the subject may be diagnosed with cancer to be treated.

The present invention also provides a method of (i) diagnosing whether a subject suspected to have cancer to be treated, and/or (ii) selecting a subject for cancer treatment, such method including the steps of:

a) determining the expression level of TOPK in biological sample(s) obtained from a subject who is suspected to have the cancer to be treated;

b) comparing the expression level of TOPK with a normal control level;

c) diagnosing the subject as having the cancer to be treated, if the expression level of TOPK is increased as compared to the normal control level; and d) selecting the subject for cancer treatment, if the subject is diagnosed as having the cancer to be treated, in step c).

Alternatively, such a method may include the steps of:

a) determining the expression level of TOPK in biological sample(s) obtained from a subject who is suspected to have the cancer to be treated;

b) comparing the expression level of TOPK with a cancerous control level;

c) diagnosing the subject as having the cancer to be treated, if the expression level of TOPK is similar or equivalent to the cancerous control level; and d) selecting the subject for cancer treatment, if the subject is diagnosed as having the cancer to be treated, in step c).

The present invention also provides a diagnostic kit for diagnosing or determining a subject who is or is suspected to be suffering from or at risk of developing a cancer that can be treated with the TOPK polypeptide of the present invention, which may also be useful in either or both of assessing and monitoring the efficacy, or applicability of a cancer immunotherapy. Preferably, the cancer includes, but is not limited to, AML, bladder cancer, breast cancer, cervical cancer, cholangiocellular carcinoma, colorectal cancer, diffuse-type gastric cancer, NSCLC, lymphoma, osteosarcoma, prostate cancer, renal carcinoma, SCLC and soft tissue tumor. More particularly, the kit preferably includes at least one reagent for detecting the expression of the TOPK gene in a subject-derived cell, which reagent may be selected from the group of:

(a) a reagent for detecting an mRNA of the TOPK gene;

(b) a reagent for detecting the TOPK protein or the immunologically fragment thereof; and (c) a reagent for detecting the biological activity of the TOPK protein.

Examples of reagents suitable for detecting an mRNA of the TOPK gene include nucleic acids that specifically bind to or identify the TOPK mRNA, such as oligonucleotides that have a complementary sequence to a portion of the TOPK mRNA. These kinds of oligonucleotides are exemplified by primers and probes that are specific to the TOPK mRNA. These kinds of oligonucleotides may be prepared based on methods well known in the art. If needed, the reagent for detecting the TOPK mRNA may be immobilized on a solid matrix. Moreover, more than one reagent for detecting the TOPK mRNA may be included in the kit.

On the other hand, examples reagents suitable for detecting the TOPK protein or the immunologically fragment thereof may include antibodies to the TOPK protein or the immunologically fragment thereof. The antibody may be monoclonal or polyclonal. Furthermore, any fragment or modification (e.g., chimeric antibody, scFv, Fab, F(ab')$_2$, Fv, etc.) of the antibody may be used as the reagent, so long as the fragment or modified antibody retains the binding ability to the TOPK protein or the immunologically fragment thereof. Methods to prepare these kinds of antibodies for the detection of proteins are well known in the art, and any method may be employed in the present invention to prepare such antibodies and equivalents thereof. Furthermore, the antibody may be labeled with signal generating molecules via direct linkage or an indirect labeling technique. Labels and methods for labeling antibodies and detecting the binding of the antibodies to their targets are well known in the art, and any labels and methods may be employed for the present invention. Moreover, more than one reagent for detecting the TOPK protein may be included in the kit.

The kit may contain more than one of the aforementioned reagents. The kit can further include a solid matrix and reagent for binding a probe against a TOPK gene or antibody against a TOPK peptide, a medium and container for culturing cells, positive and negative control reagents, and a secondary antibody for detecting an antibody against a TOPK peptide. For example, tissue samples obtained from subjects without cancer or suffering from cancer, may serve as useful control reagents. A kit of the present invention may further include other materials desirable from a commercial and user standpoint, including buffers, diluents, filters, needles, syringes, and package inserts (e.g., written, tape, CD-ROM, etc.) with instructions for use. These reagents and such may be retained in a container with a label. Suitable containers include bottles, vials, and test tubes. The containers may be formed from a variety of materials, such as glass or plastic.

In an embodiment of the present invention, when the reagent is a probe against the TOPK mRNA, the reagent may be immobilized on a solid matrix, such as a porous strip, to form at least one detection site. The measurement or detection region of the porous strip may include a plurality of sites, each containing a nucleic acid (probe). A test strip may also contain sites for negative and/or positive controls. Alternatively, control sites may be located on a strip separated from the test strip. Optionally, the different detection sites may contain different amounts of immobilized nucleic acids, i.e., a higher amount in the first detection site and lesser amounts in subsequent sites. Upon the addition of a test sample, the number of sites displaying a detectable signal provides a quantitative indication of the amount of TOPK mRNA present in the sample. The detection sites may be configured in any suitably detectable shape and are typically in the shape of a bar or dot spanning the width of a test strip.

The kit of the present invention may further include a positive control sample or TOPK standard sample. The positive control sample of the present invention may be prepared by collecting TOPK positive samples and then assaying their TOPK levels. Alternatively, a purified TOPK protein or polynucleotide may be added to cells that do not express TOPK to form the positive sample or the TOPK standard sample. In the present invention, purified TOPK may be a recombinant protein. The TOPK level of the positive control sample is, for example, more than the cut off value.

In one embodiment, the present invention further provides a diagnostic kit including, a protein or a partial protein thereof specifically recognized by the antibody of the present invention or the fragment thereof.

Examples of the partial peptide of the protein of the present invention include polypeptides composed of at least 8, preferably 15, and more preferably 20 contiguous amino acids in the amino acid sequence of the protein of the present invention. Cancer can be diagnosed by detecting an antibody in a sample (e.g., blood, tissue) using a protein or a peptide (polypeptide) of the present invention. The method for preparing the protein of the present invention and peptides are as described above.

The methods for diagnosing cancer of the present invention can be performed by determining the difference between the amount of anti-TOPK antibody and that in the corresponding control sample as describe above. The subject is suspected to be suffering from cancer, if cells or tissues of the subject contain antibodies against the expression products (TOPK) of the gene and the quantity of the anti-TOPK antibody is determined to be more than the cut off value in level compared to that in normal control.

In another embodiment, a diagnostic kit of the present invention may include the peptide of the present invention and an HLA molecule binding thereto. The method for detecting antigen specific CTLs using antigenic peptides and HLA molecules has already been established (for example, Altman J D et al., Science. 1996, 274(5284): 94-6). Thus, the complex of the peptide of the present invention and the HLA molecule can be applied to the detection method to detect tumor antigen specific CTLs, thereby enabling earlier detection, recurrence and/or metastasis of cancer. Further, it can be employed for the selection of subjects applicable with the pharmaceuticals including the peptide of the present invention as an active ingredient, or the assessment of the treatment effect of the pharmaceuticals.

Particularly, according to the known method (see, for example, Altman J D et al., Science. 1996, 274(5284): 94-6), the oligomer complex, such as tetramer, of the radiolabeled HLA molecule and the peptide of the present invention can be prepared. With using the complex, the diagnosis can be done, for example, by quantifying the antigen-peptide specific CTLs in the peripheral blood lymphocytes derived from the subject suspected to be suffering from cancer.

The present invention further provides method and diagnostic agents for evaluating immunological response of subject by using peptide epitopes as described herein. In one embodiment of the invention, HLA-A24 or HLA-A2 restricted peptides as described herein are used as reagents for evaluating or predicting an immune response of a subject. The immune response to be evaluated is induced by contacting an immunogen with immunocompetent cells in vitro or in vivo. In preferred embodiments, the immunocompetent cells for evaluating an immunological response, may be selected from among peripheral blood, peripheral blood lymphocyte (PBL), and peripheral blood mononuclear cell (PBMC). Methods for collecting or isolating such immunocompetent cells are well known in the arts. In some embodiments, any agent that may result in the production of antigen specific CTLs that recognize and bind to the peptide epitope(s) may be employed as the reagent. The peptide reagent need not be used as the immunogen. Assay systems that are used for such an analysis include relatively recent technical developments such as tetramers, staining for intracellular lymphokines and interferon release assays, or ELISPOT assays. In a preferred embodiment, immunocompetent cells to be contacted with peptide reagent may be antigen presenting cells including dendritic cells.

For example, peptides of the present invention may be used in tetramer staining assays to assess peripheral blood mononuclear cells for the presence of antigen-specific CTLs following exposure to a tumor cell antigen or an immunogen. The HLA tetrameric complex may be used to directly visualize antigen specific CTLs (see, e.g., Ogg et al., Science 279: 2103-2106, 1998; and Altman et al, Science 174: 94-96, 1996) and determine the frequency of the antigen-specific CTL population in a sample of peripheral blood mononuclear cells. A tetramer reagent using a peptide of the invention may be generated as described below.

A peptide that binds to an HLA molecule is refolded in the presence of the corresponding HLA heavy chain and beta 2-microglobulin to generate a trimolecular complex. In the complex, carboxyl terminal of the heavy chain is biotinylated at a site that was previously engineered into the protein. Then, streptavidin is added to the complex to form tetramer composed of the trimolecular complex and streptavidin. By means of fluorescently labeled streptavidin, the tetramer can be used to stain antigen-specific cells. The cells can then be identified, for example, by flow cytometry. Such an analysis may be used for diagnostic or prognostic purposes. Cells identified by the procedure can also be used for therapeutic purposes.

The present invention also provides reagents to evaluate immune recall responses (see, e.g., Bertoni et aL, J. Clin. Invest. 100: 503-513, 1997 and Penna et aL, J. Exp. Med. 174: 1565-1570, 1991) including peptides of the present invention. For example, patient PBMC samples obtained from individuals with a cancer to be treated are analyzed for the presence of antigen-specific CTLs using specific peptides. A blood sample containing mononuclear cells can be evaluated by cultivating the PBMCs and stimulating the cells with a peptide of the invention. After an appropriate cultivation period, the expanded cell population can be analyzed, for example, for CTL activity.

The peptides may be also used as reagents to evaluate the efficacy of a vaccine. PBMCs obtained from a patient vaccinated with an immunogen may be analyzed using, for example, either of the methods described above. The patient is HLA typed, and peptide epitope reagents that recognize the allele specific molecules present in that patient are selected for the analysis. The immunogenicity of the vaccine may be indicated by the presence of epitope-specific CTLs in the PBMC sample.

The peptides of the invention may be also used to make antibodies, using techniques well known in the art (see, e.g. CURRENT PROTOCOLS INIMMUNOLOGY, Wiley/

Greene, N Y; and Antibodies A Laboratory Manual, Harlow and Lane, Cold Spring Harbor Laboratory Press, 1989), which may be useful as reagents to diagnose or monitor cancer. Such antibodies may include those that recognize a peptide in the context of an HLA molecule, i.e., antibodies that bind to a peptide-MHC complex.

The peptides and compositions of the present invention have a number of additional uses, some of which are described herein. For instance, the present invention provides a method for diagnosing or detecting a disorder characterized by expression of a TOPK immunogenic polypeptide. These methods involve determining expression of a TOPK HLA binding peptide, or a complex of a TOPK HLA binding peptide and an HLA class I molecule in a biological sample. The expression of a peptide or complex of peptide and HLA class I molecule can be determined or detected by assaying with a binding partner for the peptide or complex. In a preferred embodiment, a binding partner for the peptide or complex is an antibody recognizes and specifically bind to the peptide. The expression of TOPK in a biological sample, such as a tumor biopsy, can also be tested by standard PCR amplification protocols using TOPK primers. An example of tumor expression is presented herein and further disclosure of exemplary conditions and primers for TOPK amplification can be found in WO2003/27322.

Preferably, the diagnostic methods involve contacting a biological sample isolated from a subject with an agent specific for the TOPK HLA binding peptide to detect the presence of the TOPK HLA binding peptide in the biological sample. As used herein, "contacting" means placing the biological sample in sufficient proximity to the agent and under the appropriate conditions of, e.g., concentration, temperature, time, ionic strength, to allow the specific interaction between the agent and TOPK HLA binding peptide that are present in the biological sample. In general, the conditions for contacting the agent with the biological sample are conditions known by those of ordinary skill in the art to facilitate a specific interaction between a molecule and its cognate (e.g., a protein and its receptor cognate, an antibody and its protein antigen cognate, a nucleic acid and its complementary sequence cognate) in a biological sample. Optimal conditions for facilitating a specific interaction between a molecule and its cognate are described in U.S. Pat. No. 5,108,921, issued to Low et al.

The diagnostic method of the present invention can be performed in either or both of in vivo and in vitro. Accordingly, biological sample can be located in vivo or in vitro in the present invention. For example, the biological sample can be a tissue in vivo and the agent specific for the TOPK immunogenic polypeptide can be used to detect the presence of such molecules in the tissue. Alternatively, the biological sample can be collected or isolated in vitro (e.g., a blood sample, tumor biopsy, tissue extract). In a particularly preferred embodiment, the biological sample can be a cell-containing sample, more preferably a sample containing tumor cells collected from a subject to be diagnosed or treated.

Alternatively, the diagnosis can be done, by a method which allows direct quantification of antigen-specific T cells by staining with Fluorescein-labelled HLA multimeric complexes (for example, Altman, J. D. et al., 1996, Science 274: 94; Altman, J. D. et al., 1993, Proc. Natl. Acad. Sci. USA 90: 10330). Staining for intracellular lymphokines, and interferon-gamma release assays or ELISPOT assays also has been provided. Tetramer staining, intracellular lymphokine staining and ELISPOT assays all appear to be at least 10-fold more sensitive than more conventional assays (Murali-Krishna, K. et al., 1998, Immunity 8: 177; Lalvani, A. et al., 1997, J. Exp. Med. 186: 859; Dunbar, P. R. et al., 1998, Curr. Biol. 8: 413). Pentamers (e.g., US 2004-209295A), dextramers (e.g., WO 02/072631), and streptamers (e.g., Nature medicine 6. 631-637 (2002)) may also be used.

For instance, in some embodiments, the present invention provides a method for diagnosing or evaluating an immunological response of a subject administered at least one of TOPK peptides of the present invention, the method including the steps of:

(a) contacting an immunogen with immunocompetent cells under the condition suitable for induction of CTL specific to the immunogen;

(b) detecting or determining induction level of the CTL induced in step (a); and (c) correlating the immunological response of the subject with the CTL induction level.

In the context of the present invention, the immunogen preferably includes at least one of (a) a TOPK peptide selected from among the amino acid sequences of SEQ ID NOs: 2 to 40 and 42 to 84, peptides having such amino acid sequences, and peptides having in which such amino acid sequences have been modified with 1, 2 or more amino acid substitution(s). In the meantime, conditions suitable of induction of immunogen specific CTL are well known in the art. For example, immunocompetent cells may be cultured in vitro under the presence of immunogen(s) to induce immunogen specific CTL. In order to induce immunogen specific CTLs, any stimulating factors may be added to the cell culture. For example, IL-2 is preferable stimulating factors for the CTL induction.

In some embodiments, the step of monitoring or evaluating immunological response of a subject to be treated with peptide cancer therapy may be performed before, during and/or after the treatment. In general, during a protocol of cancer therapy, immunogenic peptides are administered repeatedly to a subject to be treated. For example, immunogenic peptides may be administered every week for 3-10 weeks. Accordingly, the immunological response of the subject can be evaluated or monitored during the cancer therapy protocol. Alternatively, the step of evaluation or monitoring of immunological response to the cancer therapy may at the completion of the therapy protocol.

According to the present invention, enhanced induction of immunogen specific CTL as compared with a control indicates that the subject to be evaluated or diagnosed immunologically responded to the immunogen(s) that has/have been administered. Suitable controls for evaluating the immunological response may include, for example, a CTL induction level when the immunocompetent cells are contacted with no peptide, or control peptide(s) having amino acid sequences other than any TOPK peptides. (e.g. random amino acid sequence). In a preferred embodiment, the immunological response of the subject is evaluated in a sequence specific manner, by comparison with an immunological response between each immunogen administered to the subject. In particular, even when a mixture of some kinds of TOPK peptides is administered to the subject, immunological response might vary depending on the peptides. In that case, by comparison of the immunological response between each peptide, peptides to which the subject show higher response can be identified.

XII. ANTIBODIES

The present invention further provides antibodies that bind to peptides of the present invention. Preferred antibodies specifically bind to peptides of the present invention and will not bind (or will bind weakly) to other peptides. Alternatively, antibodies may bind to peptides of the invention as well as the homologs thereof. Antibodies against peptides of the invention can find use in cancer diagnostic and prognostic assays, as well as imaging methodologies. Similarly, such antibodies can find use in the treatment, diagnosis, and/or prognosis of other cancers, to the extent TOPK is also expressed or over-expressed in a cancer patient. Moreover, intracellularly expressed antibodies (e.g., single chain antibodies) may therapeutically find use in treating cancers in which the expression of TOPK is involved, example of which include, but are not limited to, AML, bladder cancer, breast cancer, cervical cancer, cholangiocellular carcinoma, colorectal cancer, diffuse-type gastric cancer, NSCLC, lymphoma, osteosarcoma, prostate cancer, renal carcinoma, SCLC and soft tissue tumor.

The present invention also provides various immunological assays for the detection and/or quantification of the TOPK protein (SEQ ID NO: 86) or fragments thereof, including polypeptides having amino acid sequences selected from the group consisting of SEQ ID NOs: 2 to 40 and 42 to 84. Such assays may include one or more anti-TOPK antibodies capable of recognizing and binding a TOPK protein or fragments thereof, as appropriate. In the context of the present invention, anti-TOPK antibodies binding to TOPK polypeptide preferably recognize polypeptide having amino acid sequences selected from the group consisting of SEQ ID NOs: 2 to 40 and 42 to 84, preferably to the exclusion of other peptides. The binding specificity of antibody can be confirmed by means of an inhibition test. That is, when the binding between an antibody to be analyzed and full-length of TOPK polypeptide is inhibited under presence of any fragment polypeptide having an amino acid sequence of SEQ ID NOs: 2 to 40 and 42 to 84, it is deemed to specifically bind the fragment. In the context of the present invention, such immunological assays are performed within various immunological assay formats well known in the art, including but not limited to, various types of radioimmunoassays, immuno-chromatograph technique, enzyme-linked immunosorbent assays (ELISA), enzyme-linked immunofluorescent assays (ELIFA), and the like.

Related immunological but non-antibody assays of the invention may also include T cell immunogenicity assays (inhibitory or stimulatory) as well as MHC binding assays. In addition, the present invention contemplates immunological imaging methods capable of detecting cancers expressing TOPK, example of which include, but are not limited to, radioscintigraphic imaging methods using labeled antibodies of the present invention. Such assays find clinical use in the detection, monitoring, and prognosis of TOPK expressing cancers, examples of which include, but are not limited to, AML, bladder cancer, breast cancer, cervical cancer, cholangiocellular carcinoma, colorectal cancer, diffuse-type gastric cancer, NSCLC, lymphoma, osteosarcoma, prostate cancer, renal carcinoma, SCLC and soft tissue tumor.

The present invention also provides antibodies that bind to the peptides of the invention. An antibody of the invention can be used in any form, for example as a monoclonal or polyclonal antibody, and may further include antiserum obtained by immunizing an animal such as a rabbit with the peptide of the invention, all classes of polyclonal and monoclonal antibodies, human antibodies and humanized antibodies produced by genetic recombination.

A peptide of the invention used as an antigen to obtain an antibody may be derived from any animal species, but is preferably derived from a mammal such as a human, mouse, or rat, more preferably from a human. A human-derived peptide may be obtained from the nucleotide or amino acid sequences disclosed herein.

According to the present invention, complete and partial peptides of a protein may serve as immunization antigens. Examples of suitable partial peptides include, for example, the amino (N)-terminal or carboxy (C)-terminal fragment of a peptide of the present invention.

Herein, an antibody is defined as a protein that reacts with either the full length or a fragment of a TOPK peptide. In a preferred embodiment, an antibody of the present invention can recognize fragment peptides of TOPK having an amino acid sequence selected from the group consisting of SEQ ID NOs: 2 to 40 and 42 to 84. Methods for synthesizing oligopeptide are well known in the arts. After the synthesis, peptides may be optionally purified prior to use as immunogen. In the context of the present invention, the oligopeptide (e.g., 9- or 10mer) may be conjugated or linked with carriers to enhance the immunogenicity. Keyhole-limpet hemocyanin (KLH) is well known as the carrier. Method for conjugating KLH and peptide are also well known in the arts.

Alternatively, a gene encoding a peptide of the invention or fragment thereof may be inserted into a known expression vector, which is then used to transform a host cell as described herein. The desired peptide or fragment thereof may be recovered from the outside or inside of host cells by any standard method, and may subsequently be used as an antigen. Alternatively, whole cells expressing the peptide or their lysates or a chemically synthesized peptide may be used as the antigen.

Any mammalian animal may be immunized with the antigen, though preferably the compatibility with parental cells used for cell fusion is taken into account. In general, animals of Rodentia, Lagomorpha or Primates may be used. Animals of the family Rodentia include, for example, mouse, rat and hamster. Animals of the family Lagomorpha include, for example, rabbit. Animals of the Primate family include, for example, a monkey of Catarrhini (old world monkey) such as *Macaca fascicularis*, rhesus monkey, sacred baboon and chimpanzees.

Methods for immunizing animals with antigens are known in the art. Intraperitoneal injection or subcutaneous injection of antigens is a standard method for the immunization of mammals. More specifically, antigens may be diluted and suspended in an appropriate amount of phosphate buffered saline (PBS), physiological saline, etc. If desired, the antigen suspension may be mixed with an appropriate amount of a standard adjuvant, such as Freund's complete adjuvant, made into emulsion and then administered to mammalian animals. Preferably, it is followed by several administrations of antigen mixed with an appropriately amount of Freund's incomplete adjuvant every 4 to 21 days. An appropriate carrier may also be used for immunization. After immunization as above, serum may be examined by a standard method for an increase in the amount of desired antibodies.

Polyclonal antibodies against the peptides of the present invention may be prepared by collecting blood from the immunized mammal examined for the increase of desired antibodies in the serum, and by separating serum from the blood by any conventional method. Polyclonal antibodies may include serum containing the polyclonal antibodies, as well as the fraction containing the polyclonal antibodies may be isolated from the serum. Immunoglobulin G or M can be prepared from a fraction which recognizes only the peptide of the present invention using, for example, an affinity column coupled with the peptide of the present invention, and further purifying this fraction using protein A or protein G column.

To prepare monoclonal antibodies for use in the context of the present invention, immune cells are collected from the mammal immunized with the antigen and checked for the increased level of desired antibodies in the serum as described above, and are subjected to cell fusion. The immune cells used for cell fusion may preferably be obtained from spleen. Other preferred parental cells to be fused with the above immunocyte include, for example, myeloma cells of mammalians, and more preferably myeloma cells having an acquired property for the selection of fused cells by drugs.

The above immunocyte and myeloma cells can be fused according to known methods, for example, the method of Milstein et al. (Galfre and Milstein, Methods Enzymol 73: 3-46 (1981)).

Resulting hybridomas obtained by cell fusion may be selected by cultivating them in a standard selection medium, such as HAT medium (hypoxanthine, aminopterin and thymidine containing medium). The cell culture is typically continued in the HAT medium for several days to several weeks, the time being sufficient to allow all the other cells, with the exception of the desired hybridoma (non-fused cells), to die. Then, the standard limiting dilution may be performed to screen and clone a hybridoma cell producing the desired antibody.

In addition to the above method, wherein a non-human animal is immunized with an antigen for preparing hybridoma, human lymphocytes such as those infected by EB virus may be immunized with a peptide, peptide expressing cells or their lysates in vitro. Then, the immunized lymphocytes may be fused with human-derived myeloma cells that are capable of indefinitely dividing, such as U266, to yield a hybridoma producing a desired human antibody that is able to bind to the peptide can be obtained (Unexamined Published Japanese Patent Application No. Sho 63-17688).

The obtained hybridomas may then be subsequently transplanted into the abdominal cavity of a mouse and the ascites extracted. The obtained monoclonal antibodies can be purified by, for example, ammonium sulfate precipitation, a protein A or protein G column, DEAE ion exchange chromatography or an affinity column to which the peptide of the present invention is coupled. An antibody of the present invention can be used not only for purification and detection of a peptide of the present invention, but also as a candidate for agonists and antagonists of a peptide of the present invention. Alternatively, an immune cell, such as an immunized lymphocyte, producing antibodies may be immortalized by an oncogene and used for preparing monoclonal antibodies.

Monoclonal antibodies thus obtained can be also recombinantly prepared using genetic engineering techniques (see, for example, Borrebaeck and Larrick, Therapeutic Monoclonal Antibodies, published in the United Kingdom by MacMillan Publishers LTD (1990)). For example, a DNA encoding an antibody may be cloned from an immune cell, such as a hybridoma or an immunized lymphocyte producing the antibody, inserted into an appropriate vector, and introduced into host cells to prepare a recombinant antibody. The present invention also provides for recombinant antibodies prepared as described above.

An antibody of the present invention may be a fragment of an antibody or modified antibody, so long as it binds to one or more of the peptides of the invention. For instance, the antibody fragment may be Fab, F(ab')$_2$, Fv or single chain Fv (scFv), in which Fv fragments from H and L chains are ligated by an appropriate linker (Huston et al., Proc Natl Acad Sci USA 85: 5879-83 (1988)). More specifically, an antibody fragment may be generated by treating an antibody with an enzyme, such as papain or pepsin. Alternatively, a gene encoding the antibody fragment may be constructed, inserted into an expression vector and expressed in an appropriate host cell (see, for example, Co et al., J Immunol 152: 2968-76 (1994); Better and Horwitz, Methods Enzymol 178: 476-96 (1989); Pluckthun and Skerra, Methods Enzymol 178: 497-515 (1989); Lamoyi, Methods Enzymol 121: 652-63 (1986); Rousseaux et al., Methods Enzymol 121: 663-9 (1986); Bird and Walker, Trends Biotechnol 9: 132-7 (1991)).

An antibody may be modified by conjugation with a variety of molecules, such as polyethylene glycol (PEG). The present invention provides for such modified antibodies. The modified antibody can be obtained by chemically modifying an antibody. These modification methods are conventional in the field.

Alternatively, an antibody of the present invention may be obtained as a chimeric antibody, between a variable region derived from nonhuman antibody and the constant region derived from human antibody, or as a humanized antibody, including the complementarity determining region (CDR) derived from nonhuman antibody, the frame work region (FR) and the constant region derived from human antibody. Such antibodies can be prepared according to known technology. Humanization can be performed by substituting rodent CDRs or CDR sequences for the corresponding sequences of a human antibody (see, e.g., Verhoeyen et al., Science 239:1534-1536 (1988)). Accordingly, such humanized antibodies are chimeric antibodies, wherein substantially less than an intact human variable domain has been substituted by the corresponding sequence from a non-human species.

Fully human antibodies including human variable regions in addition to human framework and constant regions can also be used. Such antibodies can be produced using various techniques known in the art. For example, in vitro methods involve use of recombinant libraries of human antibody fragments displayed on bacteriophage (e.g., Hoogenboom & Winter, J. Mol. Biol. 227:381 (1991). Similarly, human antibodies can be made by introducing of human immunoglobulin loci into transgenic animals, e.g., mice in which the endogenous immunoglobulin genes have been partially or completely inactivated. This approach is described, e.g., in U.S. Pat. Nos. 6,150,584, 5,545,807; 5,545,806; 5,569,825; 5,625,126; 5,633,425; 5,661,016.

Antibodies obtained as above may be purified to homogeneity. For example, the separation and purification of the antibody can be performed according to the separation and purification methods used for general proteins. For example, the antibody may be separated and isolated by the appropriately selected and combined use of column chromatographies, such as affinity chromatography, filter, ultrafiltration, salting-out, dialysis, SDS polyacrylamide gel electrophoresis and isoelectric focusing (Antibodies: A Laboratory Manual. Ed Harlow and David Lane, Cold Spring Harbor Laboratory (1988)), but are not limited thereto. A protein A column and protein G column can be used as the affinity column. Exemplary protein A columns to be used include, for example, Hyper D, POROS and Sepharose F.F. (Pharmacia).

Examples of suitable chromatography techniques, with the exception of affinity chromatography include, for example, ion-exchange chromatography, hydrophobic chromatography, gel filtration, reverse phase chromatography, adsorption chromatography and the like (Strategies for Protein Purification and Characterization: A Laboratory Course Manual. Ed Daniel R. Marshak et al., Cold Spring Harbor Laboratory Press (1996)). The chromatographic procedures can be carried out by liquid-phase chromatography, such as HPLC and FPLC.

For example, measurement of absorbance, enzyme-linked immunosorbent assay (ELISA), enzyme immunoassay (EIA), radioimmunoassay (RIA) and/or immunofluorescence may be used to measure the antigen binding activity of the antibody of the invention. In ELISA, the antibody of the present invention is immobilized on a plate, a peptide of the invention is applied to the plate, and then a sample containing a desired antibody, such as culture supernatant of antibody producing cells or purified antibodies, is applied. Then, a secondary antibody that recognizes the primary antibody and is labeled with an enzyme, such as alkaline phosphatase, is applied, and the plate is incubated. Next, after washing, an enzyme substrate, such as p-nitrophenyl phosphate, is added to the plate, and the absorbance is measured to evaluate the antigen binding activity of the sample. A fragment of the peptide, such as a C-terminal or N-terminal fragment, may be used as the antigen to evaluate the binding activity of the antibody. BIAcore (Pharmacia) may be used to evaluate the activity of the antibody according to the present invention.

The above methods allow for the detection or measurement of a peptide of the invention, by exposing an antibody of the invention to a sample presumed to contain a peptide of the invention, and detecting or measuring the immune complex formed by the antibody and the peptide.

Because the method of detection or measurement of the peptide according to the invention can specifically detect or measure a peptide, the method can find use in a variety of experiments in which the peptide is used.

XIII. VECTORS AND HOST CELLS

The present invention also provides for vectors and host cells into which a nucleotide encoding a peptide of the present invention is introduced. A vector of the present invention finds utility as a carrier of nucleotides, especially a DNA, of the present invention in host cell, to express a peptide of the present invention, or to administer a nucleotide of the present invention for gene therapy.

When E. coli is selected as the host cell and the vector is amplified and produced in a large amount in E. coli (e.g., JM109, DH5 alpha, HB101 or XL1Blue), the vector should have an "ori" to suitable for amplification in E. coli and a marker gene suited for selecting transformed E. coli (e.g., a drug-resistance gene selected by a drug such as ampicillin, tetracycline, kanamycin, chloramphenicol or the like). For example, M13-series vectors, pUC-series vectors, pBR322, pBluescript, pCR-Script, etc., can be used. In addition, pGEM-T, pDIRECT and pT7 can also be used for subcloning and extracting cDNA as well as the vectors described above. When a vector is used to produce the protein of the present invention, an expression vector can find use. For example, an expression vector to be expressed in E. coli should have the above characteristics to be amplified in E. coli. When E. coli, such as JM109, DH5 alpha, HB101 or XL1 Blue, are used as a host cell, the vector should have a promoter, for example, lacZ promoter (Ward et al., Nature 341: 544-6 (1989); FASEB J 6: 2422-7 (1992)), araB promoter (Better et al., Science 240: 1041-3 (1988)), T7 promoter or the like, that can efficiently express the desired gene in E. coli. In that respect, pGEX-5X-1 (Pharmacia), "QIAexpress system" (Qiagen), pEGFP and pET (in this case, the host is preferably BL21 which expresses T7 RNA polymerase), for example, can be used instead of the above vectors. Additionally, the vector may also contain a signal sequence for peptide secretion. An exemplary signal sequence that directs the peptide to be secreted to the periplasm of the E. coli is the pelB signal sequence (Lei et al., J Bacteriol 169: 4379 (1987)). Means for introducing of the vectors into the target host cells include, for example, the calcium chloride method, and the electroporation method.

In addition to E. coli, for example, expression vectors derived from mammals (for example, pcDNA3 (Invitrogen) and pEGF-BOS (Nucleic Acids Res 18(17): 5322 (1990)), pEF, pCDM8), expression vectors derived from insect cells (for example, "Bac-to-BAC baculovirus expression system" (GIBCO BRL), pBacPAK8), expression vectors derived from plants (e.g., pMH1, pMH2), expression vectors derived from animal viruses (e.g., pHSV, pMV, pAdexLcw), expression vectors derived from retroviruses (e.g., pZIpneo), expression vector derived from yeast (e.g., "Pichia Expression Kit" (Invitrogen), pNV11, SP-Q01) and expression vectors derived from Bacillus subtilis (e.g., pPL608, pKTH50) can be used for producing the polypeptide of the present invention.

In order to express the vector in animal cells, such as CHO, COS or NIH3T3 cells, the vector should have a promoter necessary for expression in such cells, for example, the SV40 promoter (Mulligan et al., Nature 277: 108 (1979)), the MMLV-LTR promoter, the EF1 alpha promoter (Mizushima et al., Nucleic Acids Res 18: 5322 (1990)), the CMV promoter and the like, and preferably a marker gene for selecting transformants (for example, a drug resistance gene selected by a drug (e.g., neomycin, G418)). Examples of known vectors with these characteristics include, for example, pMAM, pDR2, pBK-RSV, pBK-CMV, pOPRSV and pOP13.

Hereinafter, the present invention is described in more detail with reference to the Examples. However, while the following materials, methods and examples may serve to assist one of ordinary skill in making and using certain embodiments of the present invention, there are only intended to illustrate aspects of the present invention and thus in no way to limit the scope of the present invention. As one of ordinary skill in the art will readily recognize, methods and materials similar or equivalent to those described herein can be used in the practice or testing of the present invention.

EXAMPLES

Materials and Methods

Cell Lines

TISI, HLA-A*2402-positive B-lymphoblastoid cell line, was purchased from IHWG Cell and Gene Bank (Seattle, Wash.). T2, HLA-A*0201-positive B-lymphoblastoid cell line, and COS7, African green monkey kidney cell line, were purchased from ATCC.

Candidate Selection of Peptides Derived from TOPK 9-mer and 10-mer peptides derived from TOPK (GenBank Accession No. NM_018492; for example, SEQ ID No: 85) that bind to either or both of HLA-A*2402 and HLA-A*0201 molecule were predicted using "NetMHC3.0" binding prediction server (http://www.cbs.dtu.dk/services/NetMHC/) (Buus et al., Tissue Antigens. 2003 November, 62(5):378-84; Nielsen et al., Protein Sci. 2003 May, 12(5): 1007-17, Bioinformatics. 2004 Jun. 12:20(9):1388-97). These peptides were synthesized by Biosynthesis (Lewisville, Tex.) according to a standard solid phase synthesis method and purified by reversed phase high performance liquid chromatography (HPLC). The purity (>90%) and the identity of the peptides were determined by analytical HPLC and mass spectrometry analysis, respectively. Peptides were dissolved in dimethyl-sulfoxide at 20 mg/ml and stored at −80 degrees C.

In Vitro CTL Induction

Monocyte-derived dendritic cells (DCs) were used as antigen-presenting cells to induce cytotoxic T lymphocyte (CTL) responses against peptides presented on human leukocyte antigen (HLA). DCs were generated in vitro as described elsewhere (Nakahara S et al., Cancer Res 2003 Jul. 15, 63(14): 4112-8). Specifically, peripheral blood mononuclear cells isolated from a normal volunteer (HLA-A*2402 positive or HLA-A*0201 positive) by Ficoll-Paque plus (Pharmacia) solution were separated by adherence to a plastic tissue culture dish (Becton Dickinson) so as to enrich them as the monocyte fraction. The monocyte-enriched population was cultured in the presence of 1000 U/ml of granulocyte-macrophage colony-stimulating factor (R&D System) and 1000 U/ml of interleukin (IL)-4 (R&D System) in AIM-V Medium (Invitrogen) containing 2% heat-inactivated autologous serum (AS). After 7 days of culture, the cytokine-induced DCs were pulsed with 20 micro-g/ml of each of the synthesized peptides in the presence of 3 micro g/ml of beta 2-microglobulin for 3 hr at 37 degrees C. in AIM-V Medium. The generated cells appeared to express DC-associated molecules, such as CD80, CD83, CD86 and HLA class II, on their cell surfaces (data not shown). These peptide-pulsed DCs were then inactivated by X ray-irradiated (20 Gy) and mixed at a 1:20 ratio with autologous CD8+ T cells, obtained by positive selection with CD8 Positive Isolation Kit (Dynal). These cultures were set up in 48-well plates (Corning); each well contained $1.5 \times 10^4$ peptide-pulsed DCs, $3 \times 10^5$ CD8+ T cells and 10 ng/ml of IL-7 (R&D System) in 0.5 ml of AIM-V/2% AS medium. Three days later, these cultures were supplemented with IL-2 (CHIRON) to a final concentration of 20 IU/ml. On day 7 and 14, the T cells were further stimulated with the autologous peptide-pulsed DCs. The DCs were prepared each time by the same way described above. CTLs were tested against peptide-pulsed TISI cells or T2 cells after the 3rd round of peptide stimulation on day 21 (Tanaka H et al., Br J Cancer 2001 Jan. 5, 84(1): 94-9; Umano Y et al., Br J Cancer 2001 Apr. 20, 84(8): 1052-7; Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

CTL Expansion Procedure

CTLs were expanded in culture using the method similar to the one described by Riddell et al. (Walter E A et al., N Engl J Med 1995 Oct. 19, 333(16): 1038-44; Riddell S R et al., Nat Med 1996 February, 2(2): 216-23). A total of $5 \times 10^4$ CTLs were suspended in 25 ml of AIM-V/5% AS medium with 2 kinds of human B-lymphoblastoid cell lines, inactivated by Mitomycin C, in the presence of 40 ng/ml of anti-CD3 monoclonal antibody (Pharmingen). One day after initiating the cultures, 120 IU/ml of IL-2 were added to the cultures. The cultures were fed with fresh AIM-V/5% AS medium containing 30 IU/ml of IL-2 on days 5, 8 and 11 (Tanaka H et al., Br J Cancer 2001 Jan. 5, 84(1): 94-9; Umano Y et al., Br J Cancer 2001 Apr. 20, 84(8): 1052-7; Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

Establishment of CTL Clones

The dilutions were made to have 0.3, 1, and 3 CTLs/well in 96 round-bottomed micro titer plate (Nalge Nunc International). CTLs were cultured with $1 \times 10^4$ cells/well of 2 kinds of human B-lymphoblastoid cell lines, 30 ng/ml of anti-CD3 antibody, and 125 U/ml of IL-2 in a total of 150 micro-l/well of AIM-V Medium containing 5% AS. 50 micro-l/well of IL-2 were added to the medium 10 days later to reach a final concentration of 125 U/ml IL-2. CTL activity was tested on the 14th day, and CTL clones were expanded using the same method as described above (Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

Specific CTL Activity

To examine specific CTL activity, IFN-gamma ELISPOT assay and IFN-gamma ELISA were performed. Peptide-pulsed TISI cells or T2 cells ($1 \times 10^4$/well) were prepared as stimulator cells. Cultured cells in 48-well plate, CTL lines and CTL clones were used as responder cells. IFN-gamma ELISPOT assay and IFN-gamma ELISA were performed under the manufacturer's procedure.

Establishment of the Cells Forcibly Expressing Either or Both of the Target Gene and HLA-A24 or HLA-A2

The cDNA encoding an open reading frame of target genes, HLA-A*2402 or HLA-A*0201 was amplified by PCR. The PCR-amplified product was cloned into expression vector. The plasmids were transfected into COS7, which is the target genes-null, HLA-A*0201-null and HLA-A*2402-null cell line, using lipofectamine 2000 (Invitrogen) according to the manufacturer's procedure. After 2 days from transfection, the transfected cells were harvested with versene (Invitrogen) and used as the stimulator cells ($5 \times 10^4$ cells/well) for CTL activity assay.

CTL Ability to Recognize the Target Cell Line that Endogenously Expressed TOPK and HLA-A*2402 or HLA-A*0201

The CTL clone was examined for its ability to recognize the target cell that endogenously expressed TOPK and HLA-A*2402 or HLA-A*0201. Established CTL clone was cultured with target cell lines ($5 \times 10^4$/well) for two overnight. After incubation, IFN-gamma in the culture media was measured by ELISA. IFN-gamma ELISA was performed under the manufacturer's procedure.

Results

Enhanced TOPK Expression in Cancers

The wide gene expression profile data obtained from various cancers using cDNA-microarray revealed that TOPK (GenBank Accession No. NM_018492; for example, SEQ ID No: 85) expression was specifically elevated in cancer tissues as compared with corresponding normal tissue. TOPK expression was validly elevated in 1 out of 15 AML, 15 out of 18 bladder cancers, 36 out of 40 breast cancers, 2 out of 6 cervical cancers, 6 out of 6 cholangiocellular carcinoma, 2 out of 6 colorectal cancers, 1 out of 1 diffuse-type gastric cancer, 5 out of 5 NSCLC, 1 out of 2 lymphomas, 7 out of 11 osteosarcoma, 12 out of 19 prostate cancers, 3 out of 12 renal carcinomas, 14 out of 14 SCLCs and 15 out of 29 soft tissue tumors (Table 1).

TABLE 1

Ratio of cases observed up-regulation of TOPK in cancerous tissues as compared with normal corresponding tissues.

| Cancer/Tumor | Ratio |
|---|---|
| AML | 1/15 |
| Bladder cancer | 15/18 |
| Breast cancer | 36/40 |
| Cervical cancer | 2/6 |
| Cholangiocellular carcinoma | 6/6 |
| Colorectal cancer | 2/6 |
| Diffuse-type gastric cancer | 1/1 |
| NSCLC | 5/5 |
| Lymphoma | 1/2 |
| Osteosarcoma | 7/11 |
| Prostate cancer | 12/19 |
| Renal carcinoma | 3/12 |
| SCLC | 14/14 |
| Soft tissue tumor | 15/29 |

Prediction of HLA-A24 Binding Peptides Derived from TOPK

Table 2a and 2b show the HLA-A24 binding of 9mer and 10mer peptides of TOPK in the order of high binding affinity. A total of 40 peptides having potential HLA-A24 binding ability were selected and examined to determine the epitope peptides.

TABLE 2a

HLA-A24 binding 9mer peptides derived from TOPK

| Start Position | amino acid sequence | Kd (nM) | SEQ ID NO |
|---|---|---|---|
| 289 | SYQKVIELF | 21 | 1 |
| 230 | IFAFGLTLW | 363 | 2 |
| 130 | RYKASQDPF | 451 | 3 |
| 237 | LWEMMTLSI | 1351 | 4 |
| 155 | KYLHQEKKL | 1906 | 5 |
| 232 | AFGLTLWEM | 3946 | 6 |
| 174 | VIKGDFETI | 4496 | 7 |
| 73 | HYRSVYQKR | 4663 | 8 |
| 235 | LTLWEMMTL | 4781 | 9 |
| 19 | SVLCSTPTI | 6522 | 10 |
| 205 | CYIGTEPWK | 7254 | 11 |
| 77 | VYQKRLMDE | 8604 | 12 |
| 270 | AYYAALGTR | 8621 | 13 |
| 58 | HSPWAVKKI | 9096 | 14 |
| 81 | RLMDEAKIL | 12527 | 15 |
| 278 | RPPINMEEL | 19706 | 16 |

TABLE 2a-continued

HLA-A24 binding 9mer peptides derived from TOPK

| Start Position | amino acid sequence | Kd (nM) | SEQ ID NO |
|---|---|---|---|
| 183 | KICDVGVSL | 25266 | 17 |
| 227 | KADIFAFGL | 25408 | 18 |
| 13 | LSEKKKSVL | 26380 | 19 |
| 146 | VALNMARGL | 26693 | 20 |
| 140 | AAIILKVAL | 28349 | 21 |
| 103 | FTEANDGSL | 29275 | 22 |
| 105 | EANDGSLCL | 29821 | 23 |
| 118 | GGEKSLNDL | 35171 | 24 |

TABLE 2b

HLA-A24 binding 10mer peptides derived from TOPK

| Start Position | amino acid sequence | Kd (nM) | SEQ ID NO |
|---|---|---|---|
| 31 | ASPFMQKLGF | 4764 | 25 |
| 155 | KYLHQEKKLL | 8099 | 26 |
| 288 | ESYQKVIELF | 9466 | 27 |
| 289 | SYQKVIELFS | 9631 | 28 |
| 130 | RYKASQDPFP | 9917 | 29 |
| 47 | YLMKRSPRGL | 10978 | 30 |
| 73 | HYRSVYQKRL | 11919 | 31 |
| 102 | AFTEANDGSL | 14375 | 32 |
| 39 | GFGTGVNVYL | 21925 | 33 |
| 4 | ISNFKTPSKL | 21974 | 34 |
| 77 | VYQKRLMDEA | 23521 | 35 |
| 241 | MTLSIPHINL | 27049 | 36 |
| 12 | KLSEKKKSVL | 28153 | 37 |
| 148 | LNMARGLKYL | 30397 | 38 |
| 145 | KVALNMARGL | 32052 | 39 |
| 114 | AMEYGGEKSL | 32705 | 40 |

Start position indicates the number of amino acid residue from the N-terminus of TOPK. Dissociation constant [Kd (nM)] is derived from "NetMHC 3.0".

Prediction of HLA-A02 Binding Peptides Derived from TOPK

Table 3a and 3b show the HLA-A02 binding 9mer and 10mer peptides of TOPK respectively in the order of high binding affinity. A total of 44 peptides with potential HLA-A02 binding ability were selected and examined to determine the epitope peptides.

TABLE 3a

HLA-A02 binding 9mer peptides derived from TOPK

| Start Position | amino acid sequence | Kd (nM) | SEQ ID NO |
|---|---|---|---|
| 55 | GLSHSPWAV | 13 | 41 |
| 240 | MMTLSIPHI | 37 | 42 |
| 34 | FMQKLGFGT | 76 | 43 |
| 236 | TLWEMMTLS | 150 | 44 |
| 19 | SVLCSTPTI | 230 | 45 |
| 134 | SQDPFPAAI | 238 | 46 |
| 183 | KICDVGVSL | 415 | 47 |
| 81 | RLMDEAKIL | 470 | 48 |
| 149 | NMARGLKYL | 524 | 49 |
| 235 | LTLWEMMTL | 648 | 50 |
| 12 | KLSEKKKSV | 775 | 51 |
| 227 | KADIFAFGL | 1542 | 52 |
| 285 | ELDESYQKV | 1902 | 53 |
| 47 | YLMKRSPRG | 2476 | 54 |
| 310 | SAAHIVEAL | 3199 | 55 |
| 132 | KASQDPFPA | 3496 | 56 |
| 242 | TLSIPHINL | 3753 | 57 |
| 156 | YLHQEKKLL | 4077 | 58 |
| 138 | FPAAIILKV | 4228 | 59 |
| 142 | IILKVALNM | 4330 | 60 |

TABLE 3b

HLA-A02 binding 10mer peptides derived from TOPK

| Start Position | amino acid sequence | Kd (nM) | SEQ ID NO |
|---|---|---|---|
| 190 | SLPLDENMTV | 30 | 61 |
| 236 | TLWEMMTLSI | 32 | 62 |
| 231 | FAFGLTLWEM | 41 | 63 |
| 47 | YLMKRSPRGL | 64 | 64 |
| 234 | GLTLWEMMTL | 74 | 65 |
| 239 | EMMTLSIPHI | 93 | 66 |
| 290 | YQKVIELFSV | 101 | 67 |
| 37 | KLGFGTGVNV | 192 | 68 |
| 20 | VLCSTPTINI | 290 | 69 |
| 241 | MTLSIPHINL | 310 | 70 |
| 272 | YAALGTRPPI | 1347 | 71 |
| 88 | ILKSLHHPNI | 1656 | 72 |
| 81 | RLMDEAKILK | 1720 | 73 |
| 313 | HIVEALETDV | 2345 | 74 |
| 54 | RGLSHSPWAV | 2364 | 75 |
| 142 | IILKVALNMA | 2428 | 76 |
| 35 | MQKLGFGTGV | 2432 | 77 |
| 110 | SLCLAMEYGG | 3236 | 78 |
| 223 | VITDKADIFA | 3422 | 79 |
| 274 | ALGTRPPINM | 3575 | 80 |
| 173 | VVIKGDFETI | 3955 | 81 |
| 141 | AIILKVALNM | 4247 | 82 |
| 292 | KVIELFSVCT | 4637 | 83 |
| 180 | ETIKICDVGV | 4911 | 84 |

Start position indicates the number of amino acid residue from the N-terminus of TOPK. Dissociation constant [Kd (nM)] is derived from "NetMHC 3.0".

CTL Induction with the Predicted Peptides from TOPK Restricted with HLA-A*2402

Figure 1:
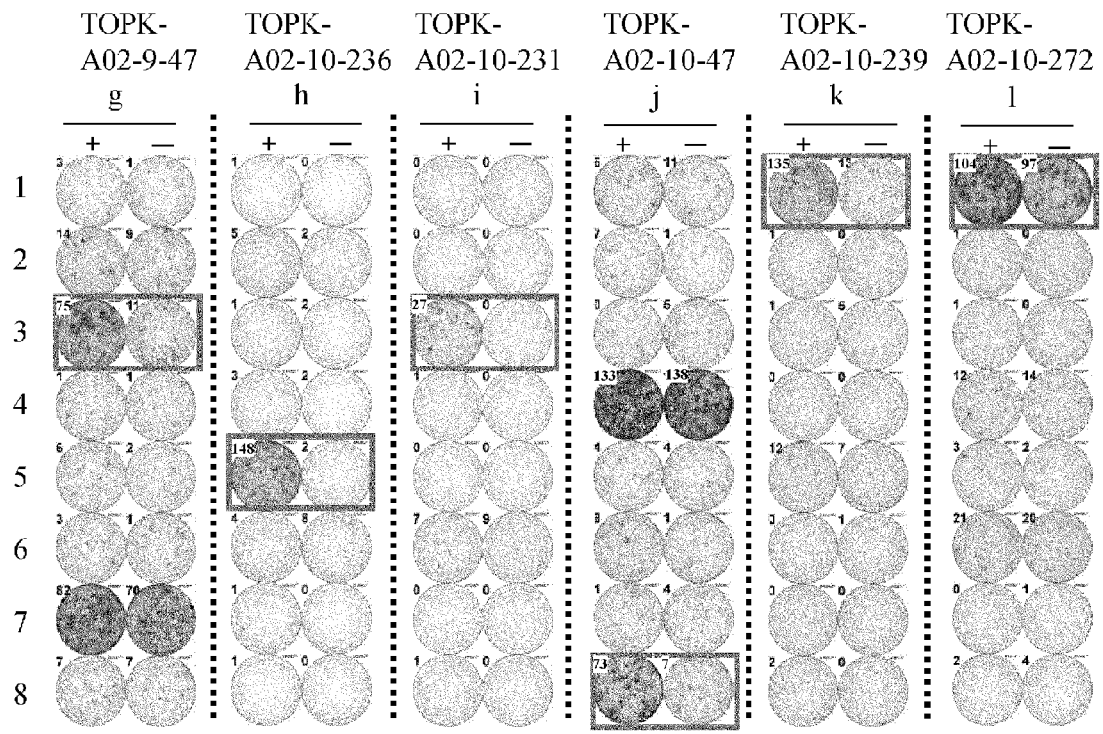
FIG. 1 is composed of a series of photographs, (a)-(f), depicting the results of interferon (IFN)-gamma enzyme linked immunospot (ELISPOT) assay on CTLs that were induced with peptides derived from TOPK. The CTLs in well number #8 induced with TOPK-A24-9-230 (SEQ ID NO: 2) (a), in #3 induced with TOPK-A24-9-130 (SEQ ID NO: 3) (b), in #3 induced with TOPK-A24-9-232 (SEQ ID NO: 6) (c), in #2 induced with TOPK-A24-10-288 (SEQ ID NO: 27) (d) and in #4 induced with TOPK-A24-10-289 (SEQ ID NO: 28) (e) showed potent IFN-gamma production as compared with the control, respectively. The square on the well of these pictures indicates that the cells from corresponding well were expanded to establish CTL lines. In contrast, as is typical of negative data, it no specific IFN-gamma production was observed from the CTL stimulated with TOPK-A24-9-289 (SEQ ID NO: 1) (f). In the figures, "+" indicates the IFN-gamma production against target cells pulsed with the appropriate peptide, and "−" indicates the IFN-gamma production against target cells not pulsed with any peptides.
Figure 2:
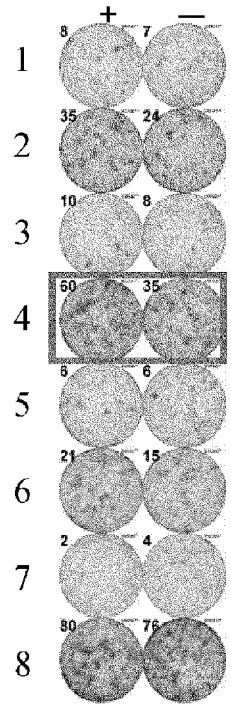
Figure 2:
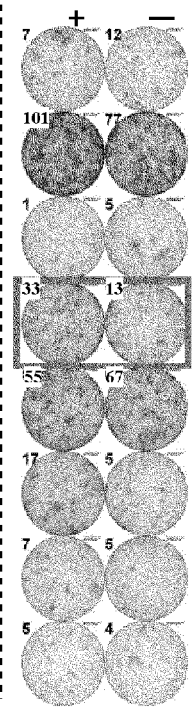
Figure 2:
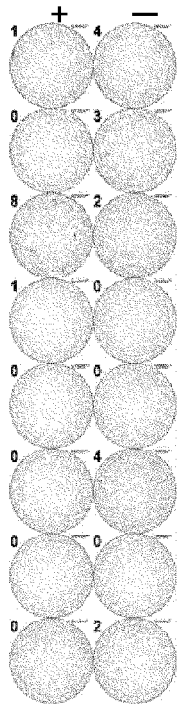

CTLs for those peptides derived from TOPK were generated according to the protocols as described in "Materials and Methods". Peptide specific CTL activity was detected by IFN-gamma ELISPOT assay (FIG. 1). Well number #8 with TOPK-A24-9-230 (SEQ ID NO: 2) (a), #3 with TOPK-A24-9-130 (SEQ ID NO: 3) (b), #3 with TOPK-A24-9-232 (SEQ ID NO: 6) (c), #2 with TOPK-A24-10-288 (SEQ ID NO: 27) (d) and #4 with TOPK-A24-10-289 (SEQ ID NO: 28) (e) demonstrated potent IFN-gamma production as compared to the control wells. On the other hand, no specific CTL activity was detected by stimulation with other peptides shown in Table 2a and 2b, despite those peptides had possible binding activity with HLA-A*2402. As is typical of negative data, no specific IFN-gamma production was observed from the CTL stimulated with TOPK-A24-9-289 (SEQ ID NO: 1) (f). Taken together, these results suggest that the 5 selected peptides derived from TOPK could induce potent CTLs.

CTL Induction with the Predicted Peptides from TOPK Restricted with HLA-A*0201

Peptide specific CTL activity was detected by IFN-gamma ELISPOT assay (FIG. 2). Well number #7 with TOPK-A02-9-240 (SEQ ID NO: 42) (a), #4 with TOPK-A02-9-19 (SEQ ID NO: 45) (b), #2 with TOPK-A02-9-183 (SEQ ID NO: 47) (c), #8 with TOPK-A02-9-235 (SEQ ID NO: 50) (d), #4 with TOPK-A02-9-12 (SEQ ID NO: 51) (e), #3 with TOPK-A02-9-285 (SEQ ID NO: 53) (f), #3 with TOPK-A02-9-47 (SEQ ID NO: 54) (g), #5 with TOPK-A02-10-236 (SEQ ID NO: 62) (h), #3 with TOPK-A02-10-231 (SEQ ID NO: 63) (i), #8 with TOPK-A02-10-47 (SEQ ID NO: 64) (j), #1 with TOPK-A02-10-239 (SEQ ID NO: 66) (k), #1 with TOPK-A02-10-272 (SEQ ID NO: 71) (l), #4 with TOPK-A02-10-88 (SEQ ID NO: 72) (m) and #4 with TOPK-A02-10-142 (SEQ ID NO: 76) (n) demonstrated potent IFN-gamma production as compared to the control wells. On the other hand, no specific CTL activity was detected by stimulation with other peptides shown in Table 3a and 3b, despite those peptides had possible binding activity with HLA-A*0201. As is typical of negative data, no specific IFN-gamma production was observed from the CTL stimulated with TOPK-A02-9-55 (SEQ ID NO: 41) (o). Taken together, these results suggest that the 14 selected peptides derived from TOPK could induce potent CTLs.

Establishment of CTL Line and Clone Against TOPK Derived Peptide

Figure 3:
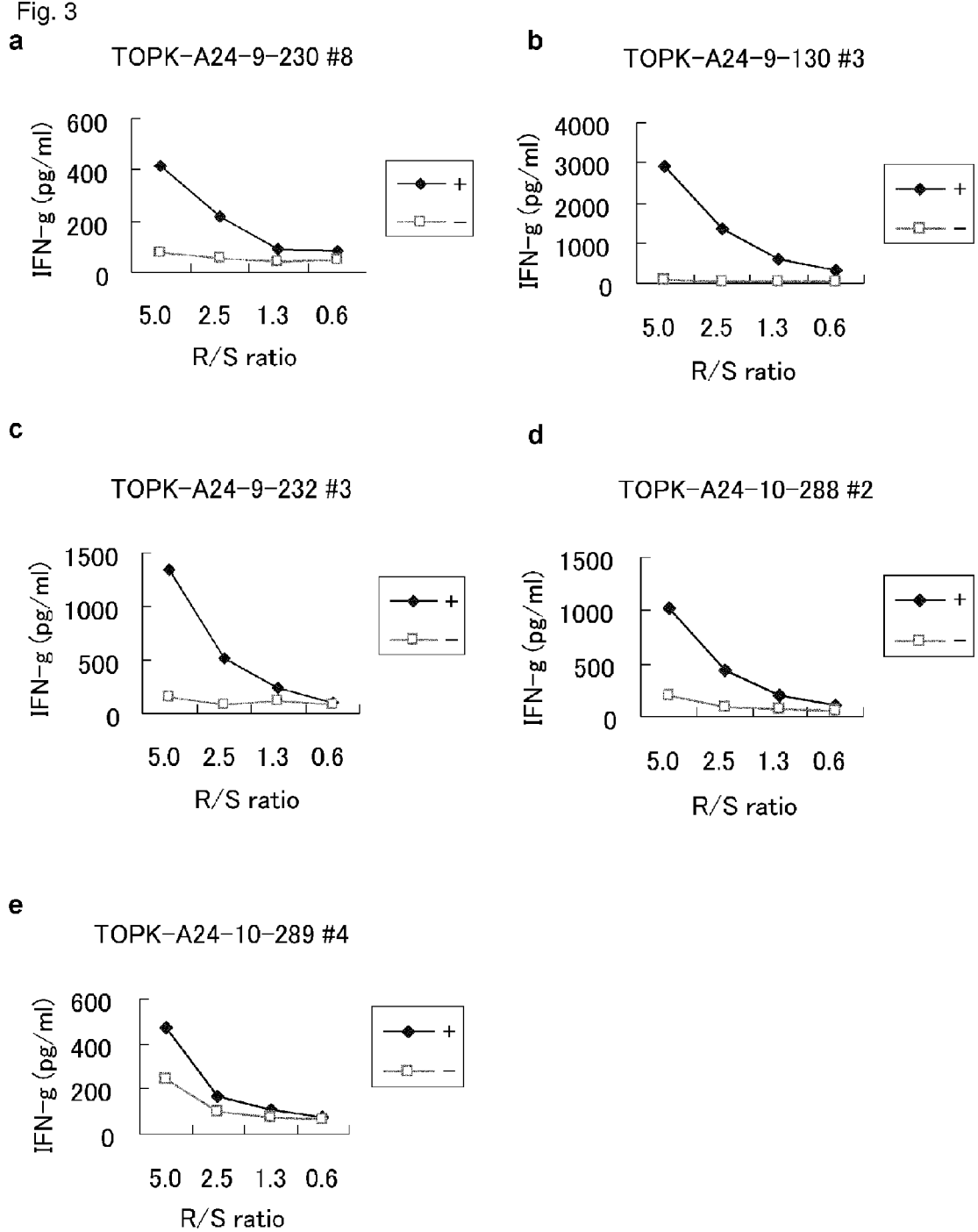
FIG. 3 is composed of a series of line graphs, (a)-(e), depicting the IFN-gamma production of the CTL lines stimulated with TOPK-A24-9-230 (SEQ ID NO: 2) (a), TOPK-A24-9-130 (SEQ ID NO: 3) (b), TOPK-A24-9-232 (SEQ ID NO: 6) (c), TOPK-A24-10-288 (SEQ ID NO: 27) (d) and TOPK-A24-10-289 (SEQ ID NO: 28) (e). The quantity of IFN-gamma which CTLs produced was measured by IFN-gamma enzyme-linked immunosorbent assay (ELISA). The results demonstrate that CTL lines established by stimulation with each peptide show potent IFN-gamma production as compared with the control. In the figures, "+" indicates the IFN-gamma production against target cells pulsed with the appropriate peptide, and "−" indicates the IFN-gamma production against target cells not pulsed with any peptides. R/S ratio indicates the ratio of the number of responder cells (CTL line) and stimulator cells.
Figure 4:
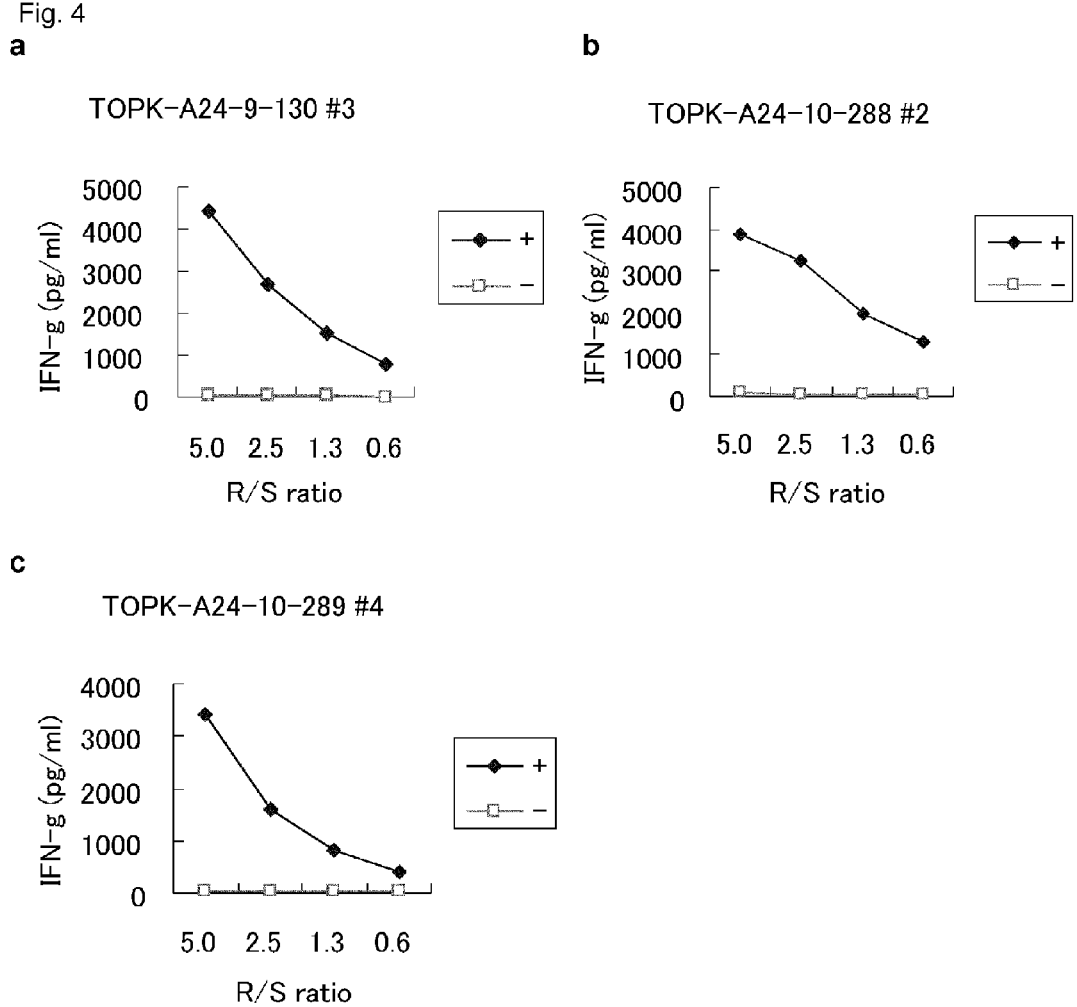
FIG. 4 is composed of a series of line graphs, (a)-(c), depicting the IFN-gamma production of the CTL clones established by limiting dilution from the CTL lines stimulated with TOPK-A24-9-130 (SEQ ID NO: 3) (a), TOPK-A24-10-288 (SEQ ID NO: 27) (b) and TOPK-A24-10-289 (SEQ ID NO: 28) (c). The results demonstrate that CTL clones established by stimulation with each peptide show potent IFN-gamma production as compared with the control. In the figure, "+" indicates the IFN-gamma production against target cells pulsed with the appropriate peptide and "−" indicates the IFN-gamma production against target cells not pulsed with any peptides. R/S ratio indicates the ratio of the number of responder cells (CTL clone) and stimulator cells.

The cells in the well number #8 with TOPK-A24-9-230 (SEQ ID NO: 2) (a), #3 with TOPK-A24-9-130 (SEQ ID NO: 3) (b), #3 with TOPK-A24-9-232 (SEQ ID NO: 6) (c), #2 with TOPK-A24-10-288 (SEQ ID NO: 27) (d) and #4 with TOPK-A24-10-289 (SEQ ID NO: 28) (e) that showed peptide specific CTL activity by IFN-gamma ELISPOT assay were expanded and established the CTL lines. CTL activities of these CTL lines were measured by IFN-gamma ELISA (FIG. 3). CTL lines demonstrated potent IFN-gamma production against target cells pulsed with the corresponding peptide as compared to target cells without peptide pulse. Furthermore, the CTL clones were established by limiting dilution from the CTL lines as described in "Materials and Methods", and IFN-gamma production from the CTL clones against TISI cells pulsed with corresponding peptide was measured by IFN-gamma ELISA. Potent IFN-gamma production was observed from the CTL clones stimulated with TOPK-A24-9-130 (SEQ ID NO: 3) (a), TOPK-A24-10-288 (SEQ ID NO: 27) (b) and TOPK-A24-10-289 (SEQ ID NO: 28) (c) (FIG. 4).

Figure 6:
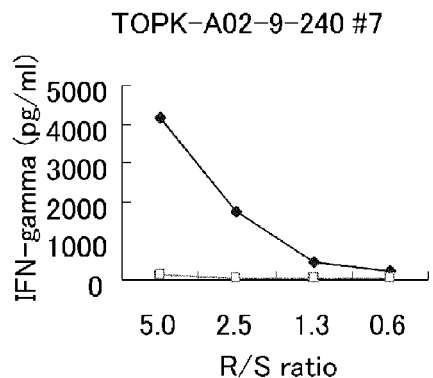
FIG. 6 is composed of a pair of line graphs, (a) and (b), depicting the IFN-gamma production of the CTL clones established by limiting dilution from the CTL lines stimulated with TOPK-A02-9-240 (SEQ ID NO: 42) (a) and TOPK-A02-9-285 (SEQ ID NO: 53) (b). The results demonstrate that the CTL clones established by stimulation with each peptide show potent IFN-gamma production as compared with the control. In the figure, "+" indicates the IFN-gamma production against target cells pulsed with the appropriate peptide and "−" indicates the IFN-gamma production against target cells not pulsed with any peptides. R/S ratio indicates the ratio of the number of responder cells (CTL clone) and stimulator cells.
Figure 6:
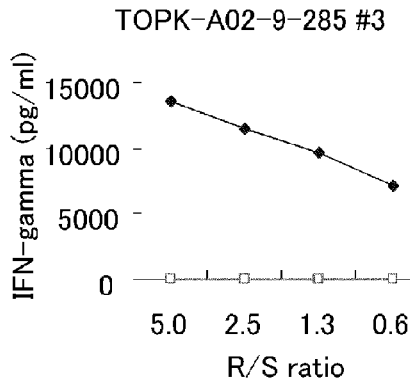

The cells in the well number #7 with TOPK-A02-9-240 (SEQ ID NO: 42) (a), #4 with TOPK-A02-9-19 (SEQ ID NO: 45) (b), #8 with TOPK-A02-9-235 (SEQ ID NO: 50) (c), #4 with TOPK-A02-9-12 (SEQ ID NO: 51) (d), #3 with TOPK-A02-9-285 (SEQ ID NO: 53) (e), #3 with TOPK-A02-9-47 (SEQ ID NO: 54) (f), #5 with TOPK-A02-10-236 (SEQ ID NO: 62) (g), #3 with TOPK-A02-10-231 (SEQ ID NO: 63) (h), #8 with TOPK-A02-10-47 (SEQ ID NO: 64) (i), #1 with TOPK-A02-10-239 (SEQ ID NO: 66) (j) and #4 with TOPK-A02-10-88 (SEQ ID NO: 72) (k) that showed peptide specific CTL activity by IFN-gamma ELISPOT assay were expanded and established the CTL lines. The CTL activities of these CTL lines were measured by IFN-gamma ELISA (FIG. 5). CTL lines demonstrated potent IFN-gamma production against target cells pulsed with the corresponding peptide as compared to target cells without peptide pulse. Furthermore, the CTL clones were established by limiting dilution from the CTL lines as described in "Materials and Methods", and IFN-gamma production from the CTL clones against T2 cells pulsed with corresponding peptide was measured by IFN-gamma ELISA. Potent IFN-gamma production was observed from the CTL clones stimulated with TOPK-A02-9-240 (SEQ ID NO: 42) (a) and TOPK-A02-9-285 (SEQ ID NO: 53) (b) (FIG. 6).

Specific CTL Activity Against Target Cells Expressing TOPK and HLA-A*2402 or HLA-A*0201

Figure 7:
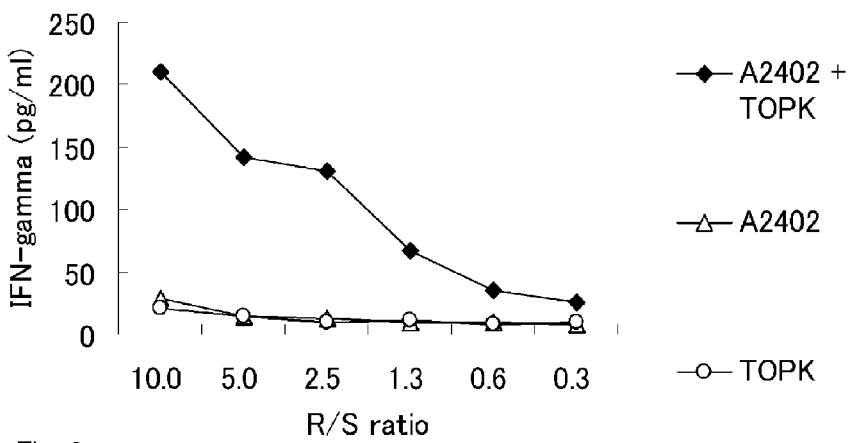
FIG. 7 is a line graph depicting the specific CTL activity of CTL clones against the target cells that express TOPK and HLA-A*2402. COS7 cells transfected with HLA-A*2402 or the full length TOPK gene were prepared as the controls. The CTL clone established with TOPK-A24-10-289 (SEQ ID NO: 28) showed specific CTL activity against COS7 cells transfected with both TOPK and HLA-A*2402 (lozenge). On the other hand, no significant specific CTL activity was detected against target cells expressing either HLA-A*2402 (triangle) or TOPK (circle).
Figure 8:
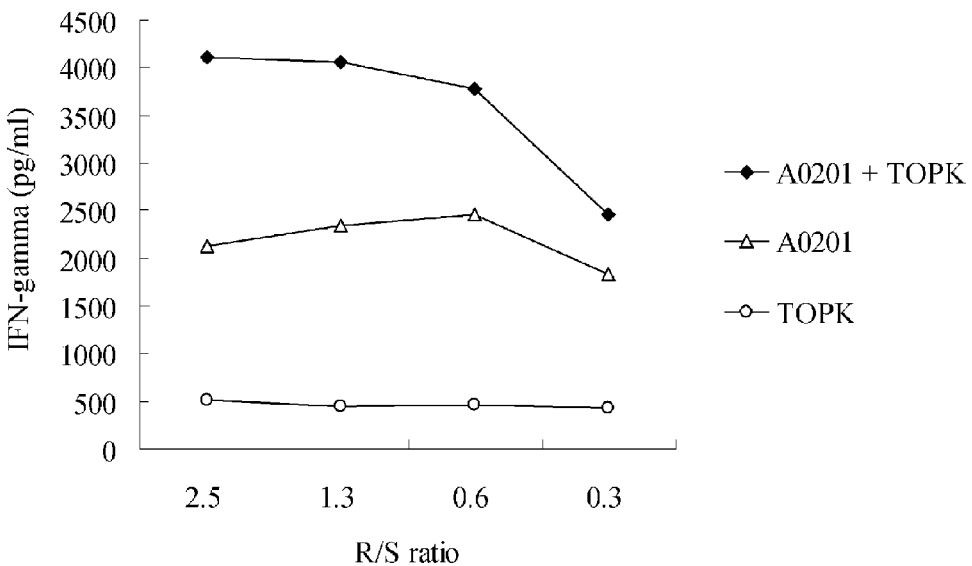
FIG. 8 is a line graph depicting the specific CTL activity of CTL lines against the target cells that express TOPK and HLA-A*0201. COS7 cells transfected with HLA-A*0201 or the full length TOPK gene were prepared as the controls. The CTL line established with TOPK-A02-9-240 (SEQ ID NO: 42) showed specific CTL activity against COS7 cells transfected with both TOPK and HLA-A*0201 (lozenge). On the other hand, no significant specific CTL activity was detected against target cells expressing either HLA-A*0201 (triangle) or TOPK (circle).

The established CTL clone raised against TOPK-A24-10-289 (SEQ ID NO: 28) peptide was examined for the ability to recognize target cells that express TOPK and HLA-A*2402 molecule. COS7 cells transfected with both the full length of TOPK and HLA-A*2402 gene (a specific model for the target cells that express TOPK and HLA-A*2402 gene) were prepared as a stimulator cells, and COS7 cells transfected with either full length of TOPK or HLA-A*2402 were used as the controls. In FIG. 7, the CTL clone stimulated with TOPK-A24-10-289 (SEQ ID NO: 28) showed potent CTL activity against COS7 cells expressing both TOPK and HLA-A*2402. On the other hand, no significant specific CTL activity was detected against the controls. Thus, these data clearly demonstrate that TOPK-A24-10-289 (SEQ ID NO: 28) peptide is endogenously processed and expressed on the target cells with HLA-A*2402 molecule and is recognized by the CTLs. The established CTL line raised against TOPK-A02-9-240 (SEQ ID NO: 42) peptide was examined for the ability to recognize target cells that express TOPK and HLA-A*0201 molecule. COS7 cells transfected with both the full length of TOPK and HLA-A*0201 gene (a specific model for the target cells that express TOPK and HLA-A*0201 gene) were prepared as a stimulator cells, and COS7 cells transfected with either full length of TOPK or HLA-A*0201 were used as the controls. In FIG. 8, the CTL line stimulated with TOPK-A02-9-240 (SEQ ID NO: 42) showed potent CTL activity against COS7 cells expressing both TOPK and HLA-A*0201. On the other hand, no significant specific CTL activity was detected against the controls. Thus, these data clearly demonstrate that TOPK-A02-9-240 (SEQ ID NO: 42) peptide is endogenously processed and expressed on the target cells with HLA-A*0201 molecule and is recognized by the CTLs. These results indicate that these peptides derived from TOPK may be available to apply the cancer vaccines for patients with TOPK expressing tumors.

Homology Analysis of Antigen Peptides

The CTLs stimulated with TOPK-A24-9-230 (SEQ ID NO: 2), TOPK-A24-9-130 (SEQ ID NO: 3), TOPK-A24-9-232 (SEQ ID NO: 6), TOPK-A24-10-288 (SEQ ID NO: 27), TOPK-A24-10-289 (SEQ ID NO: 28), TOPK-A02-9-240 (SEQ ID NO: 42), TOPK-A02-9-19 (SEQ ID NO: 45), TOPK-A02-9-183 (SEQ ID NO: 47), TOPK-A02-9-235 (SEQ ID NO: 50), TOPK-A02-9-12 (SEQ ID NO: 51), TOPK-A02-9-285 (SEQ ID NO: 53), TOPK-A02-9-47 (SEQ ID NO: 54), TOPK-A02-10-236 (SEQ ID NO: 62), TOPK-A02-10-231 (SEQ ID NO: 63), TOPK-A02-10-47 (SEQ ID NO: 64), TOPK-A02-10-239 (SEQ ID NO: 66), TOPK-A02-10-272 (SEQ ID NO: 71), TOPK-A02-10-88 (SEQ ID NO: 72) or TOPK-A02-10-142 (SEQ ID NO: 76) showed significant and specific CTL activity. This result may be due to the fact that these sequences are homologous to peptide derived from other molecules that are known to sensitize the human immune system. To exclude this possibility, homology analyses were performed for these peptide sequences using as queries the BLAST algorithm (http://www.ncbi.nlm.nih.gov/blast/blast.cgi) which revealed no sequence with significant homology. The results of homology analyses indicate that the sequence of TOPK-A24-9-230 (SEQ ID NO: 2), TOPK-A24-9-130 (SEQ ID NO: 3), TOPK-A24-9-232 (SEQ ID NO: 6), TOPK-A24-10-288 (SEQ ID NO: 27), TOPK-A24-10-289 (SEQ ID NO: 28), TOPK-A02-9-240 (SEQ ID NO: 42), TOPK-A02-9-19 (SEQ ID NO: 45), TOPK-A02-9-183 (SEQ ID NO: 47), TOPK-A02-9-235 (SEQ ID NO: 50), TOPK-A02-9-12 (SEQ ID NO: 51), TOPK-A02-9-285 (SEQ ID NO: 53), TOPK-A02-9-47 (SEQ ID NO: 54), TOPK-A02-10-236 (SEQ ID NO: 62), TOPK-A02-10-231 (SEQ ID NO: 63), TOPK-A02-10-47 (SEQ ID NO: 64), TOPK-A02-10-239 (SEQ ID NO: 66), TOPK-A02-10-272 (SEQ ID NO: 71), TOPK-A02-10-88 (SEQ ID NO: 72) and TOPK-A02-10-142 (SEQ ID NO: 76) are unique and thus, there is little possibility, to our best knowledge, that this molecules raise unintended immunologic response to some unrelated molecule. In conclusion, the novel HLA-A24 or HLA-A02 epitope peptides derived from TOPK identified herein may find utility in the field of cancer immunotherapy.

INDUSTRIAL APPLICABILITY

The present invention provides new TAAs, particularly those derived from TOPK, that may induce potent and specific anti-tumor immune responses and thus have applicability to a wide variety of cancer types. Such TAAs can find use as peptide vaccines against diseases associated with TOPK, e.g., cancer, more particularly, acute myeloid leukemia (AML), bladder cancer, breast cancer, cervical cancer, cholangiocellular carcinoma, colorectal cancer, diffuse-type gastric cancer, non small cell lung cancer (NSCLC), lymphoma, osteosarcoma, prostate cancer, renal carcinoma, small cell lung cancer (SCLC) and soft tissue tumor.

While the present invention is herein described in detail and with reference to specific embodiments thereof, it is to be understood that the foregoing description is exemplary and explanatory in nature and is intended to illustrate the present invention and its preferred embodiments. Through routine experimentation, one skilled in the art will readily recognize that various changes and modifications can be made therein without departing from the spirit and scope of the present invention, the metes and bounds of which are defined by the appended claims.

The invention claimed is:

1. A method of inducing an immune response against cancer in a subject, said method comprising the step of administering to the subject a composition comprising an isolated peptide of less than 15 amino acids, wherein the peptide is selected from the group consisting of (a), (b), and (c) below:

(a) an isolated peptide comprising an amino acid sequence selected from the group consisting of SEQ ID NOs: 2, 3 and 42;

(b) an isolated peptide comprising an amino acid sequence selected from the group consisting of SEQ ID NOs: 2, 3 and 42, in which 1 or 2 amino acid(s) are substituted, inserted, deleted, and/or added, wherein the peptide has CTL inducibility, or a polynucleotide encoding the peptide; and (c) an isolated peptide consisting of an amino acid sequence selected from the group consisting of SEQ ID NOs: 2, 3 and 42.

* * * * *